United States Patent
Krawczyk et al.

(10) Patent No.: US 10,273,485 B2
(45) Date of Patent: Apr. 30, 2019

(54) MODIFIED MICROORGANISM WITH IMPROVED BIOMASS SEPARATION BEHAVIOUR

(71) Applicant: BASF SE, Ludwigshafen (DE)

(72) Inventors: Joanna Martyna Krawczyk, Mannheim (DE); Stefan Haefner, Speyer (DE); Hartwig Schröder, Nußloch (DE); Esther Dantas Costa, Mannheim (DE); Oskar Zelder, Speyer (DE); Gregory Von Abendroth, White Plains, NY (US); Christoph Wittmann, Saarlouis (DE); René Stellmacher, Binningen (CH); Judith Becker, Kutzhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/116,600

(22) PCT Filed: Feb. 6, 2015

(86) PCT No.: PCT/EP2015/052523
§ 371 (c)(1),
(2) Date: Aug. 4, 2016

(87) PCT Pub. No.: WO2015/118111
PCT Pub. Date: Aug. 13, 2015

(65) Prior Publication Data
US 2016/0362696 A1 Dec. 15, 2016

(51) Int. Cl.
*C12N 1/20* (2006.01)
*C12N 15/52* (2006.01)
*C12N 1/02* (2006.01)
*C12N 9/12* (2006.01)
*C12P 7/46* (2006.01)
*C12N 9/04* (2006.01)
*C12N 9/10* (2006.01)
*C12N 15/74* (2006.01)

(52) U.S. Cl.
CPC .............. *C12N 15/52* (2013.01); *C12N 1/02* (2013.01); *C12N 9/0006* (2013.01); *C12N 9/1029* (2013.01); *C12N 9/1288* (2013.01); *C12N 15/74* (2013.01); *C12P 7/46* (2013.01); *C12Y 101/01* (2013.01); *C12Y 203/01054* (2013.01); *C12Y 207/08031* (2013.01)

(58) Field of Classification Search
CPC .......... C12N 1/02; C12N 9/1288; C12N 15/52
USPC ....................................... 435/252.3
See application file for complete search history.

(56) References Cited

U.S. PATENT DOCUMENTS

2010/0159543 A1  6/2010  Scholten et al.

FOREIGN PATENT DOCUMENTS

| WO | WO-2005/052135 A1 | 6/2005 |
|----|-------------------|--------|
| WO | WO-2009/024294 A1 | 2/2009 |
| WO | WO-2010/092155 A1 | 8/2010 |
| WO | WO-2013/087884 A1 | 6/2013 |
| WO | WO-2014/018596 A2 | 1/2014 |

OTHER PUBLICATIONS

Kuhnert et al. International J. of Systematic & evolutionary Microbiology, 2010, 60, 44-50.*
Hong et al., The genome sequence of the capnophilic rumen bacterium Mannheimia succiniciproducens, Nat. Biotechnol., 22(10):1275-81 (2004).
Nothaft et al., In vivo analysis of HPr reveals a fructose-specific phosphotransferase system that confers high-affinity uptake in Streptomyces coelicolor, J. Bacteriol., 185(3):929-37 (2003).
Patel et al., Functional characterization of UDP-glucose:undecaprenyl-phosphate glucose-1-phosphate transferases of *Escherichia coli* and *Caulobacter crescentus*, J. Bacteriol., 194(10):2646-57 (2012).
Tenorio et al., Systematic characterization of *Escherichia coli* genes/ORFs affecting biofilm formation, FEMS Microbiol. Lett., 225(1):107-14 (2003).
UniProtKB—Q65SG1, *Mannheimia succiniciproducens* (strain MBEL55E), Oct. 25, 2004.

* cited by examiner

*Primary Examiner* — Tekchand Saidha
(74) *Attorney, Agent, or Firm* — Marshall, Gerstein & Borun LLP

(57) ABSTRACT

The present invention relates to a modified microorganism having, compared to its wild-type, a reduced activity of the enzyme that is encoded by the wcaJ-gene. The present invention also relates to a method for producing an organic compound and to the use of a modified microorganism.

12 Claims, 6 Drawing Sheets
Specification includes a Sequence Listing.

SEQUENCE LISTING

<160> NUMBER OF SEQ ID NOS: 16

<210> SEQ ID NO 1
<211> LENGTH: 1517
<212> TYPE: DNA
<213> ORGANISM: Basfia succiniciproducens
<220> FEATURE:
<221> NAME/KEY: MISC_FEATURE
<223> OTHER INFORMATION: 16 S rDNA of strain DD1

<400> SEQUENCE: 1
tttgatcctg gctcagattg aacgctggcg gcaggcttaa cacatgcaag tcgaacggta        60
gcgggaggaa agcttgcttt ctttgccgac gagtggcgga cgggtgagta atgcttgggg       120
atctggctta tggaggggga taacgacggg aaactgtcgc taataccgcg taatatcttc       180
ggattaaagg gtgggacttt cgggccaccc gccataagat gagcccaagt gggattaggt       240
agttggtggg gtaaaggcct accaagccga cgatctctag ctggtctgag aggatgacca       300
gccacactgg aactgagaca cggtccagac tcctacggga gcagcagtg gggaatattg        360 cacaatgggg ggaaccctga tgcagccatg ccgcgtgaat gaagaaggcc ttcgggttgt       420

```
aaagttcttt cggtgacgag gaaggtgttt gttttaatag gacaagcaat tgacgttaat    480
cacagaagaa gcaccggcta actccgtgcc agcagccgcg gtaataccgga gggtgcgagc   540 gttaatcgga ataactgggc gtaaagggca tgcaggcgga cttttaagtg agatgtgaaa   600
gccccgggct taacctggga attgcatttc agactgggag tctagagtac tttagggagg   660
ggtagaattc cacgtgtagc ggtgaaatgc gtagagatgt ggaggaatac cgaaggcgaa   720
ggcagcccct tgggaagata ctgacgctca tatgcgaaag cgtggggagc aaacaggatt   780
agataccctg gtagtccacg cggtaaacgc tgtcgatttg gggattgggc tttaggcctg   840
gtgctcgtag ctaacgtgat aaatcgaccg cctggggagt acggccgcaa ggttaaaact   900
caaatgaatt gacggggggcc cgcacaagcg gtggagcatg tggtttaatt cgatgcaacg   960
cgaagaacct tacctactct tgacatccag agaatcctgt agagatacgg gagtgccttc   1020
gggagctctg agacaggtgc tgcatggctg tcgtcagctc gtgttgtgaa atgttgggtt   1080
aagtcccgca acgagcgcaa cccttatcct ttgttgccag catgtaaaga tgggaactca   1140
aaggagactg ccggtgacaa accggaggaa ggtgggggatg acgtcaagtc atcatggccc   1200
ttacgagtag ggctacacac gtgctacaat ggtgcataca gagggcggcg ataccgcgag   1260
gtagagcgaa tctcagaaag tgcatcgtag tccggattgg agtctgcaac tcgactccat   1320
gaagtcggaa tcgctagtaa tcgcaaatca gaatgttgcg gtgaatacgt tcccgggcct   1380
tgtacacacc gcccgtcaca ccatgggagt gggttgtacc agaagtagat agcttaacct   1440
tcgggggggg cgtttaccac ggtatgattc atgactgggg tgaagtcgta acaaggtaac   1500
cgtaggggaa cctgcgg                                                  1517
```

<210> SEQ ID NO 2
<211> LENGTH: 3008
<212> TYPE: DNA
<213> ORGANISM: Basfia succiniciproducens
<220> FEATURE:
<221> NAME/KEY: MISC_FEATURE
<223> OTHER INFORMATION: 23 S rDNA of strain DD1

<400> SEQUENCE: 2

```
agtaataacg aacgacacag gtataagaat acttgaggtt gtatggttaa gtgactaagc     60
gtacaaggtg gatgccttgg caatcagagg cgaagaagga cgtgctaatc tgcgaaaagc    120
ttgggtgagt tgataagaag cgtctaaccc aagatatccg aatgggggcaa cccagtagat   180 gaagaatcta ctatcaataa ccgaatccat aggttattga ggcaaaccgg gagaactgaa    240
acatctaagt accccgagga aaagaaatca accgagatta cgtcagtagc ggcgagcgaa    300
agcgtaagag ccggcaagtg atagcatgag gattagagga atcggctggg aagccgggcg   360
gcacagggtg atagccccgt acttgaaaat cattgtgtgg tactgagctt gcgagaagta    420
gggcgggaca cgagaaatcc tgtttgaaga aggggggacc atcctccaag gctaaatact   480
cctgattgac cgatagtgaa ccagtactgt gaaggaaagg cgaaaagaac cccggtgagg    540
ggagtgaaat agaacctgaa accttgtacg tacaagcagt gggagcccgc gagggtgact    600
gcgtaccttt tgtataatgg gtcagcgact tatattatgt agcgaggtta accgaatagg    660
ggagccgaag ggaaaccgag tcttaactgg gcgtcgagtt gcatgatata gacccgaaac   720
ccggtgatct agccatgggc aggttgaagg ttgggtaaca ctaactggag gaccgaaccg    780
actaatgttg aaaaattagc ggatgacctg tggctggggg tgaaaggcca atcaaaccgg    840
gagatagctg gttctccccg aaatctattt aggtagagcc ttatgtgaat accttcgggg    900
```

```
gtagagcact gtttcggcta gggggccatc ccggcttacc aacccgatgc aaactgcgaa    960
taccgaagag taatgcatag gagacacacg gcgggtgcta acgttcgtcg tggagaggga   1020
aacaacccag accgccagct aaggtcccaa agtttatatt aagtgggaaa cgaagtggga   1080
aggcttagac agctaggatg ttggcttaga agcagccatc atttaaagaa agcgtaatag   1140
ctcactagtc gagtcggcct gcgcggaaga tgtaacgggg ctcaaatata gcaccgaagc   1200
tgcggcatca ggcgtaagcc tgttgggtag gggagcgtcg tgtaagcgga agaaggtggt   1260
tcgagagggc tgctggacgt atcacgagtg cgaatgctga cataagtaac gataaaacgg   1320
gtgaaaaacc cgttcgccgg aagaccaagg gttcctgtcc aacgttaatc ggggcagggt   1380
gagtcggccc ctaaggcgag gctgaagagc gtagtcgatg ggaaacgggt taatattccc   1440
gtacttgtta taattgcgat gtggggacgg agtaggttag gttatcgacc tgttggaaaa   1500
ggtcgtttaa gttggtaggt ggagcgttta ggcaaatccg gacgcttatc aacaccgaga   1560
gatgatgacg aggcgctaag gtgccgaagt aaccgatacc acacttccag gaaaagccac   1620
taagcgtcag attataataa accgtactat aaaccgacac aggtggtcag gtagagaata   1680
ctcaggcgct tgagagaact cgggtgaagg aactaggcaa aatagcaccg taacttcggg   1740
agaaggtgcg ccggcgtaga ttgtagaggt ataccttga aggttgaacc ggtcgaagtg   1800
acccgctggc tgcaactgtt tattaaaaac acagcactct gcaaacacga agtggacgt   1860 ataggtgtg atgcctgccc ggtgctggaa ggttaattga tggcgttatc gcaagagaag   1920
cgcctgatcg aagccccagt aaacggcggc cgtaactata acggtcctaa ggtagcgaaa   1980
ttccttgtcg ggtaagttcc gacctgcacg aatggcataa tgatggccag gctgtctcca   2040
cccgagactc agtgaaattg aaatcgccgt gaagatgcgg tgtacccgcg gctagacgga   2100
aagaccccgt gaacctttac tatagcttga cactgaacct tgaattttga tgtgtaggat   2160
aggtgggagg ctttgaagcg gtaacgccag ttatcgtgga gccatccttg aaataccacc   2220
ctttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa   2340
tgacggtcgg acatcgtcag gttagtgcaa tggtataagc aagcttaact gcgagacgga   2400
caagtcgagc aggtgcgaaa gcaggtcata gtgatccggt ggttctgaat ggaagggcca   2460
tcgctcaacg gataaaaggt actccgggga taacaggctg ataccgccca agagttcata   2520
tcgacggcgg tgtttggcac ctcgatgtcg gctcatcaca tcctggggct gaagtaggtc   2580
ccaagggtat ggctgttcgc catttaaagt ggtacgcgag ctgggtttaa aacgtcgtga   2640
gacagtttgg tccctatctg ccgtgggcgt tggagaattg agaggggctg ctcctagtac   2700
gagaggaccg gagtggacgc atcactggtg ttccggttgt gtcgccagac gcattgccgg   2760
gtagctacat gcggaagaga taagtgctga aagcatctaa gcacgaaact tgcctcgaga   2820
tgagttctcc cagtatttaa tactgtaagg gttgttggag acgacgacgt agataggccg   2880
ggtgtgtaag cgttgcgaga cgttgagcta accggtacta attgcccgag aggcttagcc   2940
atacaacgct caagtgtttt tggtagtgaa agttattacg gaataagtaa gtagtcaggg   3000
aatcggct                                                            3008
```

<210> SEQ ID NO 3
<211> LENGTH: 600
<212> TYPE: DNA
<213> ORGANISM: Basfia succiniciproducens
<220> FEATURE:
<221> NAME/KEY: MISC_FEATURE
<223> OTHER INFORMATION: nucleotide sequence of wcaJ-gene from strain
      DD1

<400> SEQUENCE: 3
atgataaaac gccttttcga tattgttgtc gcattgatag cattgatttt gttttcgccc    60
ttatatttgt ttgtggctta taaggtaaaa caaaatttgg gatcaccggt gttatttaaa   120
caaacccgcc ccggattgca tggtaaaccc tttgagatga ttaagttcag aacaatgaaa   180
gacggcgcag atgaaaacgg taatattttg ccggatgcgg agcgcttaac acctttcggc   240
aaaatgttgc gcgctaccag tctggacgag ttgccggaac tttggaatgt attaaaaggt   300
gatatgagtc tggtggggcc gcgtcctcta ctgatggaat atttgccgct gtataacgaa   360
agacaggcta agcgccatga agtgaaaccc ggaattaccg gttatgcaca ggtaaacggt   420
cgcaatgcca tcagttggga gcagaaattt gaattggatg cctggtatgt tgaacatcaa   480
tccttgtggc tggatttgaa aattatcgca aagaccatcc aaaaagtgat cgcaaaagac   540
gatattaatg cggcagatga tgccaccatg cctaaatttg aagggaataa aaaatcatga   600

<210> SEQ ID NO 4
<211> LENGTH: 199
<212> TYPE: PRT
<213> ORGANISM: Basfia succiniciproducens
<220> FEATURE:
<221> NAME/KEY: MISC_FEATURE
<223> OTHER INFORMATION: amino acid sequence of the enzyme encoded by
      the wcaJ-gene

<400> SEQUENCE: 4

Met Ile Lys Arg Leu Phe Asp Ile Val Val Ala Leu Ile Ala Leu Ile
1               5                   10                  15

Leu Phe Ser Pro Leu Tyr Leu Phe Val Ala Tyr Lys Val Lys Gln Asn
            20                  25                  30

Leu Gly Ser Pro Val Leu Phe Lys Gln Thr Arg Pro Gly Leu His Gly
        35                  40                  45

Lys Pro Phe Glu Met Ile Lys Phe Arg Thr Met Lys Asp Gly Ala Asp
    50                  55                  60

Glu Asn Gly Asn Ile Leu Pro Asp Ala Glu Arg Leu Thr Pro Phe Gly
65                  70                  75                  80

Lys Met Leu Arg Ala Thr Ser Leu Asp Glu Leu Pro Glu Leu Trp Asn
                85                  90                  95

Val Leu Lys Gly Asp Met Ser Leu Val Gly Pro Arg Pro Leu Leu Met
            100                 105                 110

Glu Tyr Leu Pro Leu Tyr Asn Glu Arg Gln Ala Lys Arg His Glu Val
        115                 120                 125

Lys Pro Gly Ile Thr Gly Tyr Ala Gln Val Asn Gly Arg Asn Ala Ile
    130                 135                 140

Ser Trp Glu Gln Lys Phe Glu Leu Asp Ala Trp Tyr Val Glu His Gln
145                 150                 155                 160

Ser Leu Trp Leu Asp Leu Lys Ile Ile Ala Lys Thr Ile Gln Lys Val
                165                 170                 175

Ile Ala Lys Asp Asp Ile Asn Ala Ala Asp Asp Ala Thr Met Pro Lys
            180                 185                 190

Phe Glu Gly Asn Lys Lys Ser
        195

<210> SEQ ID NO 5
<211> LENGTH: 4285

<212> TYPE: DNA
<213> ORGANISM: artificial sequence
<220> FEATURE:
<223> OTHER INFORMATION: complete nucleotide sequence of plasmid pSacB

<400> SEQUENCE: 5

| | | | | | |
|---|---|---|---|---|---|
| tcgagaggcc | tgacgtcggg | cccggtacca | cgcgtcatat | gactagttcg | gacctaggga | 60 |
| tatcgtcgac | atcgatgctc | ttctgcgtta | attaacaatt | gggatcctct | agactccata | 120 |
| ggccgctttc | ctggctttgc | ttccagatgt | atgctctcct | ccggagagta | ccgtgacttt | 180 |
| attttcggca | caaatacagg | ggtcgatgga | taaatacggc | gatagtttcc | tgacggatga | 240 |
| tccgtatgta | ccggcggaag | acaagctgca | aacctgtcag | atggagattg | atttaatggc | 300 |
| ggatgtgctg | agagcaccgc | cccgtgaatc | cgcagaactg | atccgctatg | tgtttgcgga | 360 |
| tgattggccg | gaataaataa | agcccggctt | aatacagatt | aagcccgtat | agggtattat | 420 |
| tactgaatac | caaacagctt | acggaggacg | gaatgttacc | cattgagaca | accagactgc | 480 |
| cttctgatta | ttaatatttt | tcactattaa | tcagaaggaa | taaccatgaa | ttttacccgg | 540 |
| attgacctga | atacctggaa | tcgcagggaa | cactttgccc | tttatcgtca | gcagattaaa | 600 |
| tgcggattca | gcctgaccac | caaactcgat | attaccgctt | tgcgtaccgc | actggcggag | 660 |
| acaggttata | agttttatcc | gctgatgatt | tacctgatct | cccgggctgt | taatcagttt | 720 |
| ccggagttcc | ggatggcact | gaaagacaat | gaacttattt | actgggacca | gtcagacccg | 780 |
| gtctttactg | tctttcataa | agaaaccgaa | acattctctg | cactgtcctg | ccgttatttt | 840 |
| ccggatctca | gtgagtttat | ggcaggttat | aatgcggtaa | cggcagaata | tcagcatgat | 900 |
| accagattgt | tccgcaggg | aaatttaccg | gagaatcacc | tgaatatatc | atcattaccg | 960 |
| tgggtgagtt | ttgacgggat | ttaacctgaa | catcaccgga | aatgatgatt | attttgcccc | 1020 |
| ggtttttacg | atggcaaagt | ttcagcagga | aggtgaccgc | gtattattac | ctgtttctgt | 1080 |
| acaggttcat | catgcagtct | gtgatggctt | tcatgcagca | cggtttatta | atacacttca | 1140 |
| gctgatgtgt | gataacatac | tgaaataaat | taattaattc | tgtatttaag | ccaccgtatc | 1200 |
| cggcaggaat | ggtggctttt | tttttatatt | ttaaccgtaa | tctgtaattt | cgtttcagac | 1260 |
| tggttcagga | tgagctcgct | tggactcctg | ttgatagatc | cagtaatgac | ctcagaactc | 1320 |
| catctggatt | tgttcagaac | gctcggttgc | cgccgggcgt | tttttattgg | tgagaatcca | 1380 |
| agcactagcg | gcgcgccggc | cggcccggtg | tgaaataccg | cacagatgcg | taaggagaaa | 1440 |
| ataccgcatc | aggcgctctt | ccgcttcctc | gctcactgac | tcgctgcgct | cggtcgttcg | 1500 |
| gctgcggcga | gcggtatcag | ctcactcaaa | ggcggtaata | cggttatcca | cagaatcagg | 1560 |
| ggataacgca | ggaaagaaca | tgtgagcaaa | aggccagcaa | aaggccagga | accgtaaaaa | 1620 |
| ggccgcgttg | ctggcgtttt | tccataggct | ccgcccccct | gacgagcatc | acaaaaatcg | 1680 |
| acgctcaagt | cagaggtggc | gaaacccgac | aggactataa | agataccagg | cgtttccccc | 1740 |
| tggaagctcc | ctcgtgcgct | ctcctgttcc | gaccctgccg | cttaccggat | acctgtccgc | 1800 |
| ctttctccct | tcgggaagcg | tggcgctttc | tcatagctca | cgctgtaggt | atctcagttc | 1860 |
| ggtgtaggtc | gttcgctcca | agctgggctg | tgtgcacgaa | ccccccgttc | agcccgaccg | 1920 |
| ctgcgcctta | tccggtaact | atcgtcttga | gtccaacccg | gtaagacacg | acttatcgcc | 1980 |
| actggcagca | gccactggta | acaggattag | cagagcgagg | tatgtaggcg | gtgctacaga | 2040 |
| gttcttgaag | tggtggccta | actacggcta | cactagaagg | acagtatttg | gtatctgcgc | 2100 |
| tctgctgaag | ccagttacct | tcggaaaaag | agttggtagc | tcttgatccg | gcaaacaaac | 2160 |

```
caccgctggt agcggtggtt tttttgtttg caagcagcag attacgcgca gaaaaaaagg    2220
atctcaagaa gatcctttga tcttttctac ggggtctgac gctcagtgga acgaaaactc    2280
acgttaaggg attttggtca tgagattatc aaaaaggatc ttcacctaga tccttttaaa    2340
ggccggccgc ggccgccatc ggcattttct tttgcgtttt tatttgttaa ctgttaattg    2400
tccttgttca aggatgctgt cttttgacaac agatgttttc ttgcctttga tgttcagcag    2460
gaagctcggc gcaaacgttg attgtttgtc tgcgtagaat cctctgtttg tcatatagct    2520
tgtaatcacg acattgtttc ctttcgcttg aggtacagcg aagtgtgagt aagtaaaggt    2580
tacatcgtta ggatcaagat ccatttttaa cacaaggcca gttttgttca gcggcttgta    2640
tgggccagtt aaagaattag aaacataacc aagcatgtaa atatcgttag acgtaatgcc    2700
gtcaatcgtc attttgatc cgcgggagtc agtgaacagg taccatttgc cgttcatttt    2760
aaagacgttc gcgcgttcaa tttcatctgt tactgtgtta gatgcaatca gcggtttcat    2820
cacttttttc agtgtgtaat catcgtttag ctcaatcata ccgagagcgc cgtttgctaa    2880
ctcagccgtg cgttttttat cgctttgcag aagttttga ctttcttgac ggaagaatga    2940
tgtgcttttg ccatagtatg ctttgttaaa taaagattct tcgccttggt agccatcttc    3000
agttccagtg tttgcttcaa atactaagta tttgtggcct ttatcttcta cgtagtgagg    3060
atctctcagc gtatggttgt cgcctgagct gtagttgcct tcatcgatga actgctgtac    3120
attttgatac gttttccgt caccgtcaaa gattgattta taatcctcta caccgttgat    3180
gttcaaagag ctgtctgatg ctgatacgtt aacttgtgca gttgtcagtg tttgtttgcc    3240
gtaatgttta ccggagaaat cagtgtagaa taaacggatt tttccgtcag atgtaaatgt    3300
ggctgaacct gaccattctt gtgtttggtc ttttaggata gaatcatttg catcgaattt    3360
gtcgctgtct ttaaagacgc ggccagcgtt tttccagctg tcaatagaag tttcgccgac    3420
tttttgatag aacatgtaaa tcgatgtgtc atccgcatt ttaggatctc cggctaatgc    3480
aaagacgatg tggtagccgt gatagtttgc gacagtgccg tcagcgtttt gtaatggcca    3540
gctgtcccaa acgtccaggc cttttgcaga agagatattt ttaattgtgg acgaatcaaa    3600
ttcagaaact tgatatttt cattttttg ctgttcaggg atttgcagca tatcatggcg    3660
tgtaatatgg gaaatgccgt atgtttcctt atatggcttt tggttcgttt ctttcgcaaa    3720
cgcttgagtt gcgcctcctg ccagcagtgc ggtagtaaag gttaatactg ttgcttgttt    3780
tgcaaacttt ttgatgttca tcgttcatgt ctccttttt atgtactgtg ttagcggtct    3840
gcttcttcca gccctcctgt ttgaagatgg caagttagtc acgcacaata aaaaagacc    3900 taaaatatgt aagggtgac gccaaagtat acactttgcc ctttacacat tttaggtctt    3960
gcctgcttta tcagtaacaa acccgcgcga tttactttc gacctcattc tattagactc    4020
tcgtttggat tgcaactggt ctatttttcct cttttgtttg atagaaaatc ataaaggat    4080 ttgcagacta cgggcctaaa gaactaaaaa atctatctgt ttcttttcat tctctgtatt    4140
ttttatagtt tctgttgcat gggcataaag ttgccttttt aatcacaatt cagaaaatat    4200
cataatatct catttcacta aataatagtg aacggcaggt atatgtgatg ggttaaaaag    4260
gatcggcggc cgctcgattt aaatc                                          4285

<210> SEQ ID NO 6
<211> LENGTH: 7074
<212> TYPE: DNA
<213> ORGANISM: artificial sequence
<220> FEATURE:
<223> OTHER INFORMATION: complete nucleotide sequence of plasmid
``` pSacB_delta_ldhA

<400> SEQUENCE: 6

```
tcgagaggcc tgacgtcggg cccggtacca cgcgtcatat gactagttcg gacctaggga      60
tgggtcagcc tgaacgaacc gcacttgtat gtaggtagtt ttgaccgccc gaatattcgt     120
tataccttgg tggaaaaatt caaaccgatg gagcaattat acaattttgt ggcggcgcaa     180
aaaggtaaaa gcggtatcgt ctattgcaac agccgtagca aagtggagcg cattgcggaa     240
gccctgaaga aaagaggcat tccgcagcc gcttatcatg cgggcatgga gccgtcgcag      300
cgggaagcgg tgcaacaggc gtttcaacgg gataatattc aagtggtggt ggcgaccatt     360
gcttttggta tggggatcaa caaatctaat gtgcgttttg tggcgcattt tgatttatct     420
cgcagcattg aggcgtatta tcaggaaacc gggcgcgcgg ggcgggacga cctgccggcg     480
gaagcggtac tgttttacga gccggcggat tatgcctggt tgcataaaat tttattggaa     540
gagccggaaa gcccgcaacg ggatattaaa cggcataagc tggaagccat cggcgaattt     600
gccgaaagcc agacctgccg tcgtttagtg ctgttaaatt atttcggcga aaaccgccaa     660
acgccatgta ataactgtga tatctgcctc gatccgccga aaaatatga cggattatta      720
gacgcgcaga aaatcctttc gaccatttat cgcaccgggc aacgtttcgg cacgcaatac     780
gtaatcggcg taatgcgcgg tttgcagaat cagaaaataa agaaaatca acatgatgag      840
ttgaaagtct acggaattgg caaagataaa agcaaagaat actggcaatc ggtaattcgt     900
cagctgattc atttgggctt tgtgcaacaa atcatcagcg atttcggcat ggggaccaga     960
ttacagctca ccgaaagcgc gcgtcccgtg ctgcgcggcg aagtgtcttt ggaactggcc    1020
atgccgagat tatcttccat taccatggta caggctccgc aacgcaatgc ggtaaccaac    1080
tacgacaaag atttatttgc ccgcctgcgt ttcctgcgca aacagattgc cgacaaagaa    1140
acattccgc cttatattgt gttcagtgac gcgaccttgc aggaaatgtc gttgtatcag     1200
ccgaccagca aagtggaaat gctgcaaatc aacggtgtcg cgccatcaa atggcagcgc     1260
tcggacagc ctttttatggc gattattaaa gaacatcagg ctttgcgtaa agcgggtaag    1320
aatccgttgg aattgcaatc ttaaaatttt taacttttg accgcacttt taaggttagc     1380
aaattccaat aaaaagtgcg gtgggttttc gggaattttt aacgcgctga tttcctcgtc    1440
ttttcaattt yttcgyctcc atttgttcgg yggttgccgg atcctttctt gactgagatc    1500
cataagagag tagaatagcg ccgcttatat ttttaatagc gtacctaatc gggtacgctt    1560
tttttatgcg gaaatccat attttttctac cgcactttt ctttaaagat ttatacttaa     1620
gtctgtttga ttcaattat ttggaggttt tatgcaacac attcaactgg ctcccgattt     1680
aacattcagt cgcttaattc aaggattctg gcggttaaaa agctggcgga atcgccgca     1740
ggaattgctt acattcgtta agcaaggatt agaattaggc gttgatacgc tggatcatgc    1800
cgcttgttac ggggcttta cttccgaggc ggaattcgga cgggcgctgg cgctggataa    1860
atccttgcgc gcacagctta cttttggtgac caaatgcggg attttgtatc ctaatgaaga    1920
attacccgat ataaaatccc atcactatga caacagctac cgccatatta tgtggtcggc    1980
gcaacgttcc attgaaaaac tgcaatgcga ctatttagat gtattgctga ttcaccgwct    2040
ttctccctgt gcggatcccg aacaaatcgc gcgggctttt gatgaacttt atcaaaccgg    2100
raaagtacgt tatttcgggg tatctaacta tacgccggct aagttcgcca tgttgcaatc    2160
ttatgtgaat cagccgttaa tcactaatca aattgagatt tcgcctcttc atcgtcaggc    2220
ttttgatgac ggtaccctgg atttttact ggaaaaacgt attcaaccga tggcatggtc    2280
```

```
gccacttgcc ggcggtcgtt tattcaatca ggatgagaac agtcgggcgg tgcaaaaaac    2340
attactcgaa atcggtgaaa cgaaaggaga aacccgttta gatacattgg cttatgcctg    2400
gttattggcg catccggcaa aaattatgcc ggttatgggg tccggtaaaa ttgaacgggt    2460
aaaaagcgcg gcggatgcgt tacgaatttc cttcactgag gaagaatgga ttaaggttta    2520
tgttgccgca cagggacggg atattccgta acatcatccg tctaatcctg cgtatctggg    2580
gaaagatgcg tcatcgtaag aggtctataa tattcgtcgt tttgataagg gtgccatatc    2640
cggcacccgt taaaatcaca ttgcgttcgc aacaaaatta ttccttacga atagcattca    2700
cctctttttaa cagatgttga atatccgtat cggcaaaaat atcctctata tttgcggtta    2760
aacggcgccg ccagttagca tattgagtgc tggttcccgg aatattgacg ggttcggtca    2820
taccgagcca gtcttcaggt tggaatcccc atcgtcgaca tcgatgctct tctgcgttaa    2880
ttaacaattg ggatcctcta gactccatag gccgctttcc tggctttgct tccagatgta    2940
tgctctcctc cggagagtac cgtgacttta ttttcggcac aaatacaggg gtcgatggat    3000
aaatacggcg atagtttcct gacggatgat ccgtatgtac cggcggaaga caagctgcaa    3060
acctgtcaga tggagattga tttaatggcg gatgtgctga gagcaccgcc ccgtgaatcc    3120
gcagaactga tccgctatgt gtttgcggat gattggccgg aataaataaa gccgggctta    3180
atacagatta agcccgtata gggtattatt actgaatacc aaacagctta cggaggacgg    3240
aatgttaccc attgagacaa ccagactgcc ttctgattat taatattttt cactattaat    3300
cagaaggaat aaccatgaat tttacccgga ttgacctgaa tacctggaat cgcagggaac    3360
actttgccct ttatcgtcag cagattaaat gcggattcag cctgaccacc aaactcgata    3420
ttaccgcttt gcgtaccgca ctggcggaga caggttataa gttttatccg ctgatgattt    3480
acctgatctc ccgggctgtt aatcagtttc cggagttccg gatggcactg aaagacaatg    3540
aacttattta ctgggaccag tcagacccgg tctttactgt cttcataaa gaaaccgaaa    3600
cattctctgc actgtcctgc cgttattttc cggatctcag tgagtttatg gcaggttata    3660
atgcggtaac ggcagaatat cagcatgata ccagattgtt ccgcagggaa aatttaccgg    3720
agaatcacct gaatatatca tcattaccgt gggtgagttt tgacgggatt taacctgaac    3780
atcaccggaa atgatgatta ttttgccccg gtttttacga tggcaaagtt tcagcaggaa    3840
ggtgaccgcg tattattacc tgtttctgta caggttcatc atgcagtctg tgatggcttt    3900
catgcagcac ggtttattaa tacacttcag ctgatgtgtg ataacatact gaaataaatt    3960
aattaattct gtatttaagc caccgtatcc ggcaggaatg gtggcttttt ttttatattt    4020
taaccgtaat ctgtaatttc gtttcagact ggttcaggat gagctcgctt ggactcctgt    4080
tgatagatcc agtaatgacc tcagaactcc atctggattt gttcagaacg ctcggttgcc    4140
gccgggcgtt ttttattggt gagaatccaa gcactagcgg cgcgccggcc ggcccggtgt    4200
gaaataccgc acagatgcgt aaggagaaaa taccgcatca ggcgctcttc cgcttcctcg    4260
ctcactgact cgctgcgctc ggtcgttcgg ctgcggcgag cggtatcagc tcactcaaag    4320
gcggtaatac ggttatccac agaatcaggg gataacgcag gaaagaacat gtgagcaaaa    4380
ggccagcaaa aggccaggaa ccgtaaaaag gccgcgttgc tggcgttttt ccataggctc    4440
cgcccccctg acgagcatca caaaaatcga cgctcaagtc agaggtggcg aaacccgaca    4500
ggactataaa gataccaggc gtttccccct ggaagctccc tcgtgcgctc tcctgttccg    4560
accctgccgc ttaccggata cctgtccgcc tttctccctt cgggaagcgt ggcgctttct    4620
```

```
catagctcac gctgtaggta tctcagttcg gtgtaggtcg ttcgctccaa gctgggctgt    4680
gtgcacgaac cccccgttca gcccgaccgc tgcgccttat ccggtaacta tcgtcttgag    4740
tccaacccgg taagacacga cttatcgcca ctggcagcag ccactggtaa caggattagc    4800
agagcgaggt atgtaggcgg tgctacagag ttcttgaagt ggtggcctaa ctacggctac    4860
actagaagga cagtatttgg tatctgcgct ctgctgaagc cagttacctt cggaaaaaga    4920
gttggtagct cttgatccgg caaacaaacc accgctggta gcggtggttt ttttgtttgc    4980
aagcagcaga ttacgcgcag aaaaaaagga tctcaagaag atcctttgat cttttctacg    5040
gggtctgacg ctcagtggaa cgaaaactca cgttaaggga ttttggtcat gagattatca    5100
aaaaggatct tcacctagat ccttttaaag gccggccgcg gccgccatcg gcattttctt    5160
ttgcgttttt atttgttaac tgttaattgt ccttgttcaa ggatgctgtc tttgacaaca    5220
gatgttttct tgcctttgat gttcagcagg aagctcggcg caaacgttga ttgtttgtct    5280
gcgtagaatc ctctgtttgt catatagctt gtaatcacga cattgtttcc tttcgcttga    5340
ggtacagcga agtgtgagta agtaaaggtt acatcgttag gatcaagatc cattttaac    5400 acaaggccag ttttgttcag cggcttgtat gggccagtta agaattaga aacataacca    5460 agcatgtaaa tatcgttaga cgtaatgccg tcaatcgtca tttttgatcc gcgggagtca    5520
gtgaacaggt accatttgcc gttcatttta aagacgttcg cgcgttcaat ttcatctgtt    5580
actgtgttag atgcaatcag cggtttcatc acttttttca gtgtgtaatc atcgtttagc    5640
tcaatcatac cgagagcgcc gtttgctaac tcagccgtgc gttttttatc gctttgcaga    5700 agttttgac tttcttgacg gaagaatgat gtgcttttgc catagtatgc tttgttaaat    5760
aaagattctt cgccttggta gccatcttca gttccagtgt tgcttcaaa tactaagtat    5820 ttgtggcctt tatcttctac gtagtgagga tctctcagcg tatggttgtc gcctgagctg    5880
tagttgcctt catcgatgaa ctgctgtaca ttttgatacg ttttccgtc accgtcaaag    5940 attgatttat aatcctctac accgttgatg ttcaaagagc tgtctgatgc tgatacgtta    6000
acttgtgcag ttgtcagtgt tgtttgccg taatgtttac cggagaaatc agtgtagaat    6060
aaacggattt ttccgtcaga tgtaaatgtg gctgaacctg accattcttg tgtttggtct    6120
tttaggatag aatcatttgc atcgaatttg tcgctgtctt taaagacgcg gccagcgttt    6180
ttccagctgt caatagaagt ttcgccgact ttttgataga acatgtaaat cgatgtgtca    6240
tccgcatttt taggatctcc ggctaatgca aagacgatgt ggtagccgtg atagtttgcg    6300
acagtgccgt cagcgttttg taatggccag ctgtcccaaa cgtccaggcc ttttgcagaa    6360
gagatatttt taattgtgga cgaatcaaat tcagaaactt gatattttc attttttgc     6420 tgttcaggga tttgcagcat atcatggcgt gtaatatggg aaatgccgta tgtttcctta    6480
tatggctttt ggttcgtttc tttcgcaaac gcttgagttg cgcctcctgc cagcagtgcg    6540
gtagtaaagg ttaatactgt tgcttgtttt gcaaactttt tgatgttcat cgttcatgtc    6600 tccttttta tgtactgtgt tagcggtctg cttcttccag ccctcctgtt tgaagatggc    6660
aagttagtta cgcacaataa aaaagacct aaatatgta aggggtgacg ccaaagtata    6720
cactttgccc tttacacatt ttaggtcttg cctgctttat cagtaacaaa cccgcgcgat    6780
ttacttttcg acctcattct attagactct cgtttggatt gcaactggtc tattttcctc    6840
ttttgtttga tagaaaatca taaaaggatt tgcagactac gggcctaaag aactaaaaaa    6900
tctatctgtt tcttttcatt ctctgtattt tttatagttt ctgttgcatg gcataaagt    6960 tgccttttta atcacaattc agaaaatatc ataatatctc atttcactaa ataatagtga    7020
```

| | |
|---|---:|
| acggcaggta tatgtgatgg gttaaaaagg atcggcggcc gctcgattta aatc | 7074 |

<210> SEQ ID NO 7
<211> LENGTH: 7183
<212> TYPE: DNA
<213> ORGANISM: artificial sequence
<220> FEATURE:
<223> OTHER INFORMATION: complete nucleotide sequence of plasmid pSacB_delta_pflA

<400> SEQUENCE: 7

| | |
|---|---:|
| tcgagtcaat gcggatttga cttatgatgt ggcaaacaac cgatttccga ttattactac | 60 |
| acgtaaaagt tattggaaag cggcgattgc ggagtttctg ggttatatcc gcggctacga | 120 |
| taatgcggcg gatttccgta aattaggagc aaaaacctgg gatgccaacg ctaatgaaaa | 180 |
| tcaggtatgg ctgaataacc ctcatcgcaa aggcaccgac gacatggggc gcgtttacgg | 240 |
| cgtacagggc agagcctggc gtaagcctaa cggcgaaacc gttgatcaat tacgcaaaat | 300 |
| tgtcaacaat ttaagtcgcg gcattgatga tcgcggcgaa attctgacct ttttaaaccc | 360 |
| gggcgaattc gatctcggtt gtctgcgccc ttgtatgtac aatcacacgt tttctttgct | 420 |
| gggcgatacg ctttatttaa ccagttatca acgctcctgt gacgtacctt taggcttgaa | 480 |
| tttcaatcaa attcaagtat ttacattctt agctttaatg gcgcagatta ccggtaaaaa | 540 |
| agccggtcag gcatatcaca aaatcgtcaa tgcgcatatt tacgaagacc agctggaact | 600 |
| aatgcgcgac gtgcagttaa aacgcgaacc gttcccgtcg ccaaaactgg aaattaatcc | 660 |
| ggacattaaa acccttgaag atttagaaac ctgggtaacc atggatgatt caacgtcgt | 720 |
| tggttaccaa tgccacgaac cgataaaata tccgttctcg gtataaaccg acaaaagtgc | 780 |
| ggtcaaaaat ttaatatttt catctgttat agaaaatatt tttcaacata aatctaggg | 840 |
| atgcctgttt ggcgtccgta aatacgcaga aaatattaa attttgacc gcactttttt | 900 |
| catctcaatt aacagcctga taattcttat ggatcaacaa attagctttg acgaaaaat | 960 |
| gatgaatcga gctcttttcc ttgccgacaa ggcggaagct ttaggggaaa ttcccgtagg | 1020 |
| tgccgtattg gtggatgaac ggggcaatat cattggtgaa ggctggaacc tctctattgt | 1080 |
| gaactcggat cccaccgccc atgccgaaat tattgcgttg cgtaacgccg cgcagaaaat | 1140 |
| ccaaaattac cgcctgctca ataccacttt atacgtgact ttagaaccct gcaccatgtg | 1200 |
| cgccggcgcg attttacaca gccgaatcaa acgcttggta ttcggggcgt ccgattacaa | 1260 |
| aaccggtgcg gtgggttcca gatttcattt ttttgaggat tataaaatga atcatggggt | 1320 |
| tgagatcaca agcggtgtct tacaggatca atgcagtcag aagttaagcc gcttttttcca | 1380 |
| aaagcgcagg gaacagaaaa aacaacaaaa agctaccgca cttttacaac ccccccggct | 1440 |
| taactcctct gaaaaatagt gacaaaaaaa ccgtcataat gtttacgacg gttttttttat | 1500 |
| ttcttaatat gcccttaaat aatcaacaaa atatagcaag aagattatag caaagaattt | 1560 |
| cgttttttc agagaatagt caaatcttcg caaaaaacta ccgcactttt atccgcttta | 1620 |
| atcaggggaa ttaaaacaaa aaaattccgc ctattgaggc ggaatttatt aagcaataag | 1680 |
| acaaactctc aattacattg attgtgtaaa cgtacgagtg atgacgtctt gttgttgctc | 1740 |
| tttagttaat gagttgaaac gaaccgcgta acctgaaaca cgaatggtta attgcgggta | 1800 |
| ttttccgga ttttccatcg cgtctaacaa catttcacgg ttaagaacgt taacattcaa | 1860 |
| gtgttgaccg ccttccactg tcgcttcatg atggaaataa ccgtccatta aaccggcaag | 1920 |
| gttgcgtttt tgcgcttcgt catctttacc taatgcgttc ggtacgatag agaaggtata | 1980 |

```
tgaaataccg tctttcgcgt aagcgaacgg aagtttagcc acagaagtaa gtgaagcaac    2040 cgcaccttt  tggtcacgac cgtgcattgg gtttgcaccc ggtccgaatg gcgcgcctgc    2100
tcgacgaccg tccggagtat taccggtttt cttaccgtat accacgttag aagtgatagt    2160
caggatagat tgtgtcggag ttgcgttgcg gtaagttttg tgttttgaa  cttttttcat    2220 gaaacgttca actaagtcta ccgctaaatc atcaacacgc ggatcattgt taccgaattg    2280
cggatattcg ccttcaattt cgaagtcgat agcaacattc gaggccacga cattaccgtc    2340
tttatctttg atgtcgccgc gaatcggttt aactttcgca tatttgattg cggataatga    2400
gtccgcagcc acgaaaagac ccgcgatacc gcaagccatt gtacggaata cgtcgcgatc    2460
gtggaacgcc atcaatgccg cttcatatgc atatttatcg tgcatgaagt ggatgatgtt    2520
caatgcggtt acatattgag tcgccaacca gtccatgaaa ctgtccatac gttcgattac    2580
ggtatcgaaa ttcaatactt cgtctgtaat cggcgcagtt ttaggaccga cttgcatacc    2640 attttttctca tcgataccgc cgttaattgc gtataacata gttttagcta agtttgcgcg    2700
cgcaccgaag aattgcattt gtttacctac gaccatcggt gatacgcagc atgcgattgc    2760
atagtcatcg ttgttgaagt caggacgcat taagtcatca ttttcgtatt gtacggagga    2820
agtatcaata gatactttcg cacagaaacg tttgaacgct tcaggtaatt gttcggacca    2880
aagaatagtt aagtttggtt ccggagaagt acccatagtg tataaagtat gtaatacgcg    2940
gaagctgttt ttagttacca acggacgacc gtctaagccc ataccggcga tagtttcggt    3000
tgccctctag actccatagg ccgctttcct ggctttgctt ccagatgtat gctctcctcc    3060
ggagagtacc gtgactttat tttcggcaca aatacagggg tcgatggata aatacggcga    3120
tagtttcctg acggatgatc cgtatgtacc ggcggaagac aagctgcaaa cctgtcagat    3180
ggagattgat ttaatggcgg atgtgctgag agcaccgccc cgtgaatccg cagaactgat    3240
ccgctatgtg tttgcggatg attggccgga ataaataaag ccgggcttaa tacagattaa    3300
gcccgtatag ggtattatta ctgaataccaa aacagcttac ggaggacgga atgttaccca    3360
ttgagacaac cagactgcct tctgattatt aatattttc  actattaatc agaaggaata    3420
accatgaatt ttacccggat tgacctgaat acctggaatc gcagggaaca ctttgccctt    3480
tatcgtcagc agattaaatg cggattcagc ctgaccacca aactcgatat taccgctttg    3540
cgtaccgcac tggcggagac aggttataag ttttatccgc tgatgattta cctgatctcc    3600
cgggctgtta atcagtttcc ggagttccgg atggcactga agacaatga  acttatttac    3660 tgggaccagt cagacccggt ctttactgtc tttcataaag aaaccgaaac attctctgca    3720
ctgtcctgcc gttatttttcc ggatctcagt gagtttatgg caggttataa tgcggtaacg    3780
gcagaatatc agcatgatac cagattgttt ccgcagggaa atttaccgga gaatcacctg    3840
aatatatcat cattaccgtg ggtgagtttt gacgggattt aacctgaaca tcaccggaaa    3900
tgatgattat tttgccccgg ttttacgat  ggcaaagttt cagcaggaag gtgaccgcgt    3960
attattacct gtttctgtac aggttcatca tgcagtctgt gatggctttc atgcagcacg    4020
gtttattaat acacttcagc tgatgtgtga taacatactg aaataaatta attaattctg    4080
tatttaagcc accgtatccg gcaggaatgg tggctttttt tttatatttt aaccgtaatc    4140
tgtaatttcg tttcagactg gttcaggatg agctcgcttg gactcctgtt gatagatcca    4200
gtaatgacct cagaactcca tctggatttg ttcagaacgc tcggttgccg ccgggcgttt    4260
tttattggtg agaatccaag cactagcggc gcgccggccg gcccggtgtg aaataccgca    4320
```

```
cagatgcgta aggagaaaat accgcatcag gcgctcttcc gcttcctcgc tcactgactc   4380
gctgcgctcg tcgttcggc tgcggcgagc ggtatcagct cactcaaagg cggtaatacg    4440
gttatccaca gaatcagggg ataacgcagg aaagaacatg tgagcaaaag gccagcaaaa   4500
ggccaggaac cgtaaaaagg ccgcgttgct ggcgtttttc cataggctcc gcccccctga   4560
cgagcatcac aaaaatcgac gctcaagtca gaggtggcga acccgacag gactataaag    4620 ataccaggcg tttccccctg gaagctccct cgtgcgctct cctgttccga ccctgccgct   4680
taccggatac ctgtccgcct ttctcccttc gggaagcgtg gcgctttctc atagctcacg   4740
ctgtaggtat ctcagttcgg tgtaggtcgt tcgctccaag ctgggctgtg tgcacgaacc   4800
ccccgttcag cccgaccgct gcgccttatc cggtaactat cgtcttgagt ccaacccggt   4860
aagacacgac ttatcgccac tggcagcagc cactggtaac aggattagca gagcgaggta   4920
tgtaggcggt gctacagagt tcttgaagtg gtggcctaac tacggctaca ctagaaggac   4980
agtatttggt atctgcgctc tgctgaagcc agttaccttc ggaaaaagag ttggtagctc   5040
ttgatccggc aaacaaacca ccgctggtag cggtggtttt tttgtttgca agcagcagat   5100
tacgcgcaga aaaaaggat ctcaagaaga tcctttgatc ttttctacgg gtctgacgc     5160 tcagtggaac gaaaactcac gttaagggat tttggtcatg agattatcaa aaaggatctt   5220
cacctagatc cttttaaagg ccggccgcgg ccgccatcgg catttttcttt tgcgttttta   5280 tttgttaact gttaattgtc cttgttcaag gatgctgtct ttgacaacag atgttttctt   5340
gcctttgatg ttcagcagga agctcggcgc aaacgttgat tgtttgtctg cgtagaatcc   5400
tctgtttgtc atatagcttg taatcacgac attgttcctt tcgcttgag gtacagcgaa    5460 gtgtgagtaa gtaaaggtta catcgttagg atcaagatcc attttttaaca caaggccagt   5520 tttgttcagc ggcttgtatg ggccagttaa agaattagaa acataaccaa gcatgtaaat   5580
atcgttagac gtaatgccgt caatcgtcat ttttgatccg cgggagtcag tgaacaggta   5640
ccatttgccg ttcattttaa agacgttcgc gcgttcaatt tcatctgtta ctgtgttaga   5700
tgcaatcagc ggtttcatca cttttttcag tgtgtaatca tcgtttagct caatcatacc   5760
gagagcgccg tttgctaact cagccgtgcg tttttttatcg ctttgcagaa gttttttgact  5820 ttcttgacgg aagaatgatg tgcttttgcc atagtatgct ttgttaaata aagattcttc   5880
gccttggtag ccatcttcag ttccagtgtt tgcttcaaat actaagtatt tgtggccttt   5940
atcttctacg tagtgaggat ctctcagcgt atggttgtcg cctgagctgt agttgccttc   6000
atcgatgaac tgctgtacat tttgatacgt ttttccgtca ccgtcaaaga ttgatttata   6060
atcctctaca ccgttgatgt tcaaagagct gtctgatgct gatacgttaa cttgtgcagt   6120
tgtcagtgtt tgtttgccgt aatgtttacc ggagaaatca gtgtagaata aacggatttt   6180
tccgtcagat gtaaatgtgg ctgaacctga ccattcttgt gtttggtctt ttaggataga   6240
atcatttgca tcgaatttgt cgctgtcttt aaagacgcgg ccagcgtttt tccagctgtc   6300
aatagaagtt tcgccgactt tttgatagaa catgtaaatc gatgtgtcat ccgcattttt   6360
aggatctccg gctaatgcaa agacgatgtg gtagccgtga tagtttgcga cagtgccgtc   6420
agcgttttgt aatggccagc tgtcccaaac gtccaggcct tttgcagaag atattttttt  6480
aattgtggac gaatcaaatt cagaaacttg atatttttca tttttttgct gttcagggat   6540
ttgcagcata tcatggcgtg taatatggga aatgccgtat gtttcctttat atggcttttg   6600 gttcgtttct ttcgcaaacg cttgagttgc gcctcctgcc agcagtgcgg tagtaaaggt   6660
taatactgtt gcttgttttg caaacttttt gatgttcatc gttcatgtct cctttttttat  6720
```

```
gtactgtgtt agcggtctgc ttcttccagc cctcctgttt gaagatggca agttagttac    6780
gcacaataaa aaaagaccta aaatatgtaa ggggtgacgc caaagtatac actttgccct    6840
ttacacattt taggtcttgc ctgctttatc agtaacaaac ccgcgcgatt tacttttcga    6900
cctcattcta ttagactctc gtttggattg caactggtct attttcctct tttgtttgat    6960
agaaaatcat aaaaggattt gcagactacg ggcctaaaga actaaaaaat ctatctgttt    7020
cttttcattc tctgtatttt ttatagtttc tgttgcatgg gcataaagtt gccttttaa     7080 tcacaattca gaaatatca  taatatctca tttcactaaa taatagtgaa cggcaggtat    7140
atgtgatggg ttaaaaagga tcggcggccg ctcgatttaa atc                      7183
```

<210> SEQ ID NO 8
<211> LENGTH: 7300
<212> TYPE: DNA
<213> ORGANISM: artificial sequence
<220> FEATURE:
<223> OTHER INFORMATION: complete nucleotide sequence of plasmid pSacB_wcaJ

<400> SEQUENCE: 8

```
tcgagtaagc cgattcagct gatccgccac atggggaaaa agcctaatct gcggaatatg      60
aaaccgatac cagtccagta aagttgacaa atcgacatca tattgctcaa ccaagtattg     120
aaaagcgttt tcaccgcgat gatacaattc gaccagccgg ttaaataacg tttcactccg     180
ttccggtgcc aaacgagacg caatatgctt ataggcggaa tacagaaaat cgatttccgc     240
ataaagcgta tcgtccaaat ctaaaaccaa cgctttattt ttcataatga tgagccagta     300
cttccgcgtc ataccgcaac attaataaat ccgcttccca gtcttcgaac gcaggaatcg     360
gctgattaaa caaatattcc tgaatcaacc aacggggata attggctccc gccagataac     420
tcaacggata accgccgccg aacctagggt taatttcaat accaagaatt tcagcggtgg     480
attccttata aaatacttgg attgttaagc aaccgcgcgc ccccggtaaa cgggacaatt     540
tttccgataa ttgcgtcacg atggcatttt ttctggtcac acctttgtta atttcccccg     600
ctctgacaaa aattctcttt ctcggtaccg cacttttcag ttcggaattt ttatcaaaat     660
aacaatccac ggtatattcg tcgtattccg ccggcgaaat atattgcata acattaatt      720 cgggattttc caattgctcc ggtgaaatat cttccggttt ctccgccaca aaaattcctt     780
tacttaaact accgttgtaa ggcttcacaa aaacaggata ttcaaattga ccttttttcaa    840 actgcttcgg taccgcaata ttatgttcaa taaacagttg attggttaat cgtttgtcgc     900
gacattttct gacaaactct gtatcactaa cggaaataaa aatacctttt tctttaaacc     960
gttgcagatg ttcgcttaaa ataagcaatt ccgtatcaat agtcggaata atcaatttca    1020
cgttattttc ttcacagatt ttaagtaagg tcggaatata ctccgcatca gtgacccggg    1080
gtacaggaaa atgtccgtcg gccacataac aagccggcgc caactcggga tttaaatcta    1140
cggttaacac ttttccgtca cttactaact gcgataattc cttttttaaac gcctgaacga    1200 gagaaacacg ttgtccggcc gatgtaacaa gaatattcat gatttttttat tcccttcaaa    1260 tttaggcatg gtggcatcat ctgccgcatt aatatcgtct tttgcgatca cttttttggat    1320 ggtctttgcg ataatttttca aatccagcca caaggattga tgttcaacat accaggcatc    1380
caattcaaat ttctgctccc aactgatggc attgcgaccg tttacctgtg cataaccggt    1440
aattccgggt tcacttcat ggcgcttagc ctgtctttcg ttatacagcg gcaaatattc     1500
catcacacaa acaaatataa gggcgaaaac aaaatcaatg ctatcaatgc gacaacaata    1560
```

```
tcgaaaaggc gttttatcat gaaaatctcc tacgaccgac caatttgggg ctgacaaaag    1620
tgccgttttt caccagaacc gtataaacta aaaccaggaa aagcggatac cagactaacg    1680
gcagtcttaa tatggaagac ggcacccaaa cgatccaaca aaaattaata aaaataaata    1740
aaataaatat acgttctttc cacgccaaca attgggtatt catcacatag ataattgaat    1800
ttaataaaaa atatataaat gccaaaaatg caaaaatgcc aaatgccaaa taaagttcta    1860
taaagaagct atgcggatta gtgtaaccca aagggaaact taactttatt tgatcgaaat    1920
actgaatgta gtcccgcggt ccataaccca accataaaat tttaaaatta tctaaaaatg    1980
tcgtataaat ttccgtccgg taacctacgg acttatcatc gcccatagaa aatattacca    2040
atgaaaaacg ttcaatcgga cgctccagcc aatcaatttt ggcgagcaga ataaacactt    2100
cctgtaacca agaaagatta aatataaata atgcgatcac gcaggcgaaa aacagatata    2160
ccgccttaaa ataggtagat gcgtttaaaa acaagatcag catcaacata atcaaatagc    2220 tcagtaaatac cgaacgggag gcactgatca caatagctaa ccccataata aaaataagag    2280
catagccgat taacttaatt ttccagttgt tttctctgat gatgtaaaaa aatcccaccg    2340
ccaccgcaag agaaatcata attacggact ggtcattggt attaaagaaa aaacctttaa    2400
acgccttatc agttacggtt aattcttcat tacccgaaac caactggaac cccaataaag    2460
cctcaataaa aaagcccgcc agcacaatta atgatattcc caacaaaagg tgcctaatcc    2520
ctgcttctcc atcaccccgg ttaaacgtca aaaagaata atgaaataaa aacatcacaa    2580
ttccgaagaa aaacaaatca actaattttt ctgtagaaaa cgcatttaat accgataaaa    2640
agccgaagaa aaacaacacg tacaccggaa actgtaattt aaaaaaatca gtttccatat    2700
cccttaaaaa aggggttatt accgctaaga aaaagaacaa aaaacacaac gcactatcta    2760
acctcggcac tcctatttgt gtcgatagtg cgggagaaag tatcaccagt cccaacgcaa    2820
agagtaatag caacttaaaa atgctgataa cattaatatt catatcaaat aatattttg    2880 attaatttct caatttcttt ataagaacgc tcgcgcagaa acttctcttt tgccagcgat    2940
aaattcactt gcgacatttt gtctaaaacc gttctgtctt cggccaattt attcaacgtc    3000
tcagccaact cccgataatc tcccgccgta tattgaattc caccgccttt cgccagtagt    3060
ttttccactt caggatgttt ctgacagctt acaatcggta atgcgcaaca gatataatcg    3120
gatctagact ccataggccg ctttcctggc tttgcttcca gatgtatgct ctcctccgga    3180
gagtaccgtg actttatttt cggcacaaat acaggggtcg atggataaat acggcgatag    3240
tttcctgacg gatgatccgt atgtaccggc ggaagacaag ctgcaaacct gtcagatgga    3300
gattgattta atggcggatg tgctgagagc accgccccgt gaatccgcag aactgatccg    3360
ctatgtgttt gcgatgatt ggccggaata aataaagccg gcttaatac agattaagcc    3420 cgtatagggt attattactg aataccaaac agcttacgga ggacggaatg ttacccattg    3480
agacaaccag actgccttct gattattaat atttttcact attaatcaga aggaataacc    3540 atgaattta cccggattga cctgaatacc tggaatcgca gggaacactt tgcccttat    3600 cgtcagcaga ttaaatgcgg attcagcctg accaccaaac tcgatattac cgctttgcgt    3660
accgcactgg cggagacagg ttataagttt tatccgctga tgatttacct gatctcccgg    3720
gctgttaatc agtttccgga gttccggatg gcactgaaag acaatgaact tatttactgg    3780
gaccagtcag acccggtctt tactgtcttt cataaagaaa ccgaaacatt ctctgcactg    3840
tcctgccgtt attttccgga tctcagtgag tttatggcag gttataatgc ggtaacggca    3900
```

```
gaatatcagc atgataccag attgtttccg cagggaaatt taccggagaa tcacctgaat    3960
atatcatcat taccgtgggt gagttttgac gggatttaac ctgaacatca ccggaaatga    4020
tgattatttt gccccggttt ttacgatggc aaagtttcag caggaaggtg accgcgtatt    4080
attacctgtt tctgtacagg ttcatcatgc agtctgtgat ggctttcatg cagcacggtt    4140
tattaataca cttcagctga tgtgtgataa catactgaaa taaattaatt aattctgtat    4200
ttaagccacc gtatccggca ggaatggtgg ctttttttt atattttaac cgtaatctgt      4260
aatttcgttt cagactggtt caggatgagc tcgcttggac tcctgttgat agatccagta    4320
atgacctcag aactccatct ggatttgttc agaacgctcg gttgccgccg ggcgtttttt    4380
attggtgaga atccaagcac tagcggcgcg ccggccggcc cggtgtgaaa taccgcacag    4440
atgcgtaagg agaaaatacc gcatcaggcg ctcttccgct tcctcgctca ctgactcgct    4500
gcgctcggtc gttcggctgc ggcgagcggt atcagctcac tcaaaggcgg taatacggtt    4560
atccacagaa tcaggggata acgcaggaaa gaacatgtga gcaaaaggcc agcaaaaggc    4620
caggaaccgt aaaaaggccg cgttgctggc gtttttccat aggctccgcc cccctgacga    4680
gcatcacaaa aatcgacgct caagtcagag gtggcgaaac ccgacaggac tataaagata    4740
ccaggcgttt ccccctggaa gctccctcgt gcgctctcct gttccgaccc tgccgcttac    4800
cggatacctg tccgcctttc tcccttcggg aagcgtggcg ctttctcata gctcacgctg    4860
taggtatctc agttcggtgt aggtcgttcg ctccaagctg ggctgtgtgc acgaaccccc    4920
cgttcagccc gaccgctgcg ccttatccgg taactatcgt cttgagtcca acccggtaag    4980
acacgactta tcgccactgg cagcagccac tggtaacagg attagcagag cgaggtatgt    5040
aggcggtgct acagagttct tgaagtggtg gcctaactac ggctacacta aaggacagt     5100 atttggtatc tgcgctctgc tgaagccagt taccttcgga aaaagagttg gtagctcttg    5160
atccggcaaa caaaccaccg ctggtagcgg tggtttttt gtttgcaagc agcagattac      5220
gcgcagaaaa aaaggatctc aagaagatcc tttgatcttt tctacggggt ctgacgctca    5280
gtggaacgaa aactcacgtt aagggatttt ggtcatgaga ttatcaaaaa ggatcttcac    5340
ctagatcctt ttaaaggccg ccgcggccg ccatcggcat tttcttttgc gttttttattt    5400 gttaactgtt aattgtcctt gttcaaggat gctgtctttg acaacagatg ttttcttgcc    5460
tttgatgttc agcaggaagc tcggcgcaaa cgttgattgt ttgtctgcgt agaatcctct    5520
gtttgtcata tagcttgtaa tcacgacatt gttccttc gcttgaggta cagcgaagtg      5580
tgagtaagta aaggttacat cgttaggatc aagatccatt tttaacacaa ggccagtttt    5640
gttcagcggc ttgtatgggc cagttaaaga attagaaaca taaccaagca tgtaaatatc    5700
gttagacgta atgccgtcaa tcgtcatttt tgatccgcgg gagtcagtga acaggtacca    5760
tttgccgttc attttaaaga cgttcgcgcg ttcaatttca tctgttactg tgttagatgc    5820
aatcagcggt ttcatcactt ttttcagtgt gtaatcatcg tttagctcaa tcataccgag    5880
agcgccgttt gctaactcag ccgtgcgttt tttatcgctt tgcagaagtt tttgactttc    5940
ttgacggaag aatgatgtgc ttttgccata gtatgctttg ttaaataaag attcttcgcc    6000
ttggtagcca tcttcagttc cagtgtttgc ttcaaatact aagtatttgt ggcctttatc    6060
ttctacgtag tgaggatctc tcagcgtatg gttgtcgcct gagctgtagt tgccttcatc    6120
gatgaactgc tgtacatttt gatacgtttt tccgtcaccg tcaaagattg atttataatc    6180
ctctacaccg ttgatgttca aagagctgtc tgatgctgat acgttaactt gtgcagttgt    6240
cagtgtttgt ttgccgtaat gtttaccgga gaaatcagtg tagaataaac ggattttcc     6300
```

```
gtcagatgta aatgtggctg aacctgacca ttcttgtgtt tggtcttttta ggatagaatc    6360 atttgcatcg aatttgtcgc tgtctttaaa gacgcggcca gcgttttttcc agctgtcaat    6420 agaagtttcg ccgactttt gatagaacat gtaaatcgat gtgtcatccg cattttttagg    6480 atctccggct aatgcaaaga cgatgtggta gccgtgatag tttgcgacag tgccgtcagc    6540
gttttgtaat ggccagctgt cccaaacgtc caggcctttt gcagaagaga tatttttaat    6600
tgtggacgaa tcaaattcag aaacttgata ttttcatttt ttttgctgtt cagggatttg    6660
cagcatatca tggcgtgtaa tatgggaaat gccgtatgtt tccttatatg gcttttggtt    6720 cgtttcttc gcaaacgctt gagttgcgcc tcctgccagc agtgcggtag taaaggttaa    6780
tactgttgct tgttttgcaa acttttttgat gttcatcgtt catgtctcct ttttatgta    6840 ctgtgttagc ggtctgcttc ttccagcccct cctgtttgaa gatggcaagt tagttacgca    6900
caataaaaaa agacctaaaa tatgtaaggg gtgacgccaa agtatacact ttgcccttta    6960
cacattttag gtcttgcctg ctttatcagt aacaaacccg cgcgatttac ttttcgacct    7020
cattctatta gactctcgtt tggattgcaa ctggtctatt ttcctctttt gtttgataga    7080
aaatcataaa aggatttgca gactacgggc ctaaagaact aaaaaatcta tctgtttctt    7140
ttcattctct gtattttttta tagtttctgt tgcatgggca taaagttgcc ttttttaatca   7200 caattcagaa aatatcataa tatctcattt cactaaataa tagtgaacgg caggtatatg     7260
tgatgggtta aaaaggatcg gcggccgctc gatttaaatc                           7300
```

<210> SEQ ID NO 9
<211> LENGTH: 7161
<212> TYPE: DNA
<213> ORGANISM: artificial sequence
<220> FEATURE:
<223> OTHER INFORMATION: complete nucleotide sequence of plasmid
      pSacB_pflD

<400> SEQUENCE: 9

```
tcgagaggcc tgacgtcggg cccggtacca cgcgtcatat gactagttcg gacctaggga      60
tgggatcgag ctcttttcct tgccgacaag gcggaagctt taggggaaat tcccgtaggt    120
gccgtattgg tggatgaacg gggcaatatc attggtgaag gctggaacct ctctattgtg    180
aactcggatc ccaccgccca tgccgaaatt attgcgttgc gtaacgccgc gcagaaaatc    240
caaaattacc gcctgctcaa taccacttta tacgtgactt tagaaccctg caccatgtgc    300
gccggcgcga ttacacacag ccgaatcaaa cgcttggtat tcggggcgtc cgattacaaa    360
accggtgcgg tgggttccag atttcatttt tttgaggatt ataaaatgaa tcatgggtt     420 gagatcacaa gcggtgtctt ataggatcaa tgcagtcaga agttaagccg cttttttccaa   480 aagcgcaggg aacagaaaaa acaacaaaaa gctaccgcac ttttacaaca ccccccggctt   540 aactcctctg aaaatagtg acaaaaaaac cgtcataatg tttacgacgg ttttttttatt    600 tcttctaata tgtcacatta agcccgtagc ctgcaagcaa cccctaaca tgctccatta     660 attcttttgt cggcggtttt acatcttcaa gctcgtattt atcgccgagt acttcccatt    720
tatgggcgcc tagacggtga taaggtaata attccacttt ttcgatattc ttcatatctt    780
taatgaaatt ccccagcatg tgcaaatctt cgtcactatc tgtataaccc ggcactacaa    840
catggcggat ccaggtacgc tgatttcgat ccgctaaata ttttgcgaat tcgagcactc    900
ttttattcgg cacgccaatc aggctttcgt gaacccgttc attcatttct ttcaggtcaa    960
gcaacacaag atccgtgtca tcaatcaatt catcaataat atgatcatga tgacggacga   1020
```

```
aaccgttggt atccaagcaa gtattaattc cttctttatg gcaggctctg aaccagtccc   1080
gtacaaattc cgcctgtaaa atagcttcac cgccggaagc ggtaactccg ccgcccgagg   1140
cgttcataaa atggcgatag gtcaccactt ctttcattaa ttcttcaacg gaaatttctt   1200
taccgccgtg caaatcccag gtgtctctgt tatggcaata tttacaacgc attaagcagc   1260
cttgtaaaaa taaataaag cggattcccg gcccgtcaac tgtcccgcag gtttcaaatg   1320
aatgaattcg tcctaaaacc gacataatat gcccttaaat aatcaacaaa atatagcaag   1380
aagattatag caaagaattt cgttttttc agagaatagt caaatcttcg caaaaaacta   1440
ccgcactttt atccgcttta atcagggaa ttaaaacaaa aaaattccgc ctattgaggc   1500
ggaatttatt aagcaataag acaaactctc aattttaata cttccttctt ttctagtatt   1560
gataagattg aaaccttgca aggatgacgg cggatttgcc gtcactctca cccaactaat   1620
gtggacgact ggtaaaccat tgcattagac caatgcaaac accaccaccg acgatgttac   1680
ctaaagtaac aggaattaaa ttttaatta ctaaatggta catatctaaa tttgcaaact   1740
gctcggcatt taaacccgtt gcctgccaga attccggcga tgcgaaattt gcaattacca   1800
tgcccatagg gatcataaac atatttgcta cgcagtgttc aaagcctgaa gcgacaaaya   1860
acccgatcgg caggatcata ataaaagctt tatccgttag agtyttgccg gcataggcca   1920
tccaaacggc aatacatacc ataatgttgc aaagaatacc taaacagaag gcttcaaycc   1980
aggtatgttc tattttatgt tgtgccgtat ttaaaatggt taatccccac tgaccgtttg   2040
ccgccatgat ctgaccggaa aaccaaatta atgcaacaat aaataaaccg ccgacaaaat   2100
taccgaarta aaccacaatc cagttacgta acatctgaat tgttgtaatt ttactctcaa   2160
agcgggcaat agtcgataaa gttgatgaag taaatagttc acagccgcaa accgccacca   2220
taattacccc gagagagaac accaaaccgc cgaccagttt agttaatccc caaggcgctc   2280
ccgcagaggc tgtttgagtt gttgtataaa aaacgaatgc aagagcaata aacataccgg   2340
cagagatcgc cgataaaaat gaataggctt gttttttcgt agctttataa acgccgacgt   2400
ctaacccggt ttgagccatc tcggttggcg aagccatcca agccaattta aaatcttccg   2460
atttcattga gctttcctta gtaataaaac tactcggaaa tgagtagaac tgccttaaag   2520
cataaatgat agattaaaaa atccaaaatt gttgaatatt atttaacggg gggattataa   2580
aagattcata aattagataa tagctaattt gagtgatcca tatcaccttt tacagatttt   2640
ttgacctaaa tcaaaattac ccaaatagag taataatacc attataaagg gtgtggattt   2700
attcctttgg tttacgagat aaattgctat ttaagctgat ttctgataaa aagtgcggta   2760
gattttcccc aaaaataagg aaacacaaaa tggcagaaga aacaattttc agtaaaatta   2820
ttcgtaaaga aattcccgcc gacattatat atcaagacga tcttgtcacc gcatttgcg   2880 atattgcgcc gcaggcaaaa actcatattt taattattcc gaataaattg attccgacag   2940
taaacgacgt aaccgcccat cgtcgacatc gatgctcttc tgcgttaatt aacaattggg   3000
atcctctaga ctttgcttcc agatgtatgc tctcctccgg agagtaccgt gactttattt   3060
tcggcacaaa tacaggggtc gatggataaa tacggcgata gtttcctgac ggatgatccg   3120
tatgtaccgg cggaagacaa gctgcaaacc tgtcagatgg agattgattt aatggcggat   3180
gtgctgagag caccgccccg tgaatccgca gaactgatcc gctatgtgtt gcggatgat   3240 tggccggaat aaataaagcc gggcttaata cagattaagc ccgtataggg tattattact   3300
gaataccaaa cagcttacgg aggacggaat gttacccatt gagacaacca gactgccttc   3360
```

```
tgattattaa tattttttcac tattaatcag aaggaataac catgaatttt acccggattg   3420
acctgaatac ctggaatcgc agggaacact ttgcccttta tcgtcagcag attaaatgcg   3480
gattcagcct gaccaccaaa ctcgatatta ccgctttgcg taccgcactg gcggagacag   3540
gttataagtt ttatccgctg atgatttacc tgatctcccg ggctgttaat cagtttccgg   3600
agttccggat ggcactgaaa gacaatgaac ttatttactg ggaccagtca gacccggtct   3660
ttactgtctt tcataaagaa accgaaacat tctctgcact gtcctgccgt tatttttccgg  3720 atctcagtga gtttatggca ggttataatg cggtaacggc agaatatcag catgatacca   3780
gattgtttcc gcagggaaat ttaccggaga atcacctgaa tatatcatca ttaccgtggg   3840
tgagttttga cgggatttaa cctgaacatc accggaaatg atgattattt tgccccggtt   3900
tttacgatgg caaagtttca gcaggaaggt gaccgcgtat tattacctgt ttctgtacag   3960
gttcatcatg cagtctgtga tggctttcat gcagcacggt ttattaatac acttcagctg   4020
atgtgtgata acatactgaa ataaattaat taattctgta tttaagccac cgtatccggc   4080
aggaatggtg gcttttttt tatattttaa ccgtaatctg taatttcgtt tcagactggt   4140
tcaggatgag ctcgcttgga ctcctgttga tagatccagt aatgacctca gaactccatc   4200
tggatttgtt cagaacgctc ggttgccgcc gggcgttttt tattggtgag aatccaagca   4260
ctagcggcgc gccggccggc ccggtgtgaa ataccgcaca gatgcgtaag gagaaaatac   4320
cgcatcaggc gctcttccgc ttcctcgctc actgactcgc tgcgctcggt cgttcggctg   4380
cggcgagcgg tatcagctca ctcaaaggcg gtaatacggt tatccacaga atcaggggat   4440
aacgcaggaa agaacatgtg agcaaaaggc cagcaaaagg ccaggaaccg taaaaaggcc   4500
gcgttgctgg cgtttttcca taggctccgc cccccctgacg agcatcacaa aaatcgacgc   4560
tcaagtcaga ggtggcgaaa cccgacagga ctataaagat accaggcgtt tccccctgga   4620
agctccctcg tgcgctctcc tgttccgacc ctgccgctta ccggatacct gtccgccttt   4680
ctcccttcgg gaagcgtggc gctttctcat agctcacgct gtaggtatct cagttcggtg   4740
taggtcgttc gctccaagct gggctgtgtg cacgaacccc ccgttcagcc cgaccgctgc   4800
gccttatccg gtaactatcg tcttgagtcc aacccggtaa gacacgactt atcgccactg   4860
gcagcagcca ctggtaacag gattagcaga gcgaggtatg taggcggtgc tacagagttc   4920
ttgaagtggt ggcctaacta cggctacact agaaggacag tatttggtat ctgcgctctg   4980
ctgaagccag ttaccttcgg aaaaagagtt ggtagctctt gatccggcaa acaaaccacc   5040
gctggtagcg gtggtttttt tgtttgcaag cagcagatta cgcgcagaaa aaaaggatct   5100
caagaagatc ctttgatctt ttctacgggg tctgacgctc agtggaacga aaactcacgt   5160
taagggattt tggtcatgag attatcaaaa aggatcttca cctagatcct ttttaaggcc   5220
ggccgcggcc gccatcggca ttttcttttg cgtttttatt tgttaactgt taattgtcct   5280
tgttcaagga tgctgtcttt gacaacagat gttttcttgc ctttgatgtt cagcaggaag   5340
ctcggcgcaa acgttgattg tttgtctgcg tagaatcctc tgtttgtcat atagcttgta   5400
atcacgacat tgtttccttt cgcttgaggt acagcgaagt gtgagtaagt aaaggttaca   5460
tcgttaggat caagatccat tttttaacaca aggccagttt tgttcagcgg cttgtatggg   5520
ccagttaaag aattagaaac ataaccaagc atgtaaatat cgttagacgt aatgccgtca   5580
atcgtcattt tgatccgcg ggagtcagtg aacaggtacc atttgccgtt catttttaaag  5640 acgttcgcgc gttcaatttc atctgttact gtgttagatg caatcagcgg tttcatcact   5700
tttttcagtg tgtaatcatc gtttagctca atcataccga gagcgccgtt tgctaactca   5760
```

```
gccgtgcgtt ttttatcgct ttgcagaagt ttttgacttt cttgacggaa gaatgatgtg    5820
cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggttgtcgcc tgagctgtag ttgccttcat cgatgaactg ctgtacattt    6000
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggattttc cgtcagatgt aaatgtggct    6180
gaacctgacc attcttgtgt ttggtctttt aggatagaat catttgcatc gaatttgtcg    6240
ctgtctttaa agacgcggcc agcgttttc cagctgtcaa tagaagtttc gccgactttt    6300
tgatagaaca tgtaaatcga tgtgtcatcc gcattttag gatctccggc taatgcaaag    6360
acgatgtggt agccgtgata gtttgcgaca gtgccgtcag cgttttgtaa tggccagctg    6420
tcccaaacgt ccaggccttt tgcagaagag atattttaa ttgtggacga atcaaattca    6480
gaaacttgat attttttcatt ttttttgctgt tcagggattt gcagcatatc atggcgtgta    6540
atatgggaaa tgccgtatgt ttccttatat ggcttttggt tcgtttcttt cgcaaacgct    6600
tgagttgcgc ctcctgccag cagtgcggta gtaaaggtta atactgttgc ttgttttgca    6660
aactttttga tgttcatcgt tcatgtctcc tttttatgt actgtgttag cggtctgctt    6720
cttccagccc tcctgtttga agatggcaag ttagttacgc acaataaaaa aagacctaaa    6780
atatgtaagg ggtgacgcca agtatacac tttgcccttt acacatttta ggtcttgcct    6840
gctttatcag taacaaaccc gcgcgattta cttttcgacc tcattctatt agactctcgt    6900
ttggattgca actggtctat tttcctcttt tgtttgatag aaaatcataa aaggatttgc    6960
agactacggg cctaaagaac taaaaaatct atctgtttct tttcattctc tgtatttttt    7020
atagtttctg ttgcatgggc ataaagttgc cttttaatc acaattcaga aaatatcata    7080
atatctcatt tcactaaata atagtgaacg gcaggtatat gtgatgggtt aaaaaggatc    7140
ggcggccgct cgatttaaat c                                             7161
```

<210> SEQ ID NO 10
<211> LENGTH: 1029
<212> TYPE: DNA
<213> ORGANISM: Basfia succiniciproducens
<220> FEATURE:
<221> NAME/KEY: MISC_FEATURE
<223> OTHER INFORMATION: nucleotide sequence of ldhA-gene from strain
      DD1

<400> SEQUENCE: 10

```
ttgacaaaat cagtatgttt aaataaggag ctaactatga aagttgccgt ttacagtact      60
aaaaattatg atcgcaaaca tctggatttg gcgaataaaa aatttaattt tgagcttcat     120
ttctttgatt tttacttga tgaacaaacc gcgaaatgg cggagggcgc cgatgccgtc     180 tgtatttcg tcaatgatga tgcgagccgc ccggtgttaa caagttggc gcaaatcgga     240 gtgaaaatta tcgctttacg ttgtgccggt tttaataatg tggatttgga ggcggcaaaa     300
gagctgggat taaagtcgt acgggtgcct gcgtattcgc cggaagccgt tgccgagcat     360
gcgatcggat taatgctgac tttaaaccgc cgtatccata aggcttatca gcgtacccgc     420
gatgcgaatt tttctctgga aggattggtc ggttttaata tgttcggcaa aaccgccgga     480
gtgattggta cgggaaaaat cggcttggcg gctattcgca ttttaaaagg cttcggtatg     540
```

```
gacgttctgg cgtttgatcc ttttaaaaat ccggcggcgg aagcgttggg cgcaaaatat    600
gtcggtttag acgagcttta tgcaaaatcc catgttatca ctttgcattg cccggctacg    660
gcggataatt atcatttatt aaatgaagcg gcttttaata aaatgcgcga cggtgtaatg    720
attattaata ccagccgcgg cgttttaatt gacagccggg cggcaatcga agcgttaaaa    780
cggcagaaaa tcggcgctct cggtatggat gtttatgaaa atgaacggga tttgtttttc    840
gaggataaat ctaacgatgt tattacggat gatgtattcc gtcgcctttc ttcctgtcat    900
aatgtgcttt ttaccggtca tcaggcgttt ttaacggaag aagcgctgaa taatatcgcc    960
gatgtgactt tatcgaatat tcaggcggtt tccaaaaatg caacgtgcga aaatagcgtt   1020
gaaggctaa                                                          1029
```

<210> SEQ ID NO 11
<211> LENGTH: 342
<212> TYPE: PRT
<213> ORGANISM: Basfia succiniciproducens
<220> FEATURE:
<221> NAME/KEY: MISC_FEATURE
<223> OTHER INFORMATION: amino acid sequence of LdhA from strain DD1

<400> SEQUENCE: 11

```
Met Thr Lys Ser Val Cys Leu Asn Lys Glu Leu Thr Met Lys Val Ala
 1               5                  10                  15

Val Tyr Ser Thr Lys Asn Tyr Asp Arg Lys His Leu Asp Leu Ala Asn
            20                  25                  30

Lys Lys Phe Asn Phe Glu Leu His Phe Phe Asp Phe Leu Leu Asp Glu
        35                  40                  45

Gln Thr Ala Lys Met Ala Glu Gly Ala Asp Ala Val Cys Ile Phe Val
    50                  55                  60

Asn Asp Asp Ala Ser Arg Pro Val Leu Thr Lys Leu Ala Gln Ile Gly
65                  70                  75                  80

Val Lys Ile Ile Ala Leu Arg Cys Ala Gly Phe Asn Asn Val Asp Leu
                85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
    130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
    210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270
```

```
Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
    290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 12
<211> LENGTH: 741
<212> TYPE: DNA
<213> ORGANISM: Basfia succiniciproducens
<220> FEATURE:
<221> NAME/KEY: MISC_FEATURE
<223> OTHER INFORMATION: nucleotide sequence of pflA-gene from strain
      DD1

<400> SEQUENCE: 12
atgtcggttt taggacgaat tcattcattt gaaacctgcg ggacagttga cgggccggga      60
atccgctttA ttttattttt acaaggctgc ttaatgcgtt gtaaatactg ccataataga     120
gacacctggg atttgcacgg cggtaaagaa atttccgttg aagaattaat gaaagaagtg     180
gtgacctatc gccattttat gaacgcctcg ggcggcggag ttaccgcttc cggcggtgaa     240
gctattttac aggcggaatt tgtacgggac tggttcagag cctgccataa agaaggaatt     300
aatacttgct tggataccaa cggtttcgtc cgtcatcatg atcatattat tgatgaattg     360
attgatgaca cggatcttgt gttgcttgac ctgaaagaaa tgaatgaacg ggttcacgaa     420
agcctgattg gcgtgccgaa taaagagtg ctcgaattcg caaatatttt agcggatcga     480
aatcagcgta cctggatccg ccatgttgta gtgcccggt atacagatag tgacgaagat     540
ttgcacatgc tggggaattt cattaaagat atgaagaata tcgaaaaagt ggaattatta     600
ccttatcacc gtctaggcgc ccataaatgg gaagtactcg gcgataaata cgagcttgaa     660
gatgtaaaac cgccgacaaa agaattaatg gagcatgtta aggggttgct tgcaggctac     720
gggcttaatg tgacatatta g                                                741

<210> SEQ ID NO 13
<211> LENGTH: 246
<212> TYPE: PRT
<213> ORGANISM: Basfia succiniciproducens
<220> FEATURE:
<221> NAME/KEY: MISC_FEATURE
<223> OTHER INFORMATION: amino acid sequence of PflA from strain DD1

<400> SEQUENCE: 13

Met Ser Val Leu Gly Arg Ile His Ser Phe Glu Thr Cys Gly Thr Val
1               5                   10                  15

Asp Gly Pro Gly Ile Arg Phe Ile Leu Phe Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Glu Val Val Thr Tyr Arg
    50                  55                  60

His Phe Met Asn Ala Ser Gly Gly Gly Val Thr Ala Ser Gly Gly Glu
65                  70                  75                  80
```

```
Ala Ile Leu Gln Ala Glu Phe Val Arg Asp Trp Phe Arg Ala Cys His
                85                  90                  95

Lys Glu Gly Ile Asn Thr Cys Leu Asp Thr Asn Gly Phe Val Arg His
            100                 105                 110

His Asp His Ile Ile Asp Glu Leu Ile Asp Thr Asp Leu Val Leu
        115                 120                 125

Leu Asp Leu Lys Glu Met Asn Glu Arg Val His Glu Ser Leu Ile Gly
    130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
                165                 170                 175

Ser Asp Glu Asp Leu His Met Leu Gly Asn Phe Ile Lys Asp Met Lys
            180                 185                 190

Asn Ile Glu Lys Val Glu Leu Leu Pro Tyr His Arg Leu Gly Ala His
            195                 200                 205

Lys Trp Glu Val Leu Gly Asp Lys Tyr Glu Leu Glu Asp Val Lys Pro
    210                 215                 220

Pro Thr Lys Glu Leu Met Glu His Val Lys Gly Leu Leu Ala Gly Tyr
225                 230                 235                 240

Gly Leu Asn Val Thr Tyr
                245

<210> SEQ ID NO 14
<211> LENGTH: 2313
<212> TYPE: DNA
<213> ORGANISM: Basfia succiniciproducens
<220> FEATURE:
<221> NAME/KEY: MISC_FEATURE
<223> OTHER INFORMATION: nucleotide sequence of pflD-gene from strain
      DD1

<400> SEQUENCE: 14
atggctgaat taacagaagc tcaaaaaaaa gcatgggaag gattcgttcc cggtgaatgg     60
caaaacggcg taaatttacg tgactttatc caaaaaaact atactccgta tgaaggtgac    120
gaatcattct tagctgatgc gactcctgca accagcgagt tgtggaacag cgtgatggaa    180
ggcatcaaaa tcgaaaacaa aactcacgca cctttagatt cgacgaaca tactccgtca    240 actatcactt ctcacaagcc tggttatatc aataaagatt tagaaaaaat cgttggtctt    300
caaacagacg ctccgttaaa acgtgcaatt atgccgtacg gcggtatcaa atgatcaaa    360 ggttcttgcg aagtttacgg tcgtaaatta gatccgcaag tagaatttat tttcaccgaa    420
tatcgtaaaa cccataacca aggcgtattc gacgtttata cgccggatat tttacgctgc    480
cgtaaatcag gcgtgttaac cggtttaccg gatgcttacg gtcgtggtcg tattatcggt    540
gactaccgtc gtttagcggt atacggtatt gattacctga tgaagataa aaaagcccaa    600 ttcgattcat tacaaccgcg tttggaagcg ggcgaagaca ttcaggcaac tatccaatta    660
cgtgaagaaa ttgccgaaca caccgcgct ttaggcaaaa tcaaagaaat ggcggcatct    720
tacggttacg acatttccgg ccctgcgaca aacgcacagg aagcaatcca atggacatat    780
tttgcttatc tggcagcggt taaatcacaa acggtgcgg caatgtcatt cggtcgtacg    840
tctacattct agatatcta tatcgaacgt gacttaaaac gcggttaat cactgaacaa    900 caggcgcaga attatgga ccacttagta atgaaattac gtatggttcg tttcttacgt    960
acgccggaat acgatcaatt attctcaggc gacccgatgt gggcaaccga actatcgcc   1020
```

```
ggtatgggct tagacggtcg tccgttggta actaaaaaca gcttccgcgt attacatact   1080
ttatacacta tgggtacttc tccggaacca aacttaacta ttctttggtc cgaacaatta   1140
cctgaagcgt tcaaacgttt ctgtgcgaaa gtatctattg atacttcctc cgtacaatac   1200
gaaaatgatg acttaatgcg tcctgacttc aacaacgatg actatgcaat cgcatgctgc   1260
gtatcaccga tggtcgtagg taaacaaatg caattcttcg gtgcgcgcgc aaacttagct   1320
aaaactatgt tatacgcaat taacggcggt atcgatgaga aaaatggtat gcaagtcggt   1380
cctaaaactg cgccgattac agacgaagta ttgaatttcg ataccgtaat cgaacgtatg   1440
gacagtttca tggactggtt ggcgactcaa tatgtaaccg cattgaacat catccacttc   1500
atgcacgata aatatgcata tgaagcggca ttgatggcgt tccacgatcg cgacgtattc   1560
cgtacaatgg cttgcggtat cgcgggtctt tccgtggctg cggactcatt atccgcaatc   1620
aaatatgcga agttaaaacc gattcgcggc gacatcaaag ataaagacgg taatgtcgtg   1680
gcctcgaatt ttgctatcga cttcgaaatt gaaggcgaat atccgcaatt cggtaacaat   1740
gatccgcgtg ttgatgattt agcggtagac ttagttgaac gtttcatgaa aaaagttcaa   1800
aaacacaaaa cttaccgcaa cgcaactccg acacaatcta tcctgactat cacttctaac   1860
gtggtatacg gtaagaaaac cggtaatact ccggacggtc gtcgagcagg cgcgccattc   1920
ggaccgggtg caaacccaat gcacggtcgt gaccaaaaag gtgcggttgc ttcacttact   1980
tctgtggcta aacttccgtt cgcttacgcg aaagacggta tttcatatac cttctctatc   2040
gtaccgaacg cattaggtaa agatgacgaa gcgcaaaaac gcaaccttgc cggtttaatg   2100
gacggttatt tccatcatga agcgacagtg gaaggcggtc aacacttgaa tgttaacgtt   2160
cttaaccgtg aaatgttgtt agacgcgatg gaaaatccgg aaaaatacccc gcaattaacc   2220 attcgtgttt caggttacgc ggttcgtttc aactcattaa ctaaagagca acaacaagac   2280
gtcatcactc gtacgtttac acaatcaatg taa                                 2313
```

<210> SEQ ID NO 15  
<211> LENGTH: 770  
<212> TYPE: PRT  
<213> ORGANISM: Basfia succiniciproducens  
<220> FEATURE:  
<221> NAME/KEY: MISC_FEATURE  
<223> OTHER INFORMATION: amino acid of PflD from strain DD1

<400> SEQUENCE: 15

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125
```

-continued

Lys Leu Asp Pro Gln Val Glu Phe Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Gln Ala Gln Glu
    290                 295                 300

Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
                325                 330                 335

Glu Thr Ile Ala Gly Met Gly Leu Asp Gly Arg Pro Leu Val Thr Lys
            340                 345                 350

Asn Ser Phe Arg Val Leu His Thr Leu Tyr Thr Met Gly Thr Ser Pro
        355                 360                 365

Glu Pro Asn Leu Thr Ile Leu Trp Ser Glu Gln Leu Pro Glu Ala Phe
    370                 375                 380

Lys Arg Phe Cys Ala Lys Val Ser Ile Asp Thr Ser Ser Val Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Val Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Ile Asp Glu Lys Asn Gly Met Gln Val Gly Pro Lys Thr Ala
    450                 455                 460

Pro Ile Thr Asp Glu Val Leu Asn Phe Asp Thr Val Ile Glu Arg Met
465                 470                 475                 480

Asp Ser Phe Met Asp Trp Leu Ala Thr Gln Tyr Val Thr Ala Leu Asn
                485                 490                 495

Ile Ile His Phe Met His Asp Lys Tyr Ala Tyr Glu Ala Ala Leu Met
            500                 505                 510

Ala Phe His Asp Arg Asp Val Phe Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

| | | | | | | | | | | | | | | |
|---|---|---|---|---|---|---|---|---|---|---|---|---|---|---|
|Val|Lys|Pro|Ile|Arg|Gly|Asp|Ile|Lys|Asp|Lys|Asp|Gly|Asn|Val Val|
|545| | | |550| | | |555| | | |560| | |
|Ala|Ser|Asn|Val|Ala|Ile|Asp|Phe|Glu|Ile|Glu|Gly|Glu|Tyr|Pro Gln|
| | | | |565| | | |570| | | |575| | |
|Phe|Gly|Asn|Asn|Asp|Pro|Arg|Val|Asp|Asp|Leu|Ala|Val|Asp|Leu Val|
| | | |580| | | | |585| | | |590| | |
|Glu|Arg|Phe|Met|Lys|Lys|Val|Gln|Lys|His|Lys|Thr|Tyr|Arg|Asn Ala|
| | |595| | | | |600| | | | |605| | |
|Thr|Pro|Thr|Gln|Ser|Ile|Leu|Thr|Ile|Thr|Ser|Asn|Val|Val|Tyr Gly|
| |610| | | | |615| | | | |620| | | |
|Lys|Lys|Thr|Gly|Asn|Thr|Pro|Asp|Gly|Arg|Arg|Ala|Gly|Ala|Pro Phe|
|625| | | |630| | | |635| | | |640| | |
|Gly|Pro|Gly|Ala|Asn|Pro|Met|His|Gly|Arg|Asp|Gln|Lys|Gly|Ala Val|
| | | |645| | | | |650| | | |655| | |
|Ala|Ser|Leu|Thr|Ser|Val|Ala|Lys|Leu|Pro|Phe|Ala|Tyr|Ala|Lys Asp|
| | |660| | | | |665| | | | |670| | |
|Gly|Ile|Ser|Tyr|Thr|Phe|Ser|Ile|Val|Pro|Asn|Ala|Leu|Gly|Lys Asp|
| |675| | | | |680| | | | |685| | | |
|Asp|Glu|Ala|Gln|Lys|Arg|Asn|Leu|Ala|Gly|Leu|Met|Asp|Gly|Tyr Phe|
|690| | | |695| | | |700| | | |705(?)| | |
|His|His|Glu|Ala|Thr|Val|Gly|Gly|Gln|His|Leu|Asn|Val|Asn|Val|
|705| | | |710| | | |715| | | |720| | |
|Leu|Asn|Arg|Glu|Met|Leu|Leu|Asp|Ala|Met|Glu|Asn|Pro|Glu|Lys Tyr|
| | | |725| | | | |730| | | | |735| | |
|Pro|Gln|Leu|Thr|Ile|Arg|Val|Ser|Gly|Tyr|Ala|Val|Arg|Phe|Asn Ser|
| | |740| | | | |745| | | | |750| | |
|Leu|Thr|Lys|Glu|Gln|Gln|Gln|Asp|Val|Ile|Thr|Arg|Thr|Phe|Thr Gln|
| |755| | | | |760| | | | |765| | | |
|Ser|Met| | | | | | | | | | | | | |
| |770| | | | | | | | | | | | | |

<210> SEQ ID NO 16
<211> LENGTH: 601
<212> TYPE: DNA
<213> ORGANISM: Basfia succiniciproducens
<220> FEATURE:
<221> NAME/KEY: MISC_FEATURE
<223> OTHER INFORMATION: nucleotide sequence of wcaJ-gene from strain
      DD1 with insertion of cytosine between nucleotides 81 and 82

<400> SEQUENCE: 16

```
atgataaaac gccttttcga tattgttgtc gcattgatag cattgatttt gttttcgccc    60
ttatatttgt ttgtggctta tcaaggtaaa acaaaatttg ggatcaccgg tgttatttaa   120
acaaacccgc cccggattgc atggtaaacc ctttgagatg attaagttca gaacaatgaa   180
agacggcgca gatgaaaacg gtaatatttt gccggatgcg gagcgcttaa cacctttcgg   240
caaaatgttg cgcgctacca gtctggacga gttgccggaa ctttggaatg tattaaaagg   300
tgatatgagt ctggtggggc cgcgtcctct actgatggaa tatttgccgc tgtataacga   360
aagacaggct aagcgccatg aagtgaaacc cggaattacc ggttatgcac aggtaaacgg   420
tcgcaatgcc atcagttggg agcagaaatt tgaattggat gcctggtatg ttgaacatca   480
atccttgtgg ctggatttga aaattatcgc aaagaccatc caaaaagtga tcgcaaaaga   540
cgatattaat gcggcagatg atgccaccat gcctaaattt gaagggaata aaaaatcatg   600
a                                                                  601
```

MODIFIED MICROORGANISM WITH IMPROVED BIOMASS SEPARATION BEHAVIOUR

This application is a National Stage application of International Application No. PCT/EP2015/052523, filed Feb. 6, 2015, which claims priority under 35 U.S.C. § 119 to European Patent Application Nos. 14154287.8, filed Feb. 7, 2014 and 14167002.6, filed May 5, 2014.

INCORPORATION BY REFERENCE OF MATERIAL SUBMITTED ELECTRONICALLY

This application incorporates by reference in its entirety a computer-readable nucleotide/amino acid sequence listing identified as one 72,391 byte ASCII (text) file named "H74822_SubSeqListing.txt," created Jul. 27, 2016.

The present invention relates to a modified microorganism, to a method for producing an organic compound and to the use of a modified microorganism.

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the ldhA-gene and/or the pflD- or the pflA-gene have been disrupted, are disclosed in WO-A-2010/092155, these mutant strains being characterized by a significantly increased production of succinic acid from carbon sources such as glycerol or mixtures of glycerol and carbohydrates such as maltose, under anaerobic conditions compared to the DD1-wild-type disclosed in WO-A-2009/024294.

However, when using bacterial strains such as those disclosed in WO-A-2009/024294 or WO-A-2010/092155 for the production or organic compounds such as succinic acid, the selectivity in which the carbon sources are converted into the desired organic compounds and also the yield of the desired organic compound is still improvable.

Furthermore, it has been observed that when using the bacterial strains of the prior art it is sometimes difficult to separate the biomass from the fermentation broth at the end of the fermentation process. Usually, the fermentative production of organic compounds such as succinic acid comprises the steps of cultivating the microorganisms under suitable culture conditions in a medium comprising at least one assimilable carbon source to allow the microorganism to produce the desired organic compound and the subsequent recovery of the organic compound from the fermentation broth, wherein in a first step of the recovery process the microorganisms (i.e. the biomass) are usually separated from the culture medium by, for example, sedimentation or centrifugation. When using the microorganisms of the prior art, the biomass can not be easily separated from the fermentation broth, which—as a part of the fermentation broth is somehow entrapped in the biomass—sometimes leads to a loss of a certain amount of the fermentation broth (and thus also a loss of a certain amount of the desired organic compound).

It was therefore an object of the present invention to overcome the disadvantages of the prior art.

In particular, it was an object of the present invention to provide microorganisms which can be used for the fermentative production of organic compounds such as succinic acid and which not only produce the desired organic products, such as succinic acid, from assimilable carbon sources such as glycerol, glucose, sucrose, xylose, lactose, fructose or maltose in large amounts, preferably with only low amounts of side products, but which can also easily be separated from the fermentation broth in the subsequent process of recovering the organic compound, with only a minor amount of the fermentation broth being entrapped in the biomass.

A contribution to achieving the abovementioned aims is provided by a modified microorganism having, compared to its wild-type, a reduced activity of the enzyme that is encoded by the wcaJ-gene. A contribution to achieving the abovementioned aims is in particular provided by a modified microorganism which the wcaJ-gene or parts thereof have been deleted or in which a regulatory element of the wcaJ-gene or at least a part thereof has been deleted or in which at least one mutation has been introduced into the wcaJ-gene.

Surprisingly, it has been discovered that a reduction of the activity of the enzyme that is encoded by the wcaJ-gene (this enzyme presumably being a glucose transferase), for example by a deletion of the wcaJ-gene or parts thereof, results in a microorganism that, after fermentative production of organic compounds such as succinic acid in an appropriate culture medium, can be separated—as the biomass—from the culture medium more easily compared to the corresponding microorganism in which the activity of this enzyme has not been decreased. When using the modified microorganism according to the present invention, less fermentation broth in entrapped in the biomass that is separated in the purification process, which means that a higher amount of fermentation broth per gram of biomass used in the fermentation process (and thus a higher amount of the desired organic compound such as succinic acid) can be obtained from which the organic compound is isolated.

In context with the expression "a modified microorganism having, compared to its wild-type, a reduced activity of the enzyme that is encoded by the x-gene", wherein the x-gene is the fruA-gene and optionally, as described later, the ldhA-gene, the pflA-gene and/or the pflD-gene, the term "wild-type" refers to a microorganism in which the activity of the enzyme that is encoded by the x-gene has not been decreased, i.e. to a microorganism whose genome is present in a state as before the introduction of a genetic modification of the x-gene. Preferably, the expression "wild-type" refers to a microorganism (e.g., bacteria, yeast cell, fungal cell, etc.) whose genome, in particular whose x-gene, is present in a state as generated naturally as the result of evolution. The term is used both for the entire microorganism and for individual genes. As a consequence, the term "wild-type" preferably does not cover in particular those microorganisms, or those genes, whose gene sequences have at least in part been modified by man by means of recombinant methods. The term "modified microorganism" thus includes a microorganism which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring wild-type microorganism from which it was derived. According to a particular preferred embodiment of the modified microorganism according to the present invention the modified microorganism is a recombinant microorganism, which means that the microorganism has been obtained using recombinant. DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

The wild-type from which the microorganisms according to the present invention are derived may yeasts, fungi or bacteria. Suitable bacteria, yeasts or fungi are in particular those bacteria, yeasts or fungi which have been deposited at the Deutsche Sammlung von Mikroorganismen und Zellkulturen GmbH (DSMZ), Brunswick, Germany, as bacterial, yeast or fungal strains. The expression "a modified microorganism derived from a wild-type", as used herein, refers to a microorganism that has been obtained from the wild-type by a controlled genetic modification (e.g. genetic engineering), by an uncontrolled (random) genetic modification (e.g. a treatment with a mutagenizing chemical agent, X-rays, UV light etc.) or by a combination of these methods. Further details of preparing the modified microorganism according to the present invention are given below.

Bacteria which are suitable according to the invention belong to the genera detailed under
http://www.dsmz.de/species/bacteria.htm,
yeasts which are suitable according to the invention belong to those genera which are detailed under
http://www.dsmz.de/species/yeasts.htm,
and fungi which are suitable according to the invention are those which are detailed under
http://www.dsmz.de/speciesfiungi.htm.

Preferably, the wild-type from which the modified microorganism according to the present invention has been derived is a bacterial cell. The term "bacterial cell" as used herein refers to a prokaryotic organism, i.e. a bacterium. Bacteria can be classified based on their biochemical and microbiological properties as well as their morphology. These classification criteria are well known in the art.

According to a preferred embodiment of the modified microorganism according to the present invention the wild-type from which the modified microorganism has been derived belongs to the family of Enterobacteriaceae, Pasteurellaceae, Bacillaceae or Corynebacteriaceae.

"Enterobacteriaceae" represent a large family of bacteria, including many of the more familiar bacteria, such as *Salmonella* and *Escherichia coli*. They belong to the Proteobacteria, and they are given their own order (Enterobacteriales). Members of the Enterobacteriaceae are rod-shaped. Like other Proteobacteria they have Gram-negative stains, and they are facultative anaerobes, fermenting sugars to produce lactic acid and various other end products such as succinic acid. Most also reduce nitrate to nitrite. Unlike most similar bacteria, Enterobacteriaceae generally lack cytochrome C oxidase. Most have many flagella used to move about, but a few genera are non-motile. They are non-spare forming, and mostly they are catalase-positive. Many members of this family are a normal part of the gut flora found in the intestines of humans and other animals, while others are found in water or soil, or are parasites on a variety of different animals and plants. *Escherichia coli*, better known as *E. coli*, is one of the most important model organisms, and its genetics and biochemistry have been closely studied. Most members of Enterobacteriaceae have peritrichous Type I fimbriae involved in the adhesion of the bacterial cells to their hosts. Examples for the Enterobacteriaceae are *E. coli, Proteus, Salmonella* and *Klebsiella*.

"Pasteurellaceae" comprise a large family of Gram-negative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella. Bacteria in the family Pasteurellaceae have been classified into a number of genera based on metabolic properties and there sequences of the 16S RNA and 23S RNA. Many of the Pasteurellaceae contain pyruvate-formate-lyase genes and are capable of anaerobically fermenting carbon sources to organic acids.

"Bacillaceae" is a family of Gram-positive, heterotrophic, rod-shaped bacteria that may produce endospores. Motile members of this family are characterized by peritrichous flagellae. Some Bacillaceae are aerobic, while others are facultative or strict anaerobes. Most are nonpathogenic, but *Bacillus* species are known to cause disease in humans. This family also comprises the genus Bacilli which includes two orders, Bacillales and Lactobacillales. The *bacillus* species represents large cylindrical bacteria that can grow under aerobic conditions at 37° C. They are typically nonpathogenic. The genus Bacillales contains the species Alicyclobacillaceae, Bacillaceae, Caryophanaceae, Listeriaceae, Paenibacillaceae, Planococcaceae, Sporolactobacillaceae, Staphylococcaceae, Thermoactinomycetaceae, Turicibacteraceae. Many of the Bacilli contain pyruvate-formate-lyase genes and are capable of anaerobically fermenting carbon sources to organic acids.

"Corynebacteriaceae" is a large family of mostly Gram-positive and aerobic and nonmotile rod-shaped bacteria of the order Eubacteriales. This family also comprises the genus Corynebacterium, which is a genus of Gram-positive, rod-shaped bacteria. Corynebacteria are widely distributed in nature and are mostly innocuous. Some are useful in industrial settings such as C. glutamicum.

According to a particular preferred embodiment of the modified microorganism according to the present invention the wild-type from which the modified microorganism has been derived belongs to the family Pasteurellaceae. In this context it is furthermore preferred that the wild-type from which modified microorganism according to the present invention has been derived belongs to the genus Basfia and it is particularly preferred that the wild-type from which the modified microorganism has been derived belongs to the species Basfia succiniciproducens.

Most preferably, the wild-type from which the modified microorganism according to the present invention as been derived is Basfia succiniciproducens-strain DD1 deposited under the Budapest Treaty with DSMZ (Deutsche Sammlung von Mikroorganismen and Zellkulturen, GmbH), Germany, having the deposit number DSM 18541. This strain has been originally isolated from the rumen of a cow of German origin. Pasteurella bacteria can be isolated from the gastro-intestinal tract of animals and, preferably, mammals. The bacterial strain DD1, in particular, can be isolated from bovine rumen and is capable of utilizing glycerol (including crude glycerol) as a carbon source. Further strains of the genus Basfia that can be used for preparing the modified microorganism according to the present invention are the Basfia-strain that has been deposited under the deposit number DSM 22022 or the Basfia-strains that have been deposited with the Culture Collection of the University of Goteborg (CCUG), Sweden, having the deposit numbers CCUG 57335, CCUG 57762, CCUG 57763, CCUG 57764, CCUG 57765 or CCUG 57766. Said strains have been originally isolated from the rumen of cows of German or Swiss origin.

In this context it is particularly preferred that the wild-type from which the modified microorganism according to the present invention has been derived has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the wild-type from which the modified microorganism according to the present invention has been derived has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, http://emboss.source-forge.net/what/) with the default parameters which are, i.e. gap open (penalty to open a gap): 10.0, gap extend (penalty to extend a gap): 0.5, and data file (scoring matrix file included in package): EDNAFUL.

It should be noted that the recombinant microorganisms according to the present invention can not only be derived from the above mentioned wild-type-microorganisms, especially from Basfia succiniciproducens-strain DD1, but also from variants of these strains. In this context the expression "a variant of a strain" comprises every strain having the same or essentially the same characteristics as the wild-type-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. A variant of a strain in the sense of this definition can, for example, be obtained by treating the wild-type-strain with a mutagenizing chemical agent, X-rays, or UV light.

The modified microorganism according to the present invention is characterized in that, corm pared to its wild-type, the activity of the enzyme that is encoded by the wcaJ-gene is reduced.

The reduction of the enzyme activity ($\Delta_{activity}$) is defined as follows:

$$\Delta_{activity} = 100\% - \left(\frac{\text{activity of the modified microorganism}}{\text{acvtivity of the wildtype}} \times 100\%\right)$$

wherein, when determining $\Delta_{activity}$, the activity in the wild-type and the activity in the modified microorganism are determined under exactly the same conditions. Methods for the detection and determination of the activity of the enzyme that is encoded by the wcaJ-gene can be found, for example, in Nothaft et al.: "*In vivo analysis of HPr reveals a fructose-specific phosphotransferase system that confers high-affinity uptake in Streptomyces coelicolor*", Journal of bacteriology, Vol. 185 (3), pages 929-937.

The reduced activity of the enzymes disclosed herein, in particular the reduced activity of the enzyme encoded by the wcaJ-gene, the lactate dehydrogenase and/or the pyruvate formate lyase, can be a reduction of the enzymatic activity by at least 50%, compared to the activity of said enzyme in the wild-type of the microorganism, or a reduction of the enzymatic activity by at least 90%, or more preferably a reduction of the enzymatic activity by at least 95%, or more preferably a reduction of the enzymatic activity by at least 98%, or even more preferably a reduction of the enzymatic activity by at least 99% or even more preferably a reduction of the enzymatic activity by at least 99.9%. The term "reduced activity of the enzyme that is encoded by the wcaJ-gene" or—as described below—"a reduced lactate dehydrogenase activity" or "a reduced pyruvate formate lyase activity", also encompasses a modified microorganism which has no detectable activity of these enzymes.

The term "reduced activity of an enzyme" includes, for example, the expression of the enzyme by said genetically manipulated (e.g., genetically engineered) microorganism at a lower level than that expressed by the wild-type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or iRNA or other methods to knock-out or block expression of the tar-get protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state Microorganisms having a reduced activity of the enzyme encoded by the wcaJ-gene may occur naturally, i.e. due to spontaneous mutations. A microorganism can be modified to lack or to have significantly reduced activity of the enzyme that is encoded by the wcaJ-gene by various techniques, such as chemical treatment or radiation. To this end, micro-organisms will be treated by, e.g., a mutagenizing chemical agent, X-rays, or UV light. In a subsequent step, those microorganisms which have a reduced activity of the enzyme that is encoded by the wcaJ-gene will be selected. Modified microorganisms are also obtainable by homologous recombination techniques which aim to mutate, disrupt or excise the wcaJ-gene in the genome of the microorganism or to substitute the gene with a corresponding gene that encodes for an enzyme which, compared to the enzyme encoded by the wild-type-gene, has a reduced activity.

According to a preferred embodiment of the modified microorganism according to the present invention, a reduction of the activity of the enzyme encoded by the wcaJ-gene is achieved by a modification of the wcaJ-gene, wherein this gene modification is preferably realized by a deletion of the wcaJ-gene or at least a part thereof, a deletion of a regulatory element of the wcaJ-gene or at least a part thereof, such as a promotor sequence, or by an introduction of at least one mutation into the wcaJ-gene. In context with the introduction of at least one mutation into the wcaJ-gene it is particularly preferred that the at least one mutation leads to the expression of a truncated enzyme encoded by the wcaJ-gene. It is furthermore preferred that in the truncated enzyme at least 100 amino acids, preferably at least 125 amino acids, more preferred at least 150 amino acids and most preferred at least 160 amino acids of the wild-type enzyme encoded by the wcaJ-gene are deleted from the C-terminal end. Such a truncated enzyme encoded the wcaJ-gene can, for example, be obtained by inserting or deleting nucleotides at appropriate positions within the wcaJ-gene gene which leads to a frame shift mutation, wherein by means of this frame shift mutation a stop codon introduced. For example, insertion of a nucleotide in the codon that encodes of lysine between thymine at position 81 and adenine at position 82 leads to a frame shift mutation by means of which a stop codon is introduced as shown in SEQ ID NO: 16. Such mutations of the wcaJ-gene can be introduced, for example, by site-directed or random mutagenesis, followed by an introduc-tion of the modified gene into the genome of the microorganism by recombination. Variants of the wcaJ-gene can be are generated by mutating the wcaJ-gene sequence SEQ ID NO: 3 by means of PCR. The "*Quickchange Site-directed Mutagenesis Kit*" (Stratagene) can be used to carry out a directed mutagenesis. A random mutagenesis over the entire coding sequence, or else only part thereof, of SEQ ID NO: 3 can be performed with the aid of the "*GeneMorph II Random Mutagenesis Kit*" (Stratagene).

In the following, a suitable technique for recombination, in particular for introducing a mutation or for deleting sequences, is described.

This technique is also sometimes referred to as the "Campbell recombination" herein (Leenhouts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

The wcaJ-gene the activity of which is reduced in the modified microorganism according to the present invention preferably comprises a nucleic acid selected from the group consisting of:
a) nucleic acids having the nucleotide sequence of SEQ ID NO: 3;
b) nucleic acids encoding the amino acid sequence of SEQ ID NO: 4;
c) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a) or b), the identity being the identity over the total length of the nucleic acids of a) or b);
d) nucleic acid encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a) or b), the identity being the identity over the total length of amino acid sequence encoded by the nucleic acids of a) or b)
e) nucleic acids capable of hybridizing under stringent conditions with a complementary sequence of any of the nucleic acids according to a) or b); and
f) nucleic acids encoding the same protein as any of the nucleic acids of a) or b), but differing from the nucleic acids of a) or b) above due to the degeneracy of the genetic code.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M Na—PO4, 1 mM EDTA at 50° C. with washing in 0.1×SSC, 0.1% SDS at 50° C. or 65° C., preferably 65° C. Preferably, the complementary nucleotides hybridize with a fragment or the whole wcaJ nucleic acids. Alternatively, preferred hybridization conditions encompass hybridization at 65° C. in 1×SSC or at 42° C. in 1×SSC and 50% formamide, followed by washing at 65° C. in 0.3×SSC or hybridization at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The wcaJ-gene or parts of which that may be deleted by the above mentioned "Campbell recombination" or in which at least one mutation is introduced by the above mentioned "Campbell recombination" preferably comprises a nucleic acid as defined above.

Nucleic acid having the nucleotide sequence of SEQ ID NO: 3 corresponds to the wcaJ-gene of *Basfia succiniciproducens*-strain DD1.

According to a preferred embodiment of the modified microorganism according to the present invention, this microorganism is not only characterized by a reduced activity of the enzyme encoded by the wcaJ-gene, but also, compared to the wild-type, by
i) a reduced pyruvate formate lyase activity,
ii) a reduced lactate dehydrogenase activity, or
iii) a reduced pyruvate formate lyase activity and a reduced lactate dehydrogenase activity.

Modified microorganisms being deficient in lactate dehydrogenase and/or being deficient in pyruvate formate lyase activity are disclosed in WO-A-2010/092155, US 2010/

0159543 and WO-A-2005/052135, the disclosure of which with respect to the different approaches of reducing the activity of lactate dehydrogenase and/or pyruvate formate lyase in a microorganism, preferably in a bacterial cell of the genus *Pasteurella*, particular preferred in *Basfia succiniciproducens* strain DD1, is incorporated herein by reference. Methods for determining the pyruvate formate lyase activity are, for example, disclosed by Asanuma N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777 and methods for determining the lactate dehydrogenase activity are, for example, disclosed by Bergmeyer, H. U., Bergmeyer J. and Grassi, M. (1983-1986) in "*Methods of Enzymatic Analysis*", 3$^{rd}$ Edition, Volume III, pages 126-133, Verlag Chemie, Weinheim.

In this context it is preferred that the reduction of the activity of lactate dehydrogenase is achieved by an inactivation of the ldhA-gene (which encodes the lactate dehydrogenase; LdhA; EC 1.1.1.27 or EC 1.1.1.28) and the reduction of the pyruvate formate lyase is achieved by an inactivation of the pflA-gene (which encodes for an activator of pyruvate formate lyase; PflA; EC 1.97.1.4) or the pflD-gene (which encodes the pyruvate formate lyase; PflD; EC 2.3.1.54), wherein the inactivation of these genes (i. e. ldhA, pflA and pflD) is preferably achieved by a deletion of theses genes or parts thereof, by a deletion of a regulatory element of these genes or at least a part thereof of by an introduction of at least one mutation into these genes, particular preferred by means of the "Campbell recombination" as described above.

The ldhA-gene the activity of which is reduced in the modified microorganism according to the present invention preferably comprises a nucleic acid selected from the group consisting of:

α1) nucleic acids having the nucleotide sequence of SEQ ID NO: 10;

α2) nucleic acids encoding the amino acid sequence of SEQ ID NO: 11;

α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2);

α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2);

α5) nucleic acids capable of hybridizing under stringent conditions with a complementary sequence of any of the nucleic acids according to α1) or α2); and α6) nucleic acids encoding the same protein as any of the nucleic acids of α1) or α2), but differing from the nucleic acids of α1) or α2) above due to the degeneracy of the genetic code.

The pflA-gene the activity of which is reduced in the modified microorganism according to the present invention preferably comprises a nucleic acid selected from the group consisting of:

β1) nucleic acids having the nucleotide sequence of SEQ ID NO: 12;

β2) nucleic acids encoding the amino acid sequence of SEQ ID NO: 13;

β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1) or β2), the identity being the identity over the total length of the nucleic acids of β1) or β2);

β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of (31) or (32), the identity being the identity over the total length of amino acid sequence encoded by the nucleic acids of β1) or β2);

β5) nucleic acids capable of hybridizing under stringent conditions with a complementary sequence of any of the nucleic acids according to β1) or β2); and β6) nucleic acids encoding the same protein as any of the nucleic acids of β1) or β2), but differing from the nucleic acids of β1) or β2) above due to the degeneracy of the genetic code.

The pflD-gene the activity of which is reduced in the modified microorganism according to the present invention preferably comprises a nucleic acid selected from the group consisting of:

γ1) nucleic acids having the nucleotide sequence of SEQ ID NO: 14;

γ2) nucleic acids encoding the amino acid sequence of SEQ ID NO: 15;

γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2);

γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2);

γ5) nucleic acids capable of hybridizing under stringent conditions with a complementary sequence of any of the nucleic acids according to γ1) or γ2); and γ6) nucleic acids encoding the same protein as any of the nucleic acids of γ1) or γ2), but differing from the nucleic acids of γ1) or γ2) above due to the degeneracy of the genetic code.

In this context it is preferred that the modified microorganism according to the present invention further comprises:

A) a deletion of the ldhA-gene or at least a part thereof, a deletion of a regulatory element of the ldhA-gene or at least a part thereof or an introduction of at least one mutation into the ldhA-gene;

B) a deletion of the pflD-gene or at least a part thereof, a deletion of a regulatory element of the pflD-gene or at least a part thereof or an introduction of at least one mutation into the pflD-gene;
C) a deletion of the pflA-gene or at least a part thereof, a deletion of a regulatory element of the pflA-gene or at least a part thereof or an introduction of at least one mutation into the pflA-gene;
D) a deletion of the ldhA-gene or at least a part thereof, a deletion of a regulatory element of the ldhA-gene or at least a part thereof or an introduction of at least one mutation into the ldhA-gene
and
   a deletion of the pflD-gene or at least a part thereof, a deletion of a regulatory element of the pflD-gene or at least a part thereof or an introduction of at least one mutation into the pflD-gene;
or
E) a deletion of the ldhA-gene or at least a part thereof, a deletion of a regulatory element of the ldhA-gene or at least a part thereof or an introduction of at least one mutation into the ldhA-gene
and
   a deletion of the pflA-gene or at least a part thereof, a deletion of a regulatory element of the pflA-gene or at least a part thereof or an introduction of at least one mutation into the pflA-gene.

Particular preferred embodiments of the modified microorganisms according to the present invention are:
   modified bacterial cells of the family Pasteurellaceae, in particular preferred of the genus *Basfia* and even more preferred of the species *Basfia succiniciproducens*, in which the wcaJ-gene or at least a part thereof has been deleted or wherein at least one mutation has been introduced in the wcaJ-gene, wherein the introduction of the at least one mutation preferably leads expression of an enzyme in which at least 100 amino acids, preferably at least 125 amino acids, more preferred at least 150 amino acids and most preferred at least 160 amino acids of the wild-type enzyme encoded by the wcaJ-gene are deleted from the C-terminal end;
   modified bacterial cells of the family Pasteurellaceae, in particular preferred of the genus *Basfia* and even more preferred of the species *Basfia succiniciproducens*, in which the wcaJ-gene or at least a part thereof has been deleted or wherein at least one mutation has been introduced in the wcaJ-gene, wherein the introduction of the at least one mutation preferably leads expression of an enzyme in which at least 100 amino acids, preferably at least 125 amino acids, more preferred at least 150 amino acids and most preferred at least 160 amino acids of the wild-type enzyme encoded by the wcaJ-gene are deleted from the C-terminal end, and in which, compared to the wild-type, the activity of the lactate dehydrogenase is reduced, preferably by a modification of the ldhA-gene, in particular by a modification of the ldhA-gene having the nucleic acid sequence according to SEQ ID NO: 10 and encoding for LdhA having the amino acid sequence according to SEQ ID NO: 11;
   modified bacterial cells of the family Pasteurellaceae, in particular preferred of the genus *Basfia* and even more preferred of the species *Basfia succiniciproducens*, in which the wcaJ-gene or at least a part thereof has been deleted or wherein at least one mutation has been introduced in the wcaJ-gene, wherein the introduction of the at least one mutation preferably leads expression of an enzyme in which at least 100 amino acids, preferably at least 125 amino acids, more preferred at least 150 amino acids and most preferred at least 160 amino acids of the wild-type enzyme encoded by the wcaJ-gene are deleted from the C-terminal end, and in which, compared to the wild-type, the activity of the pyruvate formate lyase is reduced, preferably by a modification of the pflA-gene or the pflD-gene, in particular by a modification of the pflA-gene having the nucleic acid sequence according to SEQ ID NO: 12 and encoding for PflA having the amino acid sequence according to SEQ ID NO: 13 or by a modification of the pflD-gene having the nucleic acid sequence according to SEQ ID NO: 14 and encoding for PflD having the amino acid sequence according to SEQ ID NO: 15;
   modified bacterial cells of the family Pasteurellaceae, in particular preferred of the genus *Basfia* and even more preferred of the species *Basfia succiniciproducens*, in which the wcaJ-gene or at least a part thereof has been deleted or wherein at least one mutation has been introduced in the wcaJ-gene, wherein the introduction of the at least one mutation preferably leads expression of an enzyme in which at least 100 amino acids, preferably at least 125 amino acids, more preferred at least 150 amino acids and most preferred at least 160 amino acids of the wild-type enzyme encoded by the wcaJ-gene are deleted from the C-terminal end, and in which, compared to the wild-type, the activity of the lactate dehydrogenase and the pyruvate formate lyase is reduced, preferably by a modification of the ldhA-gene and the pflA-gene, preferably by a modification of the ldhA-gene and the pflA-gene, in particular by a modification of the ldhA-gene having the nucleic acid sequence according to SEQ ID NO: 10 and encoding for LdhA having the amino acid sequence according to SEQ ID NO: 11 or by a modification of the pflA-gene having the nucleic acid sequence according to SEQ ID NO: 12 and encoding for PflA having the amino acid sequence according to SEQ ID NO: 13, or a modification of the ldhA-gene and the pflD-gene, in particular by a modification of the ldhA-gene having the nucleic acid sequence according to SEQ ID NO: 10 and encoding for LdhA having the amino acid sequence according to SEQ ID NO: 11 or by a modification of the pflD-gene having the nucleic acid sequence according to SEQ ID NO: 14 and encoding for PflD having the amino acid sequence according to SEQ ID NO: 15.

A contribution to solving the problems mentioned at the outset is furthermore provided by a method of producing an organic compound comprising:
I) cultivating the modified microorganism according to the present invention in a culture medium comprising at least one assimilable carbon source to allow the modified microorganism to produce the organic compound, thereby obtaining a fermentation broth comprising the organic compound;
II) recovering the organic compound from the fermentation broth obtained in process step I).

In process step I) the modified microorganism according to the present invention is cultured in a culture medium comprising at least one assimilable carbon source to allow the modified microorganism to produce the organic compound, thereby obtaining a fermentation broth comprising the organic compound. Preferred organic compounds that can be produced by the process according to the present invention comprise carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof, tricarboxylic acids such as citric acid or salts thereof, alcohols such as methanol or ethanol, amino acids such as L-asparagine, L-aspartic acid, L-arginine, L-isoleucine, L-glycine, L-glutamine, L-glutamic acid, L-cysteine, L-serine, L-tyrosine, L-tryptophan, L-threonine, L-valine, L-histidine, L-proline, L-methionine, L-lysine, L-leucine, etc.

According to a preferred embodiment of the process according to the present invention the organic compound is succinic acid. The term "succinic acid", as used in the context of the present invention, has to be understood in its broadest sense and also encompasses salts thereof (i. e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The modified microorganism according to the present invention is, preferably, incubated in the culture medium at a temperature in the range of about 10 to 60° C. or 20 to 50° C. or 30 to 45° C. at a pH of 5.0 to 9.0 or 5.5 to 8.0 or 6.0 to 7.0.

Preferably, the organic compound, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably selected from sucrose, maltose, maltotriose, maltotetraose, maltopentaose, maltohexaose, maltoheptaose, D-fructose, D-glucose, D-xylose, L-arabinose, D-galactose, D-mannose, glycerol and mixtures thereof or compositions containing at least one of said compounds, or is selected from decomposition products of starch, cellulose, hemicellulose and/or lignocellulose. Preferably, the assimilable carbon source comprises D-glucose, maltose, sucrose, glycerol or a mixture of at least two of these compounds, wherein mixtures of glycerol and D-glucose, glycerol and sucrose, glycerol and D-xylose, glycerol and maltose and D-glucose and fructose are particularly preferred.

The initial concentration of the assimilable carbon source is, preferably adjusted to a value in a range of 5 to 100 g/l, preferably 5 to 75 g/l and more preferably 5 to 50 g/l and may be maintained in said range during cultivation. The pH of the reaction medium may be controlled by addition of suitable bases as for example, gaseous ammonia, $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, CaO, $CH_6N_2O_2$, $C_2H_7N$ and/or mixtures thereof. These alkaline neutralization agents are especially required if the organic compounds that are formed in the course of the fermentation process are carboxylic acids or dicarboxylic acids. In the case of succinic acid as the organic compound, $Mg(OH)_2$ and $MgCO_3$ area particular preferred bases.

The fermentation step I) according to the present invention can, for example, be performed in stirred fermenters, bubble columns and loop reactors. A comprehensive overview of the possible method types including stirrer types and geometric designs can be found in Chmiel: "*Bio-prozesstechnik: Einführung in die Bioverfahrenstechnik*", Volume 1. In the process according to the present invention, typical variants available are the following variants known to those skilled in the art or explained, for example, in Chmiel, Hammes and Bailey: "Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic acid, especially succinic acid, in process step I) are:
Assimilable carbon source: glycerol, sucrose, D-glucose, maltose, glycerol+D-glucose, glycerol+sucrose, glycerol+maltose, glycerol+D-xylose, D-glucose+fructose
Temperature: 30 to 45° C.
pH: 5.5 to 7.0
Supplied gas: $CO_2$ It is furthermore preferred in process step I) that the assimilable carbon source is converted to the organic compound, preferably to succinic acid, with a carbon yield YP/S of at least 0.5 g/g up to about 1.28 g/g; as for example a carbon yield YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.1 g/g, of at least 1.15 g/g, of at least 1.20 g/g, of at least 1.22 g/g, or of at least 1.24 g/g (organic compound/carbon, preferably succinic acid/carbon).

It is furthermore preferred in process step I) that the assimilable carbon source is converted to the organic compound, preferably to succinic acid, with a specific productivity yield of at least 0.6 g g $DCW^{-1}$ $h^{-1}$ organic compound, preferably succinic acid, or of at least of at least 0.65 g g $DCW^{-1}$ $h^{-1}$, of at least 0.7 g g $DCW^{-1}$ $h^{-1}$, of at least 0.75 g g $DCW^{-1}$ $h^{-1}$ or of at least 0.77 g g $DCW^{-1}$ $h^{-1}$ organic compound, preferably succinic acid.

It is furthermore preferred in process step I) that the assimilable carbon source is converted to the organic compound, preferably to succinic acid, with a space time yield for the organic compound, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic compound, preferably succinic acid. According to another preferred embodiment of the process according to the present invention in process step I) the modified microorganism is converting at least 20 g/L, more preferably at least 25 g/l and even more preferably at least 30 g/l of the assimilable carbon source, preferably an assimilable carbon source selected from sucrose, maltose, D-fructose, D-glucose, D-xylose, L-arabinose, D-galactose, D-mannose, and/or glycerol, to at least 20 g/l, more preferably to at least 25 g/l and even more preferably at least 30 g/l of the organic compound, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic compound produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g $DCW^{-1}$ $h^{-1}$). The space-time-yield (STY) is defined as the ratio of the total amount of organic compound formed in the fermentation process to the volume of the culture, regarded over the entire time of cultivation. The space-time yield is also known as the "volumetric productivity".

In process step II) the organic compound, preferably succinic acid, is recovered from the fermentation broth obtained in process step I).

Usually, the recovery process comprises the step of separating the recombinant microorganims from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic compound, preferably succinic acid, is further purified. If, however, the organic compound is converted into a secondary organic product by chemical reactions as described below, a further purification of the organic compound is, depending on the kind of reaction and the reaction conditions, not necessarily required. For the purification of the organic compound obtained in process step II), preferably for the purification of succinic acid, methods known to the person skilled in the art can be used, as for example crystallization, filtration, electrodialysis and chromatography. In the case of succinic acid as the organic compound, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove un-desired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i. e. succinic acid), which subsequently can be crystallized by cooling down the acidified medium. Examples of further suitable purification processes are disclosed in EP-A-1 005 562, WO-A-2008/010373, WO-A-2011/082378, WO-A-2011/043443, WO-A-2005/030973, WO-A-2011/123268 and WO-A-2011/064151 and EP-A-2 360 137.

According to a preferred embodiment of the process according to the present invention the process further comprises the process step:

III) conversion of the organic compound contained in the fermentation broth obtained in process step I) or conversion of the recovered organic compound obtained in process step II) into a secondary organic product being different from the organic compound by at least one chemical reaction.

In case of succinic acid as the organic compound preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:

b1) either the direct catalytic hydrogenation of the succinic acid obtained in process steps I) or II) to THF and/or BDO and/or GBL or b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:

b) the chemical conversion of succinic acid ammonium salts obtained in process steps I) or II) to pyrrolidones in a manner known per se.

For details of preparing these compounds reference is made to US-A-2010/0159543 and WO-A-2010/092155.

A contribution to solving the problems mentioned at the outset is furthermore provided by the use of the modified microorganism according to the present invention for the fermentative production of organic compounds. Preferred organic compounds are those compounds that have already been mentioned in connection with the process according to the present invention, succinic acid being the most preferred organic compound. Furthermore, preferred conditions for the fermentative production of organic compounds, preferably, of succinic acid, are those conditions that have already been described in connection with process step I) of the process according to the present invention.

The invention is now explained in more detail with the aid of figures and non-limiting examples.

EXAMPLES

Example 1: General Method for the Transformation of *Basfia succiniciproducens*

TABLE 1

Nomenclature of the DD1-wild-type
and mutants referred to in the examples

Strain

Wild-type DD1 (deposit DSM18541)
DD1 ΔwcaJ
DD1 ΔldhA
DD1 ΔldhA ΔpflD
DD1 ΔldhA ΔpflD ΔwcaJ
DD1 ΔldhA ΔpflA
DD1 ΔldhA ΔpflA ΔwcaJ

*Basfia succiniciproducens* DD1 (wild-type) was transformed with DNA by electroporation using the following protocol:

For preparing a pre-culture DD1 was inoculated from frozen stock into 40 ml BHI (brain heart infusion; Becton, Dickinson and Company) in 100 ml shake flask. Incubation was performed over night at 37° C.; 200 rpm. For preparing the main-culture 100 ml BHI were placed in a 250 ml shake flask and inoculated to a final OD (600 nm) of 0.2 with the pre-culture. Incubation was performed at 37° C., 200 rpm. The cells were harvested at an OD of approximately 0.5, 0.6 and 0.7, pellet was washed once with 10% cold glycerol at 4° C. and re-suspended in 2 ml 10% glycerol (4° C.).

100 μl of competent cells were the mixed with 2-8 μg Plasmid-DNA and kept on ice for 2 min in an electroporation cuvette with a width of 0.2 cm. Electroporation under the following conditions: 400 Ω; 25 μF; 2.5 kV (Gene Pulser, Bio-Rad). 1 ml of chilled BHI was added immediately after electroporation and incubation was performed for approximately 2 h at 37° C.

Cells were plated on BHI with 5 mg/L chloramphenicol and incubated for 2-5 d at 37° C. until the colonies of the transformants were visible. Clones were isolated and restreaked onto BHI with 5 mg/l chloramphenicol until purity of clones was obtained.

Example 2: Generation of Deletion Constructs

Figure 1:
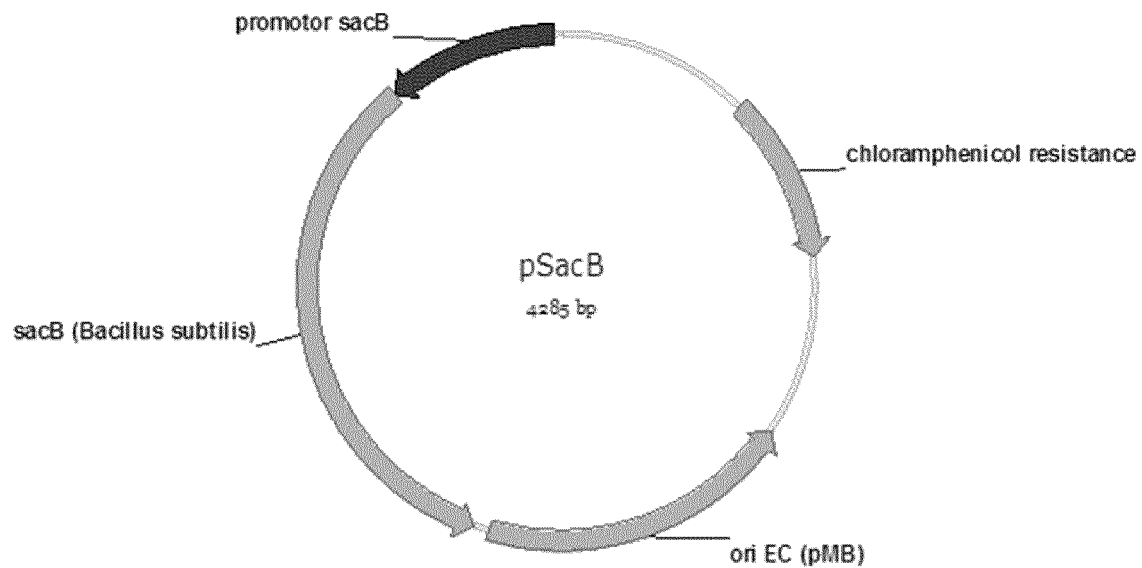
FIG. 1 shows a schematic map of plasmid pSacB (SEQ ID NO: 5).
Figure 2:
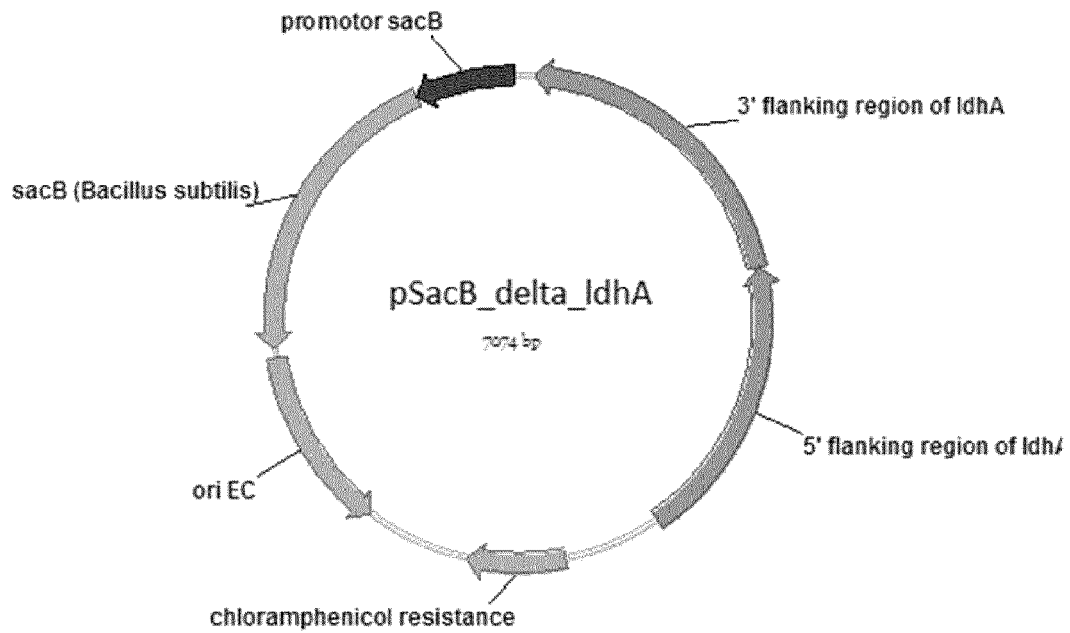
FIG. 2 shows a schematic map of plasmid pSacB ΔldhA (SEQ ID NO: 6).
Figure 3:
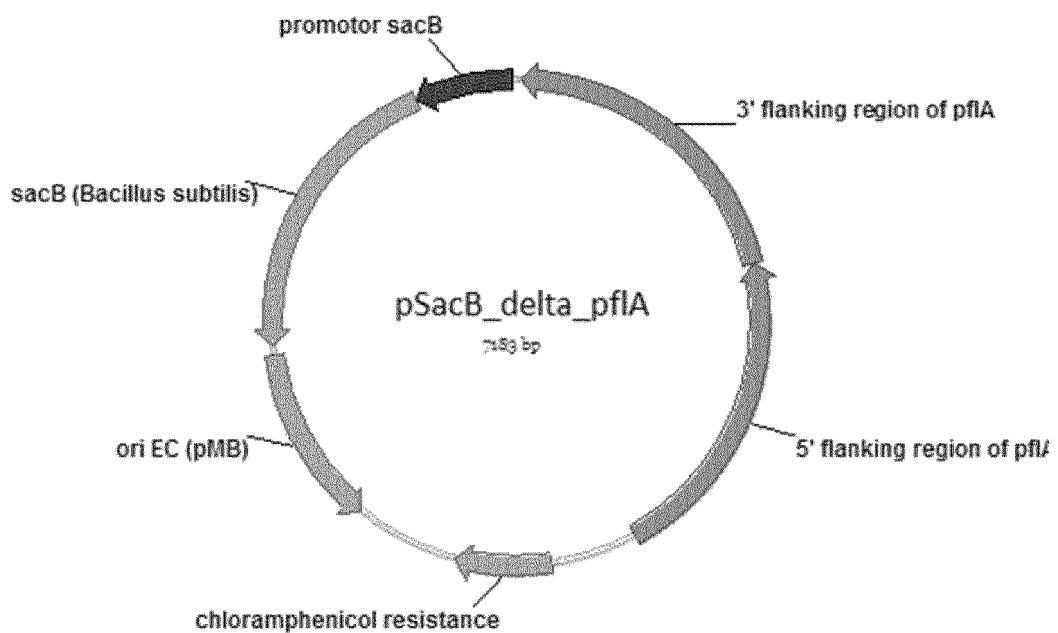
FIG. 3 shows a schematic map of plasmid pSacB ΔpflA (SEQ ID NO: 7).
Figure 4:
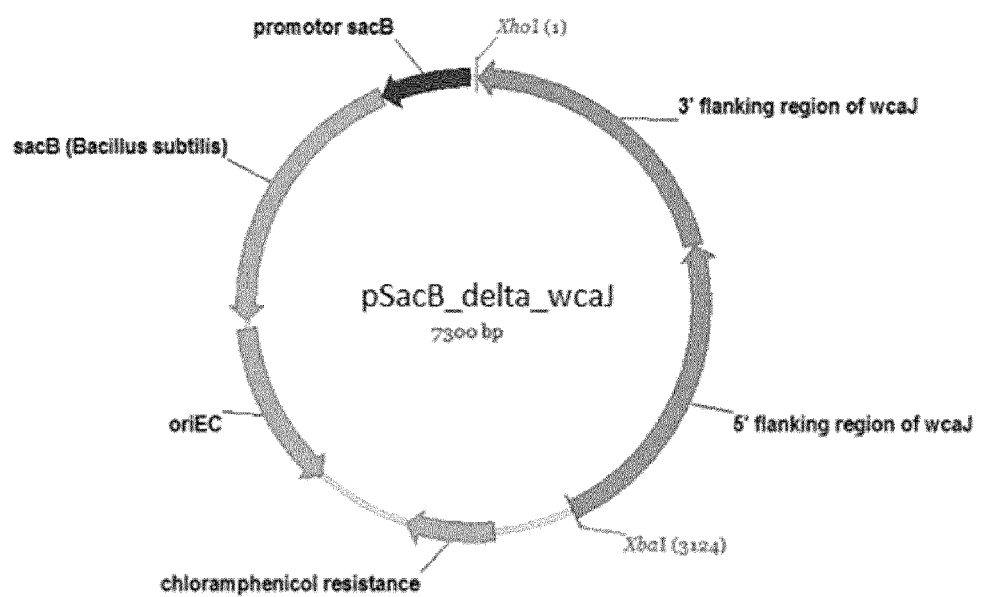
FIG. 4 shows a schematic map of plasmid pSacB ΔwcaJ (SEQ ID NO: 8).
Figure 5:
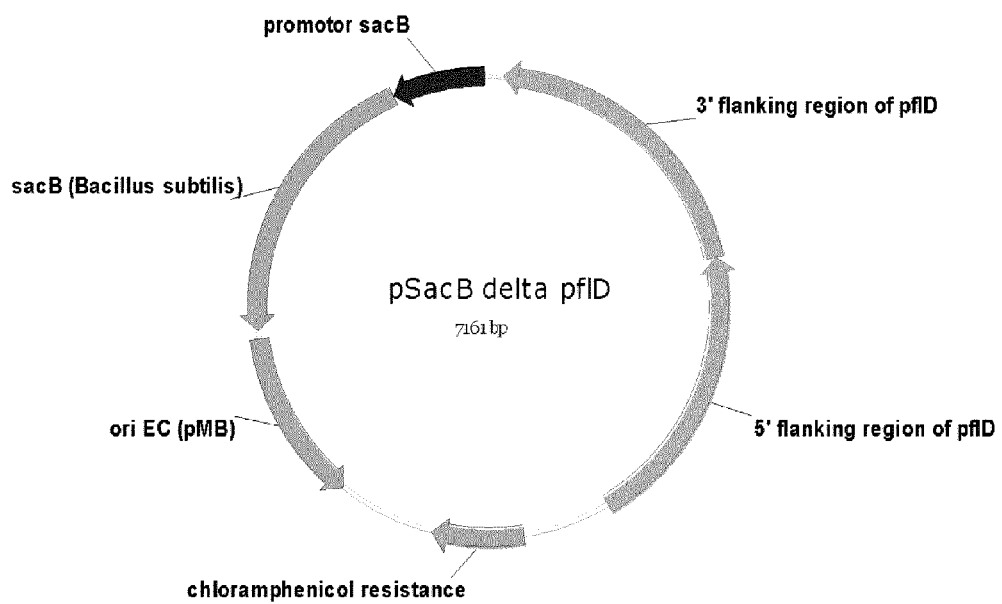
FIG. 5 shows a schematic map of plasmid pSacB ΔpflD (SEQ ID NO: 9).
Figure 6:
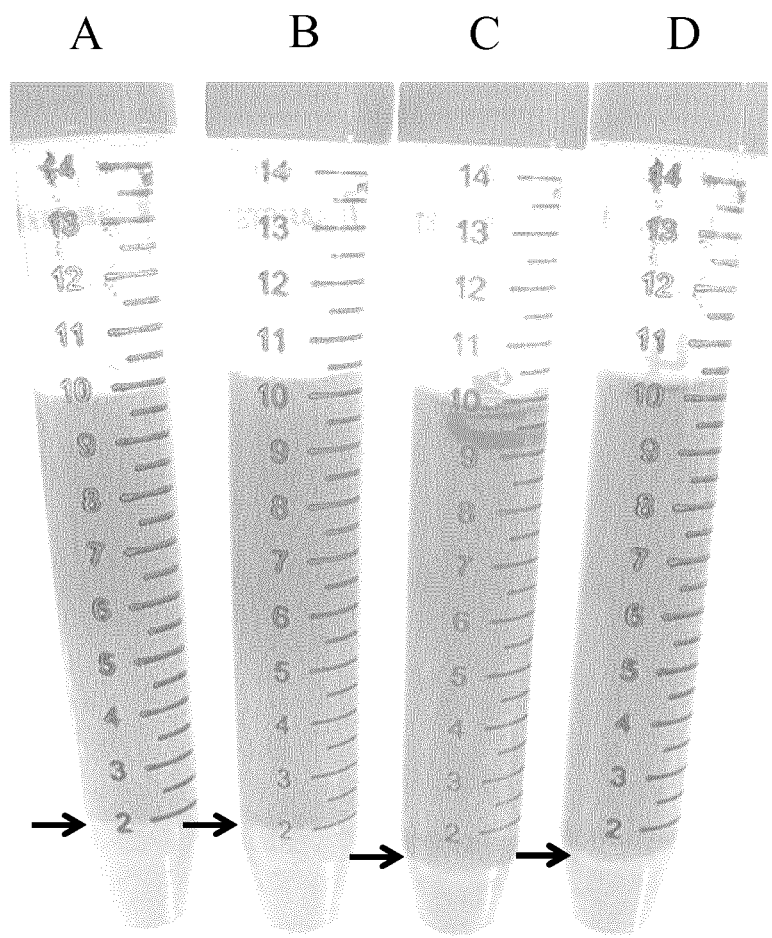
FIG. 6 shows a pellet of cells as obtained by sedimentation of different culture media.

Mutation/deletion plasmids were constructed based on the vector pSacB (SEQ ID NO: 5). FIG. 1 shows a schematic map of plasmid pSacB. 5'- and 3'-flanking regions (approx. 1500 bp each) of the chromosomal fragment, which should be deleted were amplified by PCR from chromosomal DNA of *Basfia succiniciproducens* and introduced into said vector using standard techniques. Normally, at least 80% of the ORF were targeted for a deletion. In such a way, the deletion plasmids for the lactate dehydrogenase ldhA, pSacB_delta_ldhA (SEQ ID NO: 6), the pyruvate formate lyase activating enzyme pflA, pSacB_delta_pflA (SEQ ID No: 7), the putative fructose-specific transporter wcaJ, pSacB_delta_wcaJ (SEQ ID No: 8) and pyruvate formate lyase pflD, pSacB_delta_ pflD (SEQ ID No: 9) were constructed. FIGS. 2, 3, 4 and 5 show schematic maps of plasmid pSacB_delta_ldhA, pSacB_delta_pflA, pSacB_delta_wcaJ and pSacB_delta_pflD, respectively.

In the plasmid sequence of pSacB (SEQ ID NO: 5) the sacB-gene is contained from bases 2380-3801. The sacB-promotor is contained from bases 3802-4264. The chloramphenicol gene is contained from base 526-984. The origin of replication for *E. coli* (ori EC) is contained from base 1477-2337 (see FIG. 1).

In the plasmid sequence of pSacB_delta_ldhA (SEQ ID NO: 6) the 5' flanking region of the ldhA gene, which is homologous to the genome of *Basfia succiniciproducens*, is contained from bases 1519-2850, while the 3' flanking region of the ldhA-gene, which is homologous to the genome of *Basfia succiniciproducens*, is contained from bases 62-1518. The sacB-gene is contained from bases 5169-6590. The sacB-promoter is contained from bases 6591-7053. The chloramphenicol gene is contained from base 3315-3773. The origin of replication for *E. coli* (ori EC) is contained from base 4266-5126 (see FIG. 2).

In the plasmid sequence of pSacB_delta_pflA (SEQ ID NO: 7) the 5' flanking region of the OA-gene, which is homologous to the genome of *Basfia succiniciproducens*, is contained from bases 1506-3005, while the 3' flanking region of the pflA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 3).

In the plasmid sequence of pSacB_delta_wcaJ (SEQ ID NO: 8) the 5' flanking region of the wcaJ gene, which is homologous to the genome of *Basfia succiniciproducens*, is contained from bases 1506-3122, while the 3' flanking region of the wcaJ-gene, which is homologous to the genome of *Basfia succiniciproducens*, is contained from bases 6-1505. The sacB-gene is contained from bases 5395-6816. The sacB-promoter is contained from bases 6817-7279. The chloramphenicol gene is contained from base 3541-3999. The origin of replication for *E. coli* (ori EC) is contained from base 4492-5352 (see FIG. 4).

In the plasmid sequence of pSacB_delta_pflD (SEQ ID NO: 9) the 5' flanking region of the pflD-gene, which is homologous to the genome of *Basfia succiniciproducens*, is contained from bases 1533-2955, while the 3' flanking region of the pflD-gene, which is homologous to the genome of *Basfia succiniciproducens*, is contained from bases 62-1532. The sacB-gene is contained from bases 5256-6677. The sacB-promoter is contained from bases 6678-7140. The chloramphenicol gene is contained from base 3402-3860. The origin of replication for *E. coli* (ori EC) is contained from base 4353-5213 (see FIG. 5).

Example 3: Generation of Improved Succinate Producing Strains a) *Basfia succiniciproducens* DD1 was transformed as described above with the pSacB_delta_ldhA and "Campbelled in" to yield a "Campbell in" strain. Transformation and integration into the genome of *Basfia succiniciproducens* was confirmed by PCR yielding bands for the integrational event of the plasmid into the genome of *Basfia* succiniciproducens.

The "Campbell in" strain was then "Campbelled out" using agar plates containing sucrose as a counter selection medium, selecting for the loss (of function) of the sacB gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB-evan-sucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.

The "Campbelled out" strains containing the mutation/deletion of the ldhA-gene were confirmed by chloramphenicol sensitivity. The mutation/deletion mutants among these strains were identified and confirmed by PCR analysis. This led to the ldhA-deletion mutant *Basfia succiniciproducens* DD1 ΔldhA.

b) *Basfia succiniciproducens* DD1 ΔldhA was transformed with pSacB_delta_pflD as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflD-double deletion mutant *Basfia succiniciproducens* DD1 ΔldhA ΔpflD.

c) *Basfia succiniciproducens* DD1 ΔldhA ΔpflD was transformed with pSacB_delta_wcaJ as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflD wcaJ-triple deletion mutant *Basfia succiniciproducens* DD1 ΔldhA ΔpflD ΔwcaJ.

d) *Basfia succiniciproducens* DD1 ΔldhA was transformed with pSacB_delta_pflA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflA-double deletion mutant *Basfia succiniciproducens* DD1 ΔldhA ΔpflA.

e) *Basfia succiniciproducens* DD1 ΔldhA ΔpflA was transformed with pSacB_delta_wcaJ as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA pflA wcaJ-triple deletion mutant *Basfia succiniciproducens* DD1 ΔldhA ΔpflA ΔwcaJ.

f) *Basfia succiniciproducens* DD1 was transformed with pSacB_delta_wcaJ as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the wcaJ-deletion mutant *Basfia succiniciproducens* DD1 ΔwcaJ.

Example 4: Cultivation of Various DD1-Strains on Glucose and Sucrose

The productivity of the DD1 was compared with the productivity of the mutant strain DD1 ΔwcaJ in the presence of glucose or sucrose as a carbon source.

The productivity of the DD1 ΔldhA ΔpflD was compared with the productivity of the mutant strain DD1 ΔldhA ΔpflD ΔwcaJ in the presence of glucose or sucrose as a carbon source.

The productivity of the DD1 ΔldhA ΔpflA was compared with the productivity of the mutant strain DD1 ΔldhA ΔpflA ΔwcaJ in the presence of glucose or sucrose as a carbon source.

Productivity was analyzed utilizing media and incubation conditions described below.

1. Medium Preparation

The composition and preparation of the cultivation medium is as described in the following table 2, 3, 4 and 5.

TABLE 2

Composition of trace element solution.
Trace element solution

| Compound | Final concentration |
|---|---|
| citric acid | 3.5 g/L |
| $ZnSO_4 \times 7\ H_2O$ | 1851 mg/L |
| $CaSO_4 \times 2\ H_2O$ | 10 mg/L |
| $FeSO_4 \times 7\ H_2O$ | 2040 mg/L |
| $CaCl_2 \times 2\ H_2O$ | 12460 mg/L |
| $MnCl_2 \times 4\ H_2O$ | 1200 mg/L |
| $Na_2MoO_4 \times 2\ H_2O$ | 38 mg/L |
| $CuCl_2 \times 2\ H_2O$ | 188 mg/L |
| $NiCl_2 \times 6\ H_2O$ | 32 mg/L |
| $CoCl_2 \times 6\ H_2O$ | 101 mg/L |

TABLE 3

Composition of vitamin solution.
Vitamin solution

| Compound | Final concentration |
|---|---|
| Thiamin HCl (B1) | 500 mg/L |
| Nicotinic acid (B3) | 500 mg/L |
| Riboflavin (B2) | 20 mg/L |
| Biotin (B7) | 5 mg/L |
| Pantothenic acid (B5) | 100 mg/L |
| Pyridoxine (B6) | 500 mg/L |
| Cyanocobalamin (B12) | 5 mg/L |
| Lipoic acid | 5 mg/L |

TABLE 4

Composition of LSM medium for cultivation on glucose.

| Compound | Volume/Mass | Stock concentration | Final concentration |
|---|---|---|---|
| Medium 1 | | | |
| $MgCO_3$ | 2.5 g | 100% | 50.00 g/L |
| Water | 28 mL | — | — |
| Medium 2 | | | |
| Succinic acid | 2.5 mL | 50 g/L | 2.50 g/L |
| Glucose | 4.00 mL | 650 g/L | 52.00 g/L |
| $(NH_4)_2SO_4$ | 0.25 mL | 500 g/L | 2.50 g/L |
| $(NH_4)_2HPO_4$ | 0.5 mL | 200 g/L | 2.00 g/L |
| $K_2CO_3$ | 0.50 mL | 200 g/L | 2.00 g/L |
| $KH_2PO_4$ | 0.50 mL | 100 g/L | 1.00 g/L |
| $Na_2CO_3$ | 0.50 mL | 200 g/L | 2.00 g/L |
| vitamin solution | 0.50 mL | 25 g/L | 0.25 g/L |
| trace element solution | 0.50 mL | 21 g/L | 0.21 g/L |

TABLE 5

Composition of LSM medium for cultivation on sucrose.

| Compound | Volume/Mass | Stock concentration | Final concentration |
|---|---|---|---|
| Medium 1 | | | |
| $MgCO_3$ | 2.5 g | 100% | 50.00 g/L |
| Water | 28 mL | — | — |
| Medium 2 | | | |
| Succinic acid | 2.5 mL | 50 g/L | 2.50 g/L |
| Sucrose | 3.85 mL | 650 g/L | 50.00 g/L |
| $(NH_4)_2SO_4$ | 0.25 mL | 500 g/L | 2.50 g/L |
| $(NH_4)_2HPO_4$ | 0.5 mL | 200 g/L | 2.00 g/L |
| $K_2CO_3$ | 0.50 mL | 200 g/L | 2.00 g/L |
| $KH_2PO_4$ | 0.50 mL | 100 g/L | 1.00 g/L |
| $Na_2CO_3$ | 0.50 mL | 200 g/L | 2.00 g/L |
| vitamin solution | 0.50 mL | 25 g/L | 0.25 g/L |
| trace element solution | 0.50 mL | 21 g/L | 0.21 g/L |

2. Cultivations and Analytics

For growing the main culture bacteria from a freshly grown BHI-agar plate was used to inoculate to OD600=0.75 a 100 ml-serum bottle with gas tight butyl rubber stopper containing 50 ml of the liquid medium described in table 2 and 3 with a $CO_2$-atmosphere. The bottles were incubated at 37° C. and 160 rpm (shaking diameter: 2.5 cm). Consumption of the C-sources and production of carboxylic acids was quantified via HPLC (HPLC methods are described in table 10 and 11) after 24 h or 48 h. Cell growth was measured by measuring the absorbance at 600 nm (OD600) using a spectrophotometer (Ultrospec3000, Amersham Biosciences, Uppsala Sweden).

3. Results

The results of the cultivation experiments with different DD1-strains are shown in table 6, 7 and 8. As can be seen from these results, a reduction of the activity of the enzyme that is encoded by the ΔwcaJ-cell leads to increased production of succinic acid.

Moreover, samples obtained by cultivation of the DD1 ΔldhA ΔpflD/DD1 ΔldhA ΔpflA-strain and the DD1ΔldhA ΔpflD ΔwcaJ/DD1ΔldhA ΔpflA ΔwcaJ-strain after 24 h or 48 h of incubation have been transferred into a 15 ml tube to measure supernatant volumes obtained after centrifugation. As shown in table 9, a reduction of the activity of the enzyme that is encoded by the ΔwcaJ-cell leads to modified microorganisms that show a significantly improved sedimentation behavior (a denser cell pellet is obtained after centrifugation) and that can thus easier be removed from the culture medium in the subsequent purification process.

TABLE 6

Cultivation of the DD1 and the DD1 ΔwcaJ-strain on glucose and sucrose.

| | DD1 | DD1ΔwcaJ | DD1 | DD1ΔwcaJ |
|---|---|---|---|---|
| substrate | glucose | glucose | sucrose | sucrose |
| tc [h]$^a$ | 24 | 24 | 48 | 48 |
| $\Delta C_{substrate}$ [g/l]$^b$ | 48.4 | 48.4 | 48.6 | 48.1 |
| $\Delta C_{SA}$[g/l]$^c$ (succinic acid) | 26.1 | 28.2 | 22.0 | 24.3 |
| $\Delta C_{LA}$ [g/L]$^{c,h}$ (lactic acid) | 5.1 | 3.3 | 11.8 | 10.0 |
| $\Delta C_{FA}$[g/l]$^{c,h}$ (formic acid) | 4.8 | 4.2 | 4.1 | 4.2 |
| $\Delta C_{AA}$[g/l]$^{c,h}$ (acetic acid) | 7.2 | 7.2 | 6.2 | 6.9 |
| $\Delta C_{PA}$[g/l]$^{c,h}$ (pyruvic acid) | 0.0 | 0.0 | 0.0 | 0.0 |
| $\Delta C_{P}$[g/l]$^{c,h}$ (propionic acid) | 0.0 | 0.0 | 0.0 | 0.0 |
| $\Delta C_{E}$[g/l]$^c$ (ethanol) | 0.3 | 0.2 | 0.3 | 0.2 |
| SA Yield (SA/S) [g/g]$^g$ | 0.54 | 0.58 | 0.45 | 0.50 |

$^a$cultivation time
$^b$consumption of substrate (glucose or sucrose)
$^c$formation of succinic acid, lactic acid, formic acid, acetic acid, pyruvic acid, propionic acid and ethanol
$^g$SA yield (ration of SA per consumed substrate)
$^h$Detection limits for acetic acid, lactic acid, malic acid, and formic acid were found to be lower than 0.01 g/l in the given HPLC method

TABLE 7

Cultivation of the DD1 ΔldhA ΔpflD-strain and the DD1 ΔldhA ΔpflD ΔwcaJ-strain on glucose and sucrose.

| | DD1 ΔldhAΔpflD | DD1 ΔldhA ΔpflDΔwcaJ | DD1 ΔldhAΔpflD | DD1 ΔldhA ΔpflDΔwcaJ |
|---|---|---|---|---|
| substrate | glucose | glucose | sucrose | sucrose |
| tc [h]$^a$ | 24 | 24 | 48 | 48 |
| $\Delta C_{substrate}$ [g/l]$^b$ | 49.95 | 49.95 | 50.40 | 50.40 |
| $\Delta C_{SA}$[g/l]$^c$ (succinic acid) | 31.45 | 32.80 | 28.82 | 36.94 |
| $\Delta C_{LA}$ [g/L]$^{c,h}$ (lactic acid) | 0.22 | 0.16 | 0.35 | 0.22 |
| $\Delta C_{FA}$[g/l]$^{c,h}$ (formic acid) | 0.00 | 0.00 | 0.00 | 0.00 |
| $\Delta C_{AA}$[g/l]$^{c,h}$ (acetic acid) | 2.89 | 4.48 | 1.39 | 5.45 |
| $\Delta C_{PA}$[g/l]$^{c,h}$ (pyruvic acid) | 1.87 | 0.94 | 2.70 | 0.23 |
| $\Delta C_{P}$[g/l]$^{c,h}$ (propionic acid) | 0.00 | 0.00 | 0.00 | 0.00 |
| $\Delta C_{E}$[g/l]$^c$ (ethanol) | 0.00 | 0.00 | 0.00 | 0.00 |
| SA Yield (SA/S) [g/g]$^g$ | 0.63 | 0.66 | 0.57 | 0.73 |

$^a$cultivation time
$^b$consumption of substrate (glucose or sucrose)
$^c$formation of succinic acid, lactic acid, formic acid, acetic acid, pyruvic acid, propionic acid and ethanol
$^g$SA yield (ration of SA per consumed substrate)
$^h$Detection limits for acetic acid, lactic acid, malic acid, and formic acid were found to be lower than 0.01 g/l in the given HPLC method

TABLE 8

Cultivation of the DD1 ΔldhA ΔpflA-strain and the DD1 ΔldhA ΔpflA ΔwcaJ-strain on glucose and sucrose

| | DD1 ΔldhAΔpflA | DD1 ΔldhA ΔpflAΔwcaJ | DD1 ΔldhAΔpflA | DD1 ΔldhA ΔpflAΔwcaJ |
|---|---|---|---|---|
| substrate | glucose | glucose | sucrose | sucrose |
| tc [h]$^a$ | 24 | 24 | 48 | 48 |
| $\Delta C_{substrate}$ [g/l]$^b$ | 49.95 | 49.95 | 50.40 | 50.40 |
| $\Delta C_{SA}$[g/l]$^c$ (succinic acid) | 32.37 | 31.77 | 29.36 | 31.36 |
| $\Delta C_{LA}$ [g/L]$^{c,h}$ (lactic acid) | 0.23 | 0.28 | 0.37 | 0.37 |
| $\Delta C_{FA}$[g/l]$^{c,h}$ (formic acid) | 0.00 | 0.00 | 0.00 | 0.00 |
| $\Delta C_{AA}$[g/l]$^{c,h}$ (acetic acid) | 2.68 | 2.40 | 0.90 | 1.87 |
| $\Delta C_{PA}$[g/l]$^{c,h}$ (pyruvic acid) | 1.96 | 2.05 | 3.16 | 2.49 |
| $\Delta C_{P}$[g/l]$^{c,h}$ (propionic acid) | 0.00 | 0.00 | 0.00 | 0.00 |
| $\Delta C_{E}$[g/l]$^c$ (ethanol) | 0.00 | 0.00 | 0.00 | 0.00 |
| SA Yield (SA/S) [g/g]$^g$ | 0.65 | 0.64 | 0.58 | 0.62 |

$^a$cultivation time
$^b$consumption of substrate (glucose or sucrose)
$^c$formation of succinic acid, lactic acid, formic acid, acetic acid, pyruvic acid, propionic acid and ethanol
$^g$SA yield (ration of SA per consumed substrate)
$^h$Detection limits for acetic acid, lactic acid, malic acid, and formic acid were found to be lower than 0.01 g/l in the given HPLC method

TABLE 9

Supernatant volumes obtained after centrifugation (4,600 rpm, 10 min) of 10 mL of bacterial cultures.

| Strain | Substrate | Cultivation time | Supernatant volume |
|---|---|---|---|
| DD1 ΔldhA ΔpflD | glucose | 24 h | 8.0 mL |
| DD1 ΔldhA ΔpflD ΔwcaJ | glucose | 24 h | 8.8 mL |
| DD1 ΔldhA ΔpflA | glucose | 24 h | 8.0 mL |
| DD1 ΔldhA ΔpflA ΔwcaJ | glucose | 24 h | 8.4 mL |
| DD1 ΔldhA ΔpflD | sucrose | 48 h | 8.3 mL |
| DD1 ΔldhA ΔpflD ΔwcaJ | sucrose | 48 h | 9.0 mL |
| DD1 ΔldhA ΔpflA | sucrose | 48 h | 8.3 mL |
| DD1 ΔldhA ΔpflA ΔwcaJ | sucrose | 48 h | 8.6 mL |

TABLE 10

HPLC method (ZX-THF50) for analysis of glucose, succinic acid, formic acid, lactic acid, acetic acid, pyruvic acid and ethanol

| HPLC column | Aminex HPX-87 H, 300 × 7.8 mm (BioRad) | | | |
|---|---|---|---|---|
| Precolumn | Cation H | | | |
| Temperature | 50° C. | | | |
| Eluent flow rate | 0.50 ml/min | | | |
| Injection volume | 5.0 μl | | | |
| Diode array detector | RI-Detector | | | |
| Runtime | 28 min | | | |
| max. pressure | 140 bar | | | |
| Eluent A | 5 mM $H_2SO_4$ | | | |
| Eluent B | 5 mM $H_2SO_4$ | | | |
| Gradient | Time [min] | A[%] | B[%] | Flow [ml/min] |
| | 0.0 | 50 | 50 | 0.50 |
| | 28.0 | 50 | 50 | 0.50 |

TABLE 11

HPLC method (Fast-CH) for analysis of glucose and sucrose

| HPLC column | Fast Carbohydrate, 100 × 7.8 mm (Biorad) | | | |
|---|---|---|---|---|
| Precolumn | Deashing Refill Cartridges (30° C.) | | | |
| Temperature | 75° C. | | | |
| Eluent flow rate | 1.00 ml/min | | | |
| Injection volume | 1.0 μl | | | |
| Diode array detector | RI-Detector | | | |
| Runtime | 8 min | | | |
| max. pressure | 150 bar | | | |
| Eluent A | water | | | |
| Eluent B | water | | | |
| Gradient | Time [min] | A[%] | B[%] | Flow [ml/min] |
| | 0.0 | 50 | 50 | 1.00 |
| | 8.0 | 50 | 50 | 1.00 |

SEQUENCES (nucleotide sequence of 16 S rDNA of strain DD1)

SEQ ID NO: 1 tttgatcctggctcagattgaacgctggcggcaggcttaacacatgcaagtcgaacggtagcgggaggaaagcttgctttctttgccga cgagtggcggacgggtgagtaatgcttggggatctggcttatggagggggataacgacgggaaactgtcgctaataccgcgtaatat cttcggattaaagggtgggactttcgggccacccgccataagatgagcccaagtgggattaggtagttggtggggtaaaggcctacc aagccgacgatctctagctggtctgagaggatgaccagccacactggaactgagacacggtccagactcctacgggaggcagca gtggggaatattgcacaatgggggaaccctgatgcagccatgccgcgtgaatgaagaaggccttcgggttgtaaagttctttcggtg acgaggaaggtgtttgttttaataggacaagcaattgacgttaatcacagaagaagcaccggctaactccgtgccagcagccgcggt aatacgagggtgcgagcgttaatcggaataactgggcgtaaagggcatgcaggcggacttttaagtgagatgtgaaagcccgg gcttaacctgggaattgcatttcagactgggagtctagagtactttagggaggggtagaattccacgtgtagcggtgaaatgcgtagag atgtggaggaataccgaaggcgaaggcagcccccttgggaagatactgacgctcatatgcgaaagcgtggggagcaaacaggatt agataccctggtagtccacgcggtaaacgctgtcgatttggggattgggcttaggcctggtgctcgtagctaacgtgataaatcgacc gcctggggagtacggccgcaaggttaaaactcaaatgaattgacggggcccgcacaagcggtggagcatgtggtttaattcgatg -continued

```
caacgcgaagaaccttacctactcttgacatccagagaatcctgtagagatacgggagtgccttcgggagctctgagacaggtgctg
catggctgtcgtcagctcgtgttgtgaaatgttgggttaagtcccgcaacgagcgcaacccttatcctttgttgccagcatgtaaagatgg
gaactcaaaggagactgccggtgacaaaccggaggaaggtggggatgacgtcaagtcatcatggcccttacgagtagggctaca
cacgtgctacaatggtgcatacagagggcggcgataccgcgaggtagagcgaatctcagaaagtgcatcgtagtccggattggagt
ctgcaactcgactccatgaagtcggaatcgctagtaatcgcaaatcagaatgttgcggtgaatacgttcccgggccttgtacacaccg
cccgtcacaccatgggagtgggttgtaccagaagtagatagcttaaccttcggggggggcgtttaccacggtatgattcatgactggg
gtgaagtcgtaacaaggtaaccgtaggggaacctgcgg
```

(nucleotide sequence of 23 S rDNA of strain DD1)  SEQ ID NO: 2

```
agtaataacgaacgacacaggtataagaatacttgaggttgtatggttaagtgactaagcgtacaaggtggatgccttggcaatcaga
ggcgaagaaggacgtgctaatctgcgaaaagcttgggtgagttgataagaagcgtctaacccaagatatccgaatggggcaaccc
agtagatgaagaatctactatcaataaccgaatccataggttattgaggcaaaccgggagaactgaaacatctaagtaccccgagg
aaaagaaatcaaccgagattacgtcagtagcggcgagcgaaagcgtaagagccggcaagtgatagcatgaggattagaggaat
cggctgggaagccgggcggcacaggtgatagcccccgtacttgaaaatcattgtgtggtactgagcttgcgagaagtagggcggga
cacgagaaatcctgtttgaagaaggggggaccatcctccaaggctaaatactcctgattgaccgatagtgaaccagtactgtgaagg
aaaggcgaaaagaaccccggtgaggggagtgaaatagaacctgaaaccttgtacgtacaagcagtgggagcccgcgagggtga
ctgcgtaccttttgtataatgggtcagcgacttatattatgtagcgaggttaaccgaatagggagccgaagggaaaccgagtcttaact
gggcgtcgagttgcatgatatagacccgaaacccggtgatctagccatgggcaggttgaaggttgggtaacactaactggaggacc
gaaccgactaatgttgaaaaattagcggatgacctgtggctgggggtgaaaggccaatcaaaccgggagatagctggttctccccg
aaatctatttaggtagagccttatgtgaataccttcgggggtagagcactgtttcggctaggggccatcccggcttaccaacccgatgc
aaactgcgaataccgaagagtaatgcataggagacacacggcgggtgctaacgttcgtcgtggagagggaaacaacccagacc
gccagctaaggtcccaaagtttatattaagtggaaacgaagtgggaaggcttagacagctaggatgttggcttagaagcagccatc
atttaaagaaagcgtaatagctcactagtcgagtcggcctgcgcggaagatgtaacggggctcaaatatagcaccgaagctgcggc
atcaggcgtaagcctgttgggtaggggagcgtcgtgtaagcggaagaaggtggttcgagagggctgctggacgtatcacgagtgcg
aatgctgacataagtaacgataaaacgggtgaaaaacccgttcgccggaagaccaagggttcctgtccaacgttaatcggggcag
ggtgagtcggcccctaaggcgaggctgaagagcgtagtcgatgggaaacgggttaatattcccgtacttgttataattgcgatgtggg
gacggagtaggttaggttatcgacctgttggaaaaggtcgtttaagttggtaggtggagcgtttaggcaaatccggacgcttatcaaca
ccgagagatgatgacgaggcgctaaggtgccgaagtaaccgataccacacttccaggaaaagccactaagcgtcagattataata
aaccgtactataaaccgacacaggtggtcaggtagagaatactcaggcgcttgagagaactcgggtgaaggaactaggcaaaata
gcaccgtaacttcgggagaaggtgcgccggcgtagattgtagaggtatacccttgaaggttgaaccggtcgaagtgaccgctggct
gcaactgtttattaaaaacacagcactctgcaaacacgaaagtggacgtatagggtgtgatgcctgcccggtgctggaaggttaattg
atggcgttatcgcaagagaagcgcctgatcgaagccccagtaaacgcggccgtaactataacggtcctaaggtagcgaaattcctt
gtcgggtaagttccgacctgcacgaatggcataatgatggccaggctgtctccacccgagactcagtgaaattgaaatcgccgtgaa
gatgcggtgtacccgcggctagacggaaagacccccgtgaaccttactatagcttgacactgaaccttgaattttgatgtgtaggatag
gtgggaggctttgaagcggtaacgccagttatcgtggagccatccttgaaataccaccctttaacgtttgatgttctaacgaagtgcccg
gaacgggtactcggacagtgtctggtgggtagtttgactggggcggtctcctcccaaagagtaacggaggagcacgaaggtttgcta
atgacggtcggacatcgtcaggttagtgcaatggtataagcaagcttaactgcgagacgacaagtcgagcaggtgcgaaagcag
gtcatagtgatccggtggttctgaatggaagggccatcgctcaacggataaaaggtactccggggataacaggctgataccgccca
agagttcatatcgacggcggtgtttggcacctcgatgtcggctcatcacatcctggggctgaagtaggtcccaagggtatggctgttcgc
catttaaagtggtacgcgagctgggtttaaaacgtcgtgagacagtttggtccctatctgccgtgggcgttggagaattgagagggct
gctcctagtacgagaggaccggagtggacgcatcactggtgttccggttgtgtcgccagacgcattgccgggtagctacatgcgaa
gagataagtgctgaaagcatctaagcacgaaacttgcctcgagatgagttctcccagtatttaatactgtaagggttgttggagacgac
```

-continued gacgtagataggccgggtgtgtaagcgttgcgagacgttgagctaaccggtactaattgcccgagaggcttagccatacaacgctca agtgtttttggtagtgaaagttattacggaataagtaagtagtcagggaatcggct (nucleotide sequence of wcaJ-gene from strain DD1)

SEQ ID NO: 3 atgataaaacgccttttcgatattgttgtcgcattgatagcattgattttgttttcgcccttatatttgtttgtggcttataaggtaaaacaaatttt gggatcaccggtgttatttaaacaaacccgccccggattgcatggtaaacccttttgagatgattaagttcagaacaatgaaagacggc gcagatgaaaacggtaatattttgccggatgcggagcgcttaacacctttcggcaaaatgttgcgcgctaccagtctggacgagttgcc ggaactttggaatgtattaaaaggtgatatgagtctggtggggccgcgtcctctactgatggaatatttgccgctgtataacgaaagaca ggctaagcgccatgaagtgaaacccggaattaccggttatgcacaggtaaacggtcgcaatgccatcagttgggagcagaaatttg aattggatgcctggtatgttgaacatcaatccttgtggctggatttgaaaattatcgcaaagaccatccaaaaagtgatcgcaaaagac gatattaatgcggcagatgatgccaccatgcctaaatttgaaggaataaaaaatcatga (amino acid sequence of the enzyme encoded by the above wcaJ-gene)

SEQ ID NO: 4

MIKRLFDIVVALIALILFSPLYLFVAYKVKQNLGSPVLFKQTRPGLHGKPFEMIKFRTMKDGADEN

GNILPDAERLTPFGKMLRATSLDELPELWNVLKGDMSLVGPRPLLMEYLPLYNERQAKRHEVK

PGITGYAQVNGRNAISWEQKFELDAWYVEHQSLWLDLKIIAKTIQKVIAKDDINAADDATMPKFE

GNKKS (complete nucleotide sequence of plasmid pSacB)

SEQ ID NO: 5 tcgagaggcctgacgtcgggcccggtaccacgcgtcatatgactagttcggacctagggatatcgtcgacatcgatgctcttctgcgtt aattaacaattgggatcctctagactccataggccgctttcctggctttgcttccagatgtatgctctcctccggagagtaccgtgactttatt ttcggcacaaatacaggggtcgatggataaatacggcgatagtttcctgacggatgatccgtatgtaccggcggaagacaagctgca aacctgtcagatggagattgatttaatggcggatgtgctgagagcaccgccccgtgaatccgcagaactgatccgctatgtgtttgcgg atgattggccggaataaataaagccgggcttaatacagattaagcccgtataggtattattactgaataccaaacagcttacggagg acggaatgttacccattgagacaaccagactgccttctgattattaatatttttcactattaatcagaaggaataaccatgaattttacccg gattgacctgaatacctggaatcgcagggaacactttgccctttatcgtcagcagattaaatgcggattcagcctgaccaccaaactcg atattaccgctttgcgtaccgcactggcggagacaggttataagttttatccgctgatgatttacctgatctcccgggctgttaatcagtttcc ggagttccggatggcactgaaagacaatgaacttattactgggaccagtcagacccggtctttactgtctttcataaagaaaccgaaa cattctctgcactgtcctgccgttattttccggatctcagtgagtttatggcaggttataatgcggtaacggcagaatatcagcatgatacca gattgtttccgcagggaaatttaccggagaatcacctgaatatatcatcattaccgtgggtgagttttgacgggatttaacctgaacatca ccggaaatgatgattattttgccccggttttacgatggcaaagtttcagcaggaaggtgaccgcgtattattacctgttttctgtacaggttc atcatgcagtctgtgatggctttcatgcagcacggtttattaatacacttcagctgatgtgtgataacatactgaataaattaattaattctg tatttaagccaccgtatccggcaggaatggtggctttttttttatattttaaccgtaatctgtaatttcgtttcagactggttcaggatgagctcg cttggactcctgttgatagatccagtaatgacctcagaactccatctggatttgttcagaacgctcggttgccgccgggcgttttttattggtg agaatccaagcactagcggcgcgccggccggcccggtgtgaaataccgcacagatgcgtaaggagaaaataccgcatcaggcg ctcttccgcttcctcgctcactgactcgctgcgctcggtcgttcggctgcggcgagcggtatcagctcactcaaaggcggtaatacggtt atccacagaatcaggggataacgcaggaaagaacatgtgagcaaaaggccagcaaaaggccaggaaccgtaaaaaggccgc gttgctggcgtttttccataggctccgcccccctgacgagcatcacaaaaatcgacgctcaagtcagaggtggcgaaacccgacagg actataaagataccaggcgtttccccctggaagctccctcgtgcgctctcctgttccgaccctgccgcttaccggatacctgtccgcctttc tcccttcgggaagcgtggcgctttctcatagctcacgctgtaggtatctcagttcggtgtaggtcgttcgctccaagctgggctgtgtgcac gaaccccccgttcagcccgaccgctgcgccttatccggtaactatcgtcttgagtccaacccggtaagacacgacttatcgccactgg cagcagccactggtaacaggattagcagagcgaggtatgtaggcggtgctacagagttcttgaagtggtggcctaactacggctaca ctagaaggacagtatttggtatctgcgctctgctgaagccagttaccttcggaaaaagagttggtagctcttgatccggcaaacaaacc -continued

```
accgctggtagcggtggttttttttgtttgcaagcagcagattacgcgcagaaaaaaaggatctcaagaagatcctttgatcttttctacgg
ggtctgacgctcagtggaacgaaaactcacgttaagggattttggtcatgagattatcaaaaaggatcttcacctagatccttttaaagg
ccggccgcggccgccatcggcattttcttttgcgtttttatttgttaactgttaattgtccttgttcaaggatgctgtctttgacaacagatgttttct
tgcctttgatgttcagcaggaagctcggcgcaaacgttgattgtttgtctgcgtagaatcctctgtttgtcatatagcttgtaatcacgacatt
gtttcctttcgcttgaggtacagcgaagtgtgagtaagtaaaggttacatcgttaggatcaagatccatttttaacacaaggccagttttgtt
cagcggcttgtatgggccagttaaagaattagaaacataaccaagcatgtaaatatcgttagacgtaatgccgtcaatcgtcattttgat
ccgcgggagtcagtgaacaggtaccatttgccgttcatttaaagacgttcgcgcgttcaatttcatctgttactgtgttagatgcaatcagc
ggtttcatcactttttttcagtgtgtaatcatcgtttagctcaatcataccgagagcgccgtttgctaactcagccgtgcgttttttatcgctttgca
gaagttttgactttcttgacggaagaatgatgtgcttttgccatagtatgctttgttaaataaagattcttcgccttggtagccatcttcagttcc
agtgtttgcttcaaatactaagtatttgtggcctttatcttctacgtagtgaggatctctcagcgtatggttgtcgcctgagctgtagttgccttc
atcgatgaactgctgtacattttgatacgttttccgtcaccgtcaaagattgatttataatcctctacaccgttgatgttcaaagagctgtctg
atgctgatacgttaacttgtgcagttgtcagtgtttgtttgccgtaatgtttaccggagaaatcagtgtagaataaacggattttttccgtcaga
tgtaaatgtggctgaacctgaccattcttgtgtttggtcttttaggatagaatcatttgcatcgaatttgtcgctgtctttaaagacgcggccag
cgttttccagctgtcaatagaagtttcgccgacttttgatagaacatgtaaatcgatgtgtcatccgcatttttaggatctccggctaatgc
aaagacgatgtggtagccgtgatagtttgcgacagtgccgtcagcgttttgtaatggccagctgtcccaaacgtccaggccttttgcaga
agagatattttaattgtggacgaatcaaattcagaaacttgatatttttcattttttttgctgttcagggatttgcagcatatcatggcgtgtaata
tgggaaatgccgtatgtttccttatatggcttttggttcgtttcttcgcaaacgcttgagttgcgcctcctgccagcagtgcggtagtaaagg
ttaatactgttgcttgttttgcaaacttttttgatgttcatcgttcatgtctccttttttatgtactgtgttagcggtctgcttcttccagccctcctgtttga
agatggcaagttagttacgcacaataaaaaaagacctaaaatatgtaaggggtgacgccaaagtatacactttgcccttacacatttt
aggtcttgcctgctttatcagtaacaaacccgcgcgatttacttttcgacctcattctattagactctcgtttggattgcaactggtctatttttcct
cttttgtttgatagaaaatcataaaaggatttgcagactacgggcctaaagaactaaaaaatctatctgtttcttttcattctctgtatttttata
gtttctgttgcatgggcataaagttgccttttaatcacaattcagaaaatatcataatatctcatttcactaaataatagtgaacggcaggt
atatgtgatgggttaaaaaggatcggcggccgctcgatttaaatc
```

(complete nucleotide sequence of plasmid pSacB_delta_ldhA)

SEQ ID NO: 6

```
tcgagaggcctgacgtcgggcccggtaccacgcgtcatatgactagttcggacctagggatgggtcagcctgaacgaaccgcactt
gtatgtaggtagttttgaccgcccgaatattcgttataccttggtggaaaaattcaaaccgatggagcaattatacaattttgtggcggcgc
aaaaaggtaaaagcggtatcgtctattgcaacagccgtagcaaagtggagcgcattgcggaagcccctgaagaaaagaggcatttc
cgcagccgcttatcatgcgggcatggagccgtcgcagcgggaagcggtgcaacaggcgtttcaacgggataatattcaagtggtgg
tggcgaccattgcttttggtatggggatcaacaaatctaatgtgcgttttgtggcgcatttttgatttatctcgcagcattgaggcgtattatcag
gaaaccgggcgcgcggggcgggacgacctgccggcggaagcggtactgttttacgagccggcggattatgcctggttgcataaaat
tttattggaagagccggaaagcccgcaacgggatattaaacggcataagctggaagccatcggcgaatttgccgaaagccagacc
tgccgtcgtttagtgctgttaaattatttcggcgaaaaccgccaaacgccatgtaataactgtgatatctgcctcgatccgccgaaaaaat
atgacggattattagacgcgcagaaaatcctttcgaccatttatcgcaccgggcaacgtttcggcacgcaatacgtaatcggcgtaatg
cgcggtttgcagaatcagaaaataaaagaaaatcaacatgatgagttgaaagtctacggaattggcaaagataaaagcaaagaat
actggcaatcggtaattcgtcagctgattcatttgggctttgtgcaacaaatcatcagcgatttcggcatggggaccagattacagctcac
cgaaagcgcgcgtcccgtgctgcgcggcgaagtgtctttggaactggccatgccgagattatcttccattaccatggtacaggctccgc
aacgcaatgcggtaaccaactacgacaaagatttatttgcccgcctgcgtttcctgcgcaaacagattgccgacaaagaaacattc
cgccttatattgtgttcagtgacgcgaccttgcaggaaatgtcgttgtatcagccgaccagcaaagtggaaatgctgcaaatcaacggt
gtcggcgccatcaaatggcagcgcttcggacagccttttatggcgattattaaagaacatcaggctttgcgtaaagcgggtaagaatc
cgttggaattgcaatcttaaaattttttaacttttttgaccgcacttttaaggttagcaaattccaataaaaagtgcggtgggttttcgggaattttt
aacgcgctgatttcctcgtcttttcaatttyttcgyctccatttgttcggyggttgccgatccttttcttgactgagatccataagagagtagaa
```

-continued

```
tagcgccgcttatatttttaatagcgtacctaatcgggtacgcttttttatgcggaaaatccatatttttctaccgcacttttctttaaagatttat acttaagtctgtttgattcaatttatttggaggttttatgcaacacattcaactggctcccgatttaacattcagtcgcttaattcaaggattctg gcggttaaaaagctggcggaaatcgccgcaggaattgcttacattcgttaagcaaggattagaattaggcgttgatacgctggatcat gccgcttgttacggggcttttacttccgaggcggaattcggacgggcgctggcgctggataaatccttgcgcgcacagcttactttggtg accaaatgcgggattttgtatcctaatgaagaattacccgatataaaatcccatcactatgacaacagctaccgccatattatgtggtcg gcgcaacgttccattgaaaaactgcaatgcgactattagatgtattgctgattcaccgwctttctccctgtgcggatcccgaacaaatcg cgcgggcttttgatgaactttatcaaaccggraaagtacgttatttcggggtatctaactatacgccggctaagttcgccatgttgcaatctt atgtgaatcagccgttaatcactaatcaaattgagatttcgcctcttcatcgtcaggcttttgatgacggtaccctggattttttactggaaaa acgtattcaaccgatggcatggtcgccacttgccggcggtcgtttattcaatcaggatgagaacagtcgggcggtgcaaaaaacatta ctcgaaatcggtgaaacgaaaggagaaacccgtttagatacattggcttatgcctggttattggcgcatccggcaaaaattatgccggt tatggggtccggtaaaattgaacgggtaaaaagcgcggcggatgcgttacgaatttccttcactgaggaagaatggattaaggtttatg ttgccgcacagggacgggatattccgtaacatcatccgtctaatcctgcgtatctggggaaagatgcgtcatcgtaagaggtctataat attcgtcgttttgataagggtgccatatccggcacccgttaaaatcacattgcgttcgcaacaaaattattccttacgaatagcattcacct cttttaacagatgttgaatatccgtatcggcaaaaatatcctctatatttgcggttaaacgcgccgccagttagcatattgagtgctggttc ccggaatattgacgggttcggtcataccgagccagtcttcaggttggaatccccatcgtcgacatcgatgctcttctgcgttaattaacaa ttgggatcctctagactccataggccgctttcctggctttgcttccagatgtatgctctcctccggagagtaccgtgactttattttcggcaca aatacaggggtcgatggataaatacggcgatagtttcctgacggatgatccgtatgtaccggcggaagacaagctgcaaacctgtca gatggagattgatttaatggcggatgtgctgagagcaccgccccgtgaatccgcagaactgatccgctatgtgtttgcggatgattggc cggaataaataaagccgggcttaatacagattaagcccgtatagggtattattactgaataccaaacagcttacggaggacggaatg ttacccattgagacaaccagactgccttctgattattaatatttttcactattaatcagaaggaataaccatgaattttacccggattgacct gaatacctggaatcgcagggaacactttgccctttatcgtcagcagattaaatgcggattcagcctgaccaccaaactcgatattaccg ctttgcgtaccgcactggcggagacaggttataagtttatccgctgatgatttacctgatctcccgggctgttaatcagtttccggagttcc ggatggcactgaaagacaatgaacttatttactgggaccagtcagacccggtctttactgtctttcataaagaaaccgaaacattctctg cactgtcctgccgttattttccggatctcagtgagtttatggcaggttataatgcggtaacggcagaatatcagcatgataccagattgtttc cgcagggaaatttaccggagaatcacctgaatatatcatcattaccgtgggtgagttttgacgggatttaacctgaacatcaccggaaa tgatgattattttgccccggttttacgatggcaaagtttcagcaggaaggtgaccgcgtattattacctgtttctgtacaggttcatcatgca gtctgtgatggctttcatgcagcacgttattaatacacttcagctgatgtgtgataacatactgaaataaattaattaattctgtatttaagc caccgtatccggcaggaatggtggcttttttttttatattttaaccgtaatctgtaatttcgtttcagactggttcaggatgagctcgcttggactc ctgttgatagatccagtaatgacctcagaactccatctggatttgttcagaacgctcggttgccgccgggcgttttttattggtgagaatcca agcactagcggcgcgccggccggcccggtgtgaaataccgcacagatgcgtaaggagaaaataccgcatcaggcgctcttccgct tcctcgctcactgactcgctgcgctcggtcgttcggctgcggcgagcggtatcagctcactcaaaggcggtaatacggttatccacaga atcagggataacgcaggaaagaacatgtgagcaaaaggccagcaaaaggccaggaaccgtaaaaaggccgcgttgctggcg tttttccataggctccgcccccctgacgagcatcacaaaaatcgacgctcaagtcagaggtggcgaaacccgacaggactataaag ataccaggcgtttccccctggaagctccctcgtgcgctctcctgttccgaccctgccgcttaccggatacctgtccgcctttctcccttcgg gaagcgtggcgctttctcatagctcacgctgtaggtatctcagttcggtgtaggtcgttcgctccaagctgggctgtgtgcacgaaccccc cgttcagcccgaccgctgcgccttatccggtaactatcgtcttgagtccaacccggtaagacacgacttatcgccactggcagcagcc actggtaacaggattagcagagcgaggtatgtaggcggtgctacagagttcttgaagtggtggcctaactacggctacactagaagg acagtatttggtatctgcgctctgctgaagccagttaccttcggaaaaagagttggtagctcttgatccggcaaacaaaccaccgctggt agcggtggtttttttgtttgcaagcagcagattacgcgcagaaaaaaaggatctcaagaagatcctttgatcttttctacggggtctgacg ctcagtggaacgaaaactcacgttaagggattttggtcatgagattatcaaaaaggatcttcacctagatccttttaaaggccggccgc
```

-continued

```
ggccgccatcggcattttcttttgcgttttttatttgttaactgttaattgtccttgttcaaggatgctgtctttgacaacagatgttttcttgcctttgat gttcagcaggaagctcggcgcaaacgttgattgtttgtctgcgtagaatcctctgtttgtcatatagcttgtaatcacgacattgtttcctttcg cttgaggtacagcgaagtgtgagtaagtaaaggttacatcgttaggatcaagatccattttttaacacaaggccagttttgttcagcggctt gtatgggccagttaaagaattagaaacataaccaagcatgtaaatatcgttagacgtaatgccgtcaatcgtcattttttgatccgcggga gtcagtgaacaggtaccatttgccgttcatttttaaagacgttcgcgcgttcaatttcatctgttactgtgttagatgcaatcagcggtttcatc acttttttcagtgtgtaatcatcgtttagctcaatcataccgagagcgccgtttgctaactcagccgtgcgttttttatcgctttgcagaagttttt gactttcttgacggaagaatgatgtgcttttgccatagtatgctttgttaaataaagattcttcgccttggtagccatcttcagttccagtgtttg cttcaaatactaagtatttgtggccttttatcttctacgtagtgaggatctctcagcgtatggttgtcgcctgagctgtagttgccttcatcgatg aactgctgtacattttgatacgttttccgtcaccgtcaaagattgattttataatcctctacaccgttgatgttcaaagagctgtctgatgctga tacgttaacttgtgcagttgtcagtgtttgtttgccgtaatgtttaccggagaaatcagtgtagaataaacggattttttccgtcagatgtaaat gtggctgaacctgaccattcttgtgtttggtcttttaggatagaatcatttgcatcgaatttgtcgctgtctttaaagacgcggccagcgttttc cagctgtcaatagaagtttcgccgacttttttgatagaacatgtaaatcgatgtgtcatccgcattttaggatctccggctaatgcaaagac gatgtggtagccgtgatagtttgcgacagtgccgtcagcgttttgtaatggccagctgtcccaaacgtccaggccttttgcagaagagat atttttaattgtggacgaatcaaattcagaaacttgatatttttcatttttttgctgttcagggatttgcagcatatcatggcgtgtaatatgggaa atgccgtatgtttccttatatggcttttggttcgtttctttcgcaaacgcttgagttgcgcctcctgccagcagtgcggtagtaaaggttaatact gttgcttgttttgcaaacttttttgatgttcatcgttcatgtctccttttttatgtactgtgttagcggtctgcttcttccagccctcctgtttgaagatgg caagttagttacgcacaataaaaaaagacctaaaatatgtaaggggtgacgccaaagtatacactttgccctttacacattttaggtctt gcctgctttatcagtaacaaaccgcgcgatttacttttcgacctcattctattagactctcgtttggattgcaactggtctatttttcctcttttgttt gatagaaaatcataaaaggatttgcagactacgggcctaaagaactaaaaaatctatctgtttcttttcattctctgtatttttttatagtttctgt tgcatgggcataaagttgccttttttaatcacaattcagaaaatatcataatatctcatttcactaaataatagtgaacggcaggtatatgtg atgggttaaaaaggatcggcggccgctcgatttaaatc (complete nucleotide sequence of plasmid pSacB_delta_pflA)
                                                                                                            SEQ ID NO: 7
tcgagtcaatgcgggatttgacttatgatgtggcaaacaaccgatttccgattattactacacgtaaaagttattggaaagcggcgattgcg gagtttctgggttatatccgcggctacgataatgcggcggatttccgtaaattaggagcaaaaacctgggatgccaacgctaatgaaa atcaggtatggctgaataaccctcatcgcaaaggcaccgacgacatggggcgcgtttacggcgtacagggcagagcctggcgtaa gcctaacggcgaaaccgttgatcaattacgcaaaattgtcaacaatttaagtcgcggcattgatgatcgcggcgaaattctgacctttt aaacccgggcgaattcgatctcggttgtctgcgcccttgtatgtacaatcacacgttttctttgctgggcgatacgctttatttaaccagttat caacgctcctgtgacgtaccttaggcttgaatttcaatcaaattcaagtatttacattcttagctttaatggcgcagattaccggtaaaaaa gccggtcaggcatatcacaaaatcgtcaatgcgcatatttacgaagaccagctggaactaatgcgcgacgtgcagttaaaacgcga accgttcccgtcgccaaaactggaaattaatccggacattaaaacccttgaagatttagaaacctgggtaaccatggatgatttcaacg tcgttggttaccaatgccacgaaccgataaaatatccgttctcggtataaaccgacaaagtgcggtcaaaaatttaatattttcatctgtt atagaaaatatttttcaacataaaatctagggatgcctgtttggcgtccgtaaatacgcagaaaaatattaaatttttgaccgcacttttttc atctcaattaacagcctgataattcttatggatcaacaaattagctttgacgaaaaaatgatgaatcgagctcttttccttgccgacaagg cggaagctttaggggaaattcccgtaggtgccgtattggtggatgaacggggcaatatcattggtgaaggctggaacctctctattgtg aactcggatcccaccgccatgccgaaattattgcgttgcgtaacgccgcgcagaaaatccaaaattaccgcctgctcaataccactt tatacgtgacttagaaccctgcaccatgtgcgccggcgcgattttacacagccgaatcaaacgcttggtattcggggcgtccgattac aaaaccggtgcggtgggttccagatttcatttttttgaggattataaaatgaatcatggggttgagatcacaagcggtgtcttacaggatc aatgcagtcagaagttaagccgcttttttccaaaagcgcagggaacagaaaaaacaacaaaaagctaccgcacttttacaacaccc ccggcttaactcctctgaaaaatagtgacaaaaaaaccgtcataatgtttacgacggttttttttatttcttaatatgcccttaaataatcaac aaaatatagcaagaagattatagcaaagaatttcgttttttttcagagaatagtcaaatcttcgcaaaaaactaccgcacttttatccgctttt aatcaggggaattaaaacaaaaaaattccgcctattgaggcggaatttattaagcaataagacaaactctcaattacattgattgtgta
```

-continued

```
aacgtacgagtgatgacgtcttgttgttgctctttagttaatgagttgaaacgaaccgcgtaacctgaaacacgaatggttaattgcgggt
attttccggattttccatcgcgtctaacaacatttcacggttaagaacgttaacattcaagtgttgaccgccttccactgtcgcttcatgatg
gaaataaccgtccattaaaccggcaaggttgcgttttgcgcttcgtcatctttacctaatgcgttcggtacgatagagaaggtatatgaa
ataccgtctttcgcgtaagcgaacggaagtttagccacagaagtaagtgaagcaaccgcaccttttggtcacgaccgtgcattgggttt
gcacccggtccgaatggcgcgcctgctcgacgaccgtccggagtattaccggttttcttaccgtataccacgttagaagtgatagtcag
gatagattgtgtcggagttgcgttgcggtaagttttgtgttttgaactttttcatgaaacgttcaactaagtctaccgctaaatcatcaacac
gcggatcattgttaccgaattgcggatattcgccttcaatttcgaagtcgatagcaacattcgaggccacgacattaccgtctttatctttga
tgtcgccgcgaatcggtttaactttcgcatatttgattgcggataatgagtccgcagccacggaaagacccgcgataccgcaagccatt
gtacggaatacgtcgcgatcgtggaacgccatcaatgccgcttcatatgcatatttatcgtgcatgaagtggatgatgttcaatgcggtta
catattgagtcgccaaccagtccatgaaactgtccatacgttcgattacggtatcgaaattcaatacttcgtctgtaatcggcgcagtttta
ggaccgacttgcataccattttctcatcgataccgccgttaattgcgtataacatagttttagctaagtttgcgcgcgcaccgaagaattg
catttgtttacctacgaccatcggtgatacgcagcatgcgattgcatagtcatcgttgttgaagtcaggacgcattaagtcatcattttcgta
ttgtacggaggaagtatcaatagatactttcgcacagaaacgtttgaacgcttcaggtaattgttcggaccaaagaatagttaagtttggt
tccggagaagtacccatagtgtataaagtatgtaatacgcggaagctgttttagttaccaacggacgaccgtctaagcccataccggc
gatagtttcggttgccctctagactccataggccgctttcctggctttgcttccagatgtatgctctcctccggagagtaccgtgactttattttc
ggcacaaatacaggggtcgatggataaatacggcgatagtttcctgacggatgatccgtatgtaccggcggaagacaagctgcaaa
cctgtcagatggagattgatttaatggcggatgtgctgagagcaccgccccgtgaatccgcagaactgatccgctatgtgtttgcggat
gattggccggaataaataaagccgggcttaatacagattaagcccgtataggtattattactgaataccaaacagcttacggaggac
ggaatgttacccattgagacaaccagactgccttctgattattaatatttttcactattaatcagaaggaataaccatgaattttacccggat
tgacctgaatacctggaatcgcagggaacactttgccctttatcgtcagcagattaaatgcggattcagcctgaccaccaaactcgata
ttaccgctttgcgtaccgcactggcggagacaggttataagttttatccgctgatgatttacctgatctcccgggctgttaatcagtttccgg
agttccggatggcactgaaagacaatgaacttatttactgggaccagtcagacccggtctttactgtctttcataaagaaaccgaaaca
ttctctgcactgtcctgccgttattttccggatctcagtgagtttatggcaggttataatgcggtaacggcagaatatcagcatgataccag
attgtttccgcagggaaatttaccggagaatcacctgaatatatcatcattaccgtgggtgagttttgacgggatttaacctgaacatcac
cggaaatgatgattattttgccccggttttacgatggcaaagtttcagcaggaaggtgaccgcgtattattacctgtttctgtacaggttcat
catgcagtctgtgatggctttcatgcagcacggtttattaatacacttcagctgatgtgtgataacatactgaaataaattaattaattctgta
tttaagccaccgtatccggcaggaatggtggcttttttttatattttaaccgtaatctgtaatttcgtttcagactggttcaggatgagctcgctt
ggactcctgttgatagatccagtaatgacctcagaactccatctggatttgttcagaacgctcggttgccgccgggcgttttttattggtgag
aatccaagcactagcggcgcgccgccggcccggtgtgaaataccgcacagatgcgtaaggagaaaataccgcatcaggcgctc
ttccgcttcctcgctcactgactcgctgcgctcggtcgttcggctgcggcgagcggtatcagctcactcaaaggcggtaatacggttatc
cacagaatcaggggataacgcaggaaagaacatgtgagcaaaaggccagcaaaaggccaggaaccgtaaaaaggccgcgtt
gctggcgtttttccataggctccgcccccctgacgagcatcacaaaaatcgacgctcaagtcagaggtggcgaaacccgacaggac
tataaagataccaggcgtttccccctggaagctccctcgtgcgctctcctgttccgaccctgccgcttaccggatacctgtccgcctttctc
ccttcgggaagcgtggcgctttctcatagctcacgctgtaggtatctcagttcggtgtaggtcgttcgctccaagctgggctgtgtgcacg
aaccccccgttcagcccgaccgctgcgccttatccggtaactatcgtcttgagtccaacccggtaagacacgacttatcgccactggc
agcagccactggtaacaggattagcagagcgaggtatgtaggcggtgctacagagttcttgaagtggtggcctaactacggctacac
tagaaggacagtatttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttgatcttttctacggg
gtctgacgctcagtggaacgaaaactcacgttaagggattttggtcatgagattatcaaaaaggatcttcacctagatccttttaaaggc
cggccgcggccgccatcggcattttctttttgcgttttttatttgttaactgttaattgtccttgttcaaggatgctgtctttgacaacagatgttttctt
```

-continued gcctttgatgttcagcaggaagctcggcgcaaacgttgattgtttgtctgcgtagaatcctctgtttgtcatatagcttgtaatcacgacattg tttcctttcgcttgaggtacagcgaagtgtgagtaagtaaaggttacatcgttaggatcaagatccattttaacacaaggccagttttgttc agcggcttgtatgggccagttaaagaattagaaacataaccaagcatgtaaatatcgttagacgtaatgccgtcaatcgtcattttgatc cgcgggagtcagtgaacaggtaccatttgccgttcattttaaagacgttcgcgcgttcaatttcatctgttactgtgttagatgcaatcagc ggtttcatcactttttttcagtgtgtaatcatcgtttagctcaatcataccgagagcgccgtttgctaactcagccgtgcgttttttatcgctttgca gaagttttttgacttcttgacggaagaatgatgtgcttttgccatagtatgctttgttaaataaagattcttcgccttggtagccatcttcagttcc agtgtttgcttcaaatactaagtatttgtggcctttatcttctacgtagtgaggatctctcagcgtatggttgtcgcctgagctgtagttgccttc atcgatgaactgctgtacattttgatacgttttccgtcaccgtcaaagattgatttataatcctctacaccgttgatgttcaaagagctgtctg atgctgatacgttaacttgtgcagttgtcagtgtttgtttgccgtaatgtttaccggagaaatcagtgtagaataaacggattttttccgtcaga tgtaaatgtggctgaacctgaccattcttgtgtttggtcttttaggataagaatcatttgcatcgaatttgtcgctgtctttaaagacgcggccag cgttttttccagctgtcaatagaagtttcgccgacttttttgatagaacatgtaaatcgatgtgtcatccgcattttaggatctccggctaatgc aaagacgatgtggtagccgtgatagtttgcgacagtgccgtcagcgttttgtaatggccagctgtcccaaacgtccaggcctttttgcaga agagatatttttaattgtggacgaatcaaattcagaaacttgatattttttcattttttttgctgttcagggatttgcagcatatcatggcgtgtaata tgggaaatgccgtatgttccttatatggcttttggttcgtttctttcgcaaacgcttgagttgcgcctcctgccagcagtgcggtagtaaagg ttaatactgttgcttgttttgcaaacttttttgatgttcatcgttcatgtctcctttttatgtactgtgttagcggtctgcttcttccagccctcctgtttga agatggcaagttagttacgcacaataaaaaaagacctaaaatatgtaaggggtgacgccaaagtatacactttgcccctttacacattttt aggtcttgcctgctttatcagtaacaaacccgcgcgatttactttttcgacctcattctattagactctcgtttggattgcaactggtctattttcct cttttgtttgatagaaaatcataaaaggatttgcagactacgggcctaaagaactaaaaaatctatctgtttcttttcattctctgtattttttata gtttctgttgcatgggcataaagttgcctttttaatcacaattcagaaaatatcataatatctcatttcactaaataatagtgaacggcaggt atatgtgatgggttaaaaaggatcggcggccgctcgatttaaatc (complete nucleotide sequence of plasmid pSacB_wcaJ)

SEQ ID NO: 8 tcgagtaagccgattcagctgatccgccacatggggaaaaagcctaatctgcggaatatgaaaccgataccagtccagtaaagttg acaaatcgacatcatattgctcaaccaagtattgaaaagcgttttcaccgcgatgatacaattcgaccagccggttaaataacgtttcac tccgttccggtgccaaacgagacgcaatatgcttataggcggaatacagaaaatcgatttccgcataaagcgtatcgtccaaatctaa aaccaacgctttatttttcataatgatgagccagtacttccgcgtcataccgcaacattaataaatccgcttcccagtcttcgaacgcagg aatcggctgattaaacaaatattcctgaatcaaccaacggggataattggctcccgccagataactcaacggataaccgccgccga acctagggttaaatttcaataccaagaatttcagcggtggattccttataaaatacttggattgttaagcaaccgcgcgcccccggtaaac gggacaattttttccgataattgcgtcacgatggcattttttctggtcacacctttgttaatttcccccgctctgacaaaaattctctttctcggta ccgcacttttcagttcggaattttttatcaaaataacaatccacggtatattcgtcgtattccgccggcgaaatatattgcataaacattaattc gggattttccaattgctccggtgaaatatcttccggtttctccgccacaaaaattccttacttaaactaccgttgtaaggcttcacaaaaac aggatattcaaattgaccttttcaaactgcttcggtaccgcaatattatgttcaataaacagttgattggttaatcgtttgtcgcgacatttttct gacaaactctgtatcactaacggaaataaaaataccttttttctttaaaccgttgcagatgttcgcttaaaataagcaattccgtatcaatag tcggaataatcaatttcacgttattttcttcacagattttaagtaaggtcggaatatactccgcatcagtgaccgggggtacaggaaaatgt ccgtcggccacataacaagccggcgccaactcgggatttaaatctacggttaacacttttccgtcacttactaactgcgataattcctatt aaacgcctgaacgagagaaacacgttgtccggccgatgtaacaagaatattcatgattttttattcccttcaaatttaggcatggtggcat catctgccgcattaatatcgtcttttgcgatcacttttttggatggtctttgcgataattttcaaatccagccacaaggattgatgttcaacatac caggcatccaattcaaatttctgctcccaactgatggcattgcgaccgtttacctgtgcataaccggtaattccgggtttcacttcatggcg cttagcctgtctttcgttatacagcggcaaatattccatcacacaaacaaatataagggcgaaaacaaaatcaatgctatcaatgcgac aacaatatcgaaaaggcgttttatcatgaaaatctcctacgaccgaccaatttggggctgacaaaagtgccgttttttccaccagaaccgt ataaactaaaaccaggaaaagcggataccagactaacggcagtcttaatatggaagacggcacccaaacgatccaacaaaaatt aataaaaataaataaaataaatatacgttctttccacgccaacaattgggtattcatcacatagataattgaatttaataaaaaatatata

```
aatgccaaaaatgcaaaaatgccaaatgccaaataaagttctataaagaagctatgcggattagtgtaacccaaagggaaacttaa
ctttatttgatcgaaatactgaatgtagtcccgcggtccataacccaaccataaaattttaaaattatctaaaaatgtcgtataaatttccgt
ccggtaacctacggacttatcatcgcccatagaaaatattaccaatgaaaaacgttcaatcggacgctccagccaatcaattttggcg
agcagaataaacacttcctgtaaccaagaaagattaaatataaataatgcgatcacgcaggcgaaaaacagatataccgccttaaa
ataggtagatgcgtttaaaaacaagatcagcatcaacataatcaaatagctcagtaataccgaacgggaggcactgatcacaatag
ctaaccccataataaaaataagagcatagccgattaacttaattttccagttgttttctctgatgatgtaaaaaaatcccaccgccaccgc
aagagaaatcataattacggactggtcattggtattaaagaaaaaacctttaaacgccttatcagttacggttaattcttcattacccgaa
accaactggaacccaataaagcctcaataaaaaagcccgccagcacaattaatgatattcccaacaaaaggtgcctaatccctgc
ttctccatcaccccggttaaacgtcaaaaaagaataatgaaataaaaacatcacaattccgaagaaaaacaaatcaactaattttttct
gtagaaaacgcatttaataccgataaaaagccgaagaaaaacaacacgtacaccggaaactgtaatttaaaaaaatcagtttccat
atcccttaaaaaggggttattaccgctaagaaaaagaacaaaaaacacaacgcactatctaacctcggcactcctatttgtgtcgat
agtgcgggagaaagtatcaccagtcccaacgcaaagagtaatagcaacttaaaaatgctgataacattaatattcatatcaaataat
attttttgattaatttctcaatttctttataagaacgctcgcgcagaaacttctcttttgccagcgataaattcacttgcgacattttgtctaaaacc
gttctgtcttcggccaatttattcaacgtctcagccaactcccgataatctcccgccgtatattgaattccaccgcctttcgccagtagtttttc
cacttcaggatgtttctgacagcttacaatcggtaatgcgcaacagatataatcggatctagactccataggccgctttcctggctttgctt
ccagatgtatgctctcctccggagagtaccgtgactttattttcggcacaaatacagggtcgatggataaatacggcgatagtttcctg
acggatgatccgtatgtaccggcggaagacaagctgcaaacctgtcagatggagattgatttaatggcggatgtgctgagagcaccg
ccccgtgaatccgcagaactgatccgctatgtgtttgcggatgattggccgaataaataaagccgggcttaatacagattaagcccgt
atagggtattattactgaataccaaacagcttacggaggacggaatgttacccattgagacaaccagactgccttctgattattaatatttt
tcactattaatcagaaggaataaccatgaattttacccggattgacctgaatacctggaatcgcagggaacactttgccctttatcgtcag
cagattaaatgcggattcagcctgaccaccaaactcgatattaccgctttgcgtaccgcactggcggagacaggttataagttttatccg
ctgatgatttacctgatctcccgggctgttaatcagtttccggagttccggatggcactgaaagacaatgaacttatttactgggaccagtc
agacccggtctttactgtctttcataaagaaaccgaaacattctctgcactgtcctgccgttattttccggatctcagtgagtttatggcaggt
tataatgcggtaacggcagaatatcagcatgataccagattgtttccgcagggaaatttaccggagaatcacctgaatatatcatcatta
ccgtgggtgagttttgacgggatttaacctgaacatcaccggaaatgatgattatttttgccccggttttacgatggcaaagtttcagcagg
aaggtgaccgcgtattattacctgtttctgtacaggttcatcatgcagtctgtgatggctttcatgcagcacggtttattaatacacttcagct
gatgtgtgataacatactgaaataaattaattaattctgtatttaagccaccgtatccggcaggaatggtggcttttttttttatattttaaccgta
atctgtaatttcgtttcagactggttcaggatgagctcgcttggactcctgttgatagatccagtaatgacctcagaactccatctggatttgt
tcagaacgctcggttgccgccgggcgttttttattggtgagaatccaagcactagcggcgcgccggccgcccggtgtgaaataccgc
acagatgcgtaaggagaaaataccgcatcaggcgctcttccgcttcctcgctcactgactcgctgcgctcggtcgttcggctgcggcg
agcggtatcagctcactcaaaggcggtaatacggttatccacagaatcaggggataacgcaggaaagaacatgtgagcaaaagg
ccagcaaaaggccaggaaccgtaaaaaggccgcgttgctggcgtttttccataggctccgcccccctgacgagcatcacaaaaatc
gacgctcaagtcagaggtggcgaaacccgacaggactataaagataccaggcgtttccccctggaagctccctcgtgcgctctcctg
ttccgaccctgccgcttaccggatacctgtccgcctttctcccttcgggaagcgtggcgctttctcatagctcacgctgtaggtatctcagtt
cggtgtaggtcgttcgctccaagctgggctgtgtgcacgaaccccccgttcagcccgaccgctgcgccttatccggtaactatcgtcttg
agtccaacccggtaagacacgacttatcgccactggcagcagccactggtaacaggattagcagagcgaggtatgtaggcggtgct
acagagttcttgaagtggtggcctaactacggctacactagaaggacagtatttggtatctgcgctctgctgaagccagttaccttcgga
aaaagagttggtagctcttgatccggcaaacaaaccaccgctggtagcggtggtttttttgtttgcaagcagcagattacgcgcagaaa
aaaaggatctcaagaagatcctttgatcttttctacggggtctgacgctcagtggaacgaaaactcacgttaagggattttggtcatgag
attatcaaaaaggatcttcacctagatccttttaaaggccggccgcggccgccatcggcattttcttttgcgttttttatttgttaactgttaattgt
```

-continued ccttgttcaaggatgctgtctttgacaacagatgttttcttgcctttgatgttcagcaggaagctcggcgcaaacgttgattgtttgtctgcgta
gaatcctctgtttgtcatatagcttgtaatcacgacattgtttcctttcgcttgaggtacagcgaagtgtgagtaagtaaaggttacatcgtta
ggatcaagatccattttttaacacaaggccagttttgttcagcggcttgtatgggccagttaaagaattagaaacataaccaagcatgtaa
atatcgttagacgtaatgccgtcaatcgtcattttttgatccgcgggagtcagtgaacaggtaccatttgccgttcattttaaagacgttcgc
gcgttcaatttcatctgttactgtgttagatgcaatcagcggtttcatcacttttttcagtgtgtaatcatcgtttagctcaatcataccgagagc
gccgtttgctaactcagccgtgcgttttttatcgctttgcagaagtttttgactttcttgacggaagaatgatgtgcttttgccatagtatgctttgt
taaataaagattcttcgccttggtagccatcttcagttccagtgtttgcttcaaatactaagtatttgtggccttatcttctacgtagtgaggat
ctctcagcgtatggttgtcgcctgagctgtagttgccttcatcgatgaactgctgtacattttgatacgttttccgtcaccgtcaaagattgatt
tataatcctctacaccgttgatgttcaaagagctgtctgatgctgatacgttaacttgtgcagttgtcagtgtttgtttgccgtaatgtttaccgg
agaaatcagtgtagaataaacggattttttccgtcagatgtaaatgtggctgaacctgaccattcttgtgtttggtatttaggatagaatcatt
tgcatcgaatttgtcgctgtctttaaagacgcggccagcgtttttccagctgtcaatagaagtttcgccgacttttttgatagaacatgtaaat
cgatgtgtcatccgcattttttaggatctccggctaatgcaaagacgatgtggtagccgtgatagtttgcgacagtgccgtcagcgttttgta
atggccagctgtcccaaacgtccaggccttttgcagaagagatattttttaattgtggacgaatcaaattcagaaacttgatatttttcatttttt
tgctgttcagggatttgcagcatatcatggcgtgtaatatgggaaatgccgtatgtttccttatatggcttttggttcgtttctttcgcaaacgctt
gagttgcgcctcctgccagcagtgcggtagtaaaggttaatactgttgcttgttttgcaaacttttttgatgttcatcgttcatgtctcctttttttatg
tactgtgttagcggtctgcttcttccagccctcctgtttgaagatggcaagttagttacgcacaataaaaaaagacctaaaatatgtaagg
ggtgacgccaaagtatacactttgcccttacacatttaggtcttgcctgctttatcagtaacaaaccgcgcgatttacttttcgacctcatt
ctattagactctcgtttggattgcaactggtctattttcctcttttgtttgatagaaaatcataaaaggatttgcagactacgggcctaaagaa
ctaaaaaatctatctgtttcttttcattctcgtatttttatagttctgttgcatgggcataaagttgcctttttaatcacaattcagaaaatatcat
aatatctcatttcactaaataatagtgaacggcaggtatatgtgatgggttaaaaaggatcggcggccgctcgatttaaatc (complete nucleotide sequence of plasmid pSacB_pflD)

SEQ ID NO: 9 tcgagaggcctgacgtcgggcccggtaccacgcgtcatatgactagttcggacctagggatgggatcgagctcttttccttgccgaca
aggcggaagctttaggggaaattcccgtaggtgccgtattggtggatgaacggggcaatatcattggtgaaggctggaacctctctatt
gtgaactcggatcccaccgccatgccgaaattattgcgttgcgtaacgccgcgcagaaaatccaaaattaccgcctgctcaatacc
actttatacgtgactttagaaccctgcaccatgtgcgccggcgcgattttacacagccgaatcaaacgcttggtattcggggcgtccgat
tacaaaaccggtgcggtgggttccagatttcatttttttgaggattataaaatgaatcatgggggttgagatcacaagcggtgtcttatagga
tcaatgcagtcagaagttaagccgcttttttccaaaagcgcagggaacagaaaaaacaacaaaaagctaccgcacttttacaacacc
cccggcttaactcctctgaaaaatagtgacaaaaaaaccgtcataatgtttacgacggttttttttatttcttctaatatgtcacattaagcccg
tagcctgcaagcaaccccttaacatgctccattaattcttttgtcggcggttttacatcttcaagctcgtatttatcgccgagtacttcccattta
tgggcgcctagacggtgataaggtaataattccacttttttcgatattcttcatatctttaatgaaattccccagcatgtgcaaatcttcgtcact
atctgtataacccggcactacaacatggcggatccaggtacgctgatttcgatccgctaaatattttgcgaattcgagcactcttttattcg
gcacgccaatcaggctttcgtgaacccgttcattcatttctttcaggtcaagcaacacaagatccgtgtcatcaatcaattcatcaataat
atgatcatgatgacggacgaaaccgttggtatccaagcaagtattaattccttctttatggcaggctctgaaccagtcccgtacaaattcc
gcctgtaaaatagcttcaccgccggaagcggtaactccgccgcccgaggcgttcataaaatggcgataggtcaccacttctttcattaa
ttcttcaacggaaatttctttaccgccgtgcaaatcccaggtgtctctgttatggcaatatttacaacgcattaagcagccttgtaaaaataa
aataaagcggattcccggcccgtcaactgtcccgcaggtttcaaatgaatgaattcgtcctaaaaccgacataatatgccctaaataa
tcaacaaaatatagcaagaagattatagcaaagaatttcgttttttttcagagaatagtcaaatcttcgcaaaaaactaccgcacttttatc
cgctttaatcaggggaattaaaacaaaaaaattccgcctattgaggcggaatttattaagcaataagacaaactctcaatttaatacttc
cttcttttctagtattgataagattgaaaccttgcaaggatgacggcggatttgccgtcactctcacccaactaatgtggacgactggtaa
accattgcattagaccaatgcaaacaccaccaccgacgatgttacctaaagtaacaggaattaaattttaattactaaatggtacatat
ctaaatttgcaaactgctcggcatttaaaccgttgcctgccagaattccggcgatgcgaaatttgcaattaccatgcccataggatca

```
taaacatatttgctacgcagtgttcaaagcctgaagcgacaaayaacccgatcggcaggatcataataaaagctttatccgttagagt
yttgccggcataggccatccaaacggcaatacataccataatgttgcaaagaatacctaaacagaaggcttcaayccaggtatgttct
attttatgttgtgccgtatttaaaatggttaatccccactgaccgtttgccgccatgatctgaccggaaaaccaaattaatgcaacaataa
ataaaccgccgacaaaattaccgaartaaaccacaatccagttacgtaacatctgaattgttgtaattttactctcaaagcgggcaata
gtcgataaagttgatgaagtaaatagttcacagccgcaaaccgccaccataattaccccgagagagaacaccaaaccgccgacc
agtttagttaatccccaaggcgctcccgcagaggctgtttgagttgttgtataaaaaacgaatgcaagagcaataaacataccggcag
agatcgccgataaaaatgaataggcttgttttttcgtagctttataaacgccgacgtctaacccggtttgagccatctcggttggcgaagc
catccaagccaatttaaaatcttccgatttcattgagctttccttagtaataaaaactactcggaaatgagtagaactgccttaaagcataa
atgatagattaaaaaatccaaaattgttgaatattatttaacggggggattataaaagattcataaattagataatagctaatttgagtgat
ccatatcaccttttacagattttttgacctaaatcaaaattacccaaatagagtaataataccattataaagggtgtggatttattcctttggttt
acgagataaattgctatttaagctgatttctgataaaaagtgcggtagattttcccaaaaataaggaaacacaaaatggcagaagaa
acaattttcagtaaaattattcgtaaagaaattcccgccgacattatatatcaagacgatcttgtcaccgcatttcgcgatattgcgccgca
ggcaaaaactcatattttaattattccgaataaattgattccgacagtaaacgacgtaaccgcccatcgtcgacatcgatgctcttctgcg
ttaattaacaattgggatcctctagactttgcttccagatgtatgctctcctccggagagtaccgtgactttattttcggcacaaatacaggg
gtcgatggataaatacggcgatagtttcctgacggatgatccgtatgtaccggcggaagacaagctgcaaacctgtcagatggagatt
gatttaatggcggatgtgctgagagcaccgccccgtgaatccgcagaactgatccgctatgtgtttgcggatgattggccggaataaat
aaagccgggcttaatacagattaagcccgtatagggtattattactgaataccaaacagcttacggaggacggaatgttacccattga
gacaaccagactgccttctgattattaatattttcactattaatcagaaggaataaccatgaatttacccggattgacctgaatacctgg
aatcgcagggaacactttgccctttatcgtcagcagattaaatgcggattcagcctgaccaccaaactcgatattaccgctttgcgtacc
gcactggcggagacaggttataagtttatccgctgatgatttacctgatctcccgggctgttaatcagtttccggagttccggatggcact
gaaagacaatgaacttatttactgggaccagtcagacccggtctttactgtctttcataaagaaaccgaaacattctctgcactgtcctgc
cgttattttccggatctcagtgagtttatggcaggttataatgcggtaacgcagaatatcagcatgataccagattgtttccgcagggaa
atttaccggagaatcacctgaatatatcatcattaccgtgggtgagttttgacgggatttaacctgaacatcaccggaaatgatgattatttt
gccccggttttacgatggcaaagtttcagcaggaaggtgaccgcgtattattacctgtttctgtacaggttcatcatgcagtctgtgatgg
cttcatgcagcacggtttattaatacacttcagctgatgtgtgataacatactgaaataaattaattaattctgtatttaagccaccgtatcc
ggcaggaatggtggcttttttttatattttaaccgtaatctgtaatttcgtttcagactggttcaggatgagctcgcttggactcctgttgatag
atccagtaatgacctcagaactccatctggatttgttcagaacgctcggttgccgccgggcgttttttattggtgagaatccaagcactag
cggcgcgccggccggcccggtgtgaaataccgcacagatgcgtaaggagaaaataccgcatcaggcgctcttccgcttcctcgctc
actgactcgctgcgctcggtcgttcggctgcggcgagcggtatcagctcactcaaaggcggtaatacggttatccacagaatcaggg
gataacgcaggaaagaacatgtgagcaaaaggccagcaaaaggccaggaaccgtaaaaaggccgcgttgctggcgtttttccat
aggctccgcccccctgacgagcatcacaaaaatcgacgctcaagtcagaggtggcgaaacccgacaggactataaagataccag
gcgtttccccctggaagctccctcgtgcgctctcctgttccgaccctgccgcttaccggatacctgtccgcctttctcccttcgggaagcgt
ggcgctttctcatagctcacgctgtaggtatctcagttcggtgtaggtcgttcgctccaagctgggctgtgtgcacgaaccccccgttcag
cccgaccgctgcgccttatccggtaactatcgtcttgagtccaacccggtaagacacgacttatcgccactggcagcagccactggta
acaggattagcagagcgaggtatgtaggcggtgctacagagttcttgaagtggtggcctaactacggctacactagaaggacagtat
ttggtatctgcgctctgctgaagccagttaccttcggaaaaagagttggtagctcttgatccggcaaacaaaccaccgctggtagcggt
ggttttttgtttgcaagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaaggccggccgcggccgcc
atcggcattttcttttgcgttttatttgttaactgttaattgtccttgttcaaggatgctgtctttgacaacagatgttttcttgcctttgatgttcagca
ggaagctcggcgcaaacgttgattgtttgtctgcgtagaatcctctgtttgtcatatagcttgtaatcacgacattgtttcctttcgcttgaggt
```

-continued acagcgaagtgtgagtaagtaaaggttacatcgttaggatcaagatccattttttaacacaaggccagttttgttcagcggcttgtatggg
ccagttaaagaattagaaacataaccaagcatgtaaatatcgttagacgtaatgccgtcaatcgtcattttgatccgcgggagtcagtg
aacaggtaccatttgccgttcattttaaagacgttcgcgcgttcaatttcatctgttactgtgttagatgcaatcagcggtttcatcacttttttca
gtgtgtaatcatcgtttagctcaatcataccgagagcgccgtttgctaactcagccgtgcgttttttatcgctttgcagaagttttttgactttcttg
acggaagaatgatgtgcttttgccatagtatgctttgttaaataaagattcttcgccttggtagccatcttcagttccagtgttttgcttcaaata
ctaagtatttgtggcctttatcttctacgtagtgaggatctctcagcgtatggttgtcgcctgagctgtagttgccttcatcgatgaactgctgt
acattttgatacgttttccgtcaccgtcaaagattgattataatcctctacaccgttgatgttcaaagagctgtctgatgctgatacgttaac
ttgtgcagttgtcagtgtttgtttgccgtaatgtttaccggagaaatcagtgtagaataaacggattttccgtcagatgtaaatgtggctgaa
cctgaccattcttgtgtttggtatttaggatagaatcatttgcatcgaatttgtcgctgtctttaaagacgcggccagcgttttttccagctgtca
atagaagtttcgccgacttttgatagaacatgtaaatcgatgtgtcatccgcattttaggatctccggctaatgcaaagacgatgtgta
gccgtgatagtttgcgacagtgccgtcagcgttttgtaatggccagctgtcccaaacgtccaggccttttgcagaagagatattttttaattg
tggacgaatcaaattcagaaacttgatatttttcatttttttgctgttcagggatttgcagcatatcatggcgtgtaatatgggaaatgccgtat
gtttccttatatggcttttggttcgtttctttcgcaaacgcttgagttgcgcctcctgccagcagtgcggtagtaaaggttaatactgttgcttgtt
ttgcaaacttttttgatgttcatcgttcatgtctcctttttatgtactgtgttagcggtctgcttcttccagccctcctgtttgaagatggcaagttagt
tacgcacaataaaaaaagacctaaaatatgtaaggggtgacgccaaagtatacactttgcccttacacattttaggtcttgcctgcttta
tcagtaacaaacccgcgcgatttacttttcgacctcattctattagactctcgtttggattgcaactggtctatttttcctcttttgtttgatagaaa
atcataaaaggatttgcagactacgggcctaaagaactaaaaaatctatctgtttcttttcattctctgtatttttatagtttctgttgcatgggc
ataaagttgccttttaatcacaattcagaaaatatcataatatctcatttcactaaataatagtgaacggcaggtatatgtgatgggttaaa
aaggatcggcggccgctcgatttaaatc (nucleotide sequence of ldhA-gene from strain DD1)
SEQ ID NO: 10 ttgacaaaatcagtatgtttaaataaggagctaactatgaaagttgccgtttacagtactaaaaattatgatcgcaaacatctggatttgg
cgaataaaaaatttaattttgagcttcatttctttgattttttacttgatgaacaaaccgcgaaaatggcggagggcgccgatgccgtctgta
ttttcgtcaatgatgatgcgagccgcccggtgttaacaaagttggcgcaaatcggagtgaaaattatcgctttacgttgtgccggttttaat
aatgtggatttggaggcggcaaaagagctgggattaaaagtcgtacgggtgcctgcgtattcgccggaagccgttgccgagcatgcg
atcggattaatgctgactttaaaccgccgtatccataaggcttatcagcgtacccgcgatgcgaattttctctggaaggattggtcggtttt
aatatgttcggcaaaaccgccggagtgattggtacgggaaaaatcggcttggcggctattcgcattttaaaaggcttcggtatggacgtt
ctggcgtttgatccttttaaaaatccggcggcggaagcgttgggcgcaaaatatgtcggtttagacgagctttatgcaaaatcccatgtta
tcactttgcattgcccggctacggcggataattatcatttattaaatgaagcggcttttaataaaatgcgcgacggtgtaatgattattaata
ccagccgcggcgttttaattgacagccgggcggcaatcgaagcgttaaaacggcagaaaatcggcgctctcggtatggatgtttatg
aaaatgaacgggatttgttttcgaggataaatctaacgatgttattacggatgatgtattccgtcgcctttcttcctgtcataatgtgcttttttac
cggtcatcaggcgttttaacggaagaagcgctgaataatatcgccgatgtgactttatcgaatattcaggcggtttccaaaaatgcaac
gtgcgaaaatagcgttgaaggctaa (amino acid sequence of LdhA from strain DD1)
SEQ ID NO: 11

MTKSVCLNKELTMKVAVYSTKNYDRKHLDLANKKFNFELHFFDFLLDEQTAKMAEGADAVCIFV

NDDASRPVLTKLAQIGVKIIALRCAGFNNVDLEAAKELGLKVVRVPAYSPEAVAEHAIGLMLTLN

RRIHKAYQRTRDANFSLEGLVGFNMFGKTAGVIGTGKIGLAAIRILKGFGMDVLAFDPFKNPAAE

ALGAKYVGLDELYAKSHVITLHCPATADNYHLLNEAAFNKMRDGVMIINTSRGVLIDSRAAIEAL

KRQKIGALGMDVYENERDLFFEDKSNDVITDDVFRRLSSCHNVLFTGHQAFLTEEALNNIADVT

LSNIQAVSKNATCENSVEG (nucleotide sequence of pflA-gene from strain DD1)

SEQ ID NO: 12 atgtcggttttaggacgaattcattcatttgaaacctgcgggacagttgacgggccgggaatccgctttatttttattttttacaaggctgcttaa
tgcgttgtaaatactgccataatagagacacctgggatttgcacggcggtaaagaaatttccgttgaagaattaatgaaagaagtggtg
acctatcgccatttatgaacgcctcgggcggcggagttaccgcttccggcggtgaagctattttacaggcggaatttgtacgggactgg
ttcagagcctgccataaagaaggaattaatacttgcttggataccaacggtttcgtccgtcatcatgatcatattattgatgaattgattgat
gacacggatcttgtgttgcttgacctgaaagaaatgaatgaacgggttcacgaaagcctgattggcgtgccgaataaaagagtgctcg
aattcgcaaaatatttagcggatcgaaatcagcgtacctggatccgccatgttgtagtgccgggttatacagatagtgacgaagatttgc
acatgctggggaatttcattaaagatatgaagaatatcgaaaaagtggaattattaccttatcaccgtctaggcgcccataaatgggaa
gtactcggcgataaatacgagcttgaagatgtaaaaccgccgacaaaagaattaatggagcatgttaaggggttgcttgcaggctac
gggcttaatgtgacatattag (amino acid sequence of PflA from strain DD1)

SEQ ID NO: 13

MSVLGRIHSFETCGTVDGPGIRFILFLQGCLMRCKYCHNRDTWDLHGGKEISVEELMKEVVTY
RHFMNASGGGVTASGGEAILQAEFVRDWFRACHKEGINTCLDTNGFVRHHDHIIDELIDDTDLV
LLDLKEMNERVHESLIGVPNKRVLEFAKYLADRNQRTWIRHVVVPGYTDSDEDLHMLGNFIKD
MKNIEKVELLPYHRLGAHKWEVLGDKYELEDVKPPTKELMEHVKGLLAGYGLNVTY (nucleotide sequence of pflD-gene from strain DD1)

SEQ ID NO: 14 atggctgaattaacagaagctcaaaaaaaagcatgggaaggattcgttcccggtgaatggcaaaacggcgtaaatttacgtgactttt
atccaaaaaaactatactccgtatgaaggtgacgaatcattcttagctgatgcgactcctgcaaccagcgagttgtggaacagcgtga
tggaaggcatcaaaatcgaaaacaaaactcacgcacctttagatttcgacgaacatactccgtcaactatcacttctcacaagcctgg
ttatatcaataaagatttagaaaaaaatcgttggtcttcaaacagacgctccgttaaaacgtgcaattatgccgtacggcggtatcaaaat
gatcaaaggttcttgcgaagtttacggtcgtaaattagatccgcaagtagaatttattttcaccgaatatcgtaaaacccataaccaagg
cgtattcgacgtttatacgccggatattttacgctgccgtaaatcaggcgtgttaaccggtttaccggatgcttacggtcgtggtcgtattatc
ggtgactaccgtcgtttagcggtatacggtattgattacctgatgaaagataaaaaagcccaattcgattcattacaaccgcgtttggaa
gcgggcgaagacattcaggcaactatccaattacgtgaagaaattgccgaacaacaccgcgctttaggcaaaatcaaagaaatgg
cggcatcttacggttacgacatttccggccctgcgacaaacgcacaggaagcaatccaatggacatattttgcttatctggcagcggtt
aaatcacaaaacggtgcggcaatgtcattcggtcgtacgtctacattcttagatatctatatcgaacgtgacttaaaacgcggtttaatca
ctgaacaacaggcgcaggaattaatgcaccacttagtaatgaaattacgtatggttcgtttcttacgtacgccgaatacgatcaattatt
ctcaggcgacccgatgtgggcaaccgaaactatcgccggtatgggcttagacggtcgtccgttggtaactaaaaacagcttccgcgt
attacatactttatacactatgggtacttctccggaaccaaacttaactattctttggtccgaacaattacctgaagcgttcaaacgtttctgt
gcgaaagtatctattgatacttcctccgtacaatacgaaaatgatgacttaatgcgtcctgacttcaacaacgatgactatgcaatcgcat
gctgcgtatcaccgatggtcgtaggtaaacaaatgcaattcttcggtgcgcgcgcaaacttagctaaaactatgttatacgcaattaac
ggcggtatcgatgagaaaaatggtatgcaagtcggtcctaaaactgcgccgattacagacgaagtattgaatttcgataccgtaatcg
aacgtatggacagtttcatggactggttggcgactcaatatgtaaccgcattgaacatcatccacttcatgcacgataaatatgcatatg
aagcggcattgatggcgttccacgatcgcgacgtattccgtacaatggcttgcggtatcgcgggtctttccgtggctgcggactcattatc
cgcaatcaaatgcgaaagttaaaccgattcgcggcgacatcaaagataaagacggtaatgtcgtggcctcgaatgttgctatcga
cttcgaaattgaaggcgaatatccgcaattcggtaacaatgatccgcgtgttgatgatttagcggtagacttagttgaacgtttcatgaaa
aaagttcaaaaacacaaaacttaccgcaacgcaactccgacacaatctatcctgactatcacttctaacgtggtatacggtaagaaa
accggtaatactccggacggtcgtcgagcaggcgcgccattcggacccgggtgcaaacccaatgcacggtcgtgaccaaaaaggt
gcggttgcttcacttacttctgtggctaaacttccgttcgcttacgcgaaagacggtatttcatatacccttctctatcgtaccgaacgcattag
gtaaagatgacgaagcgcaaaaacgcaaccttgccggtttaatggacggttatttccatcatgaagcgacagtggaaggcggtcaa -continued cacttgaatgttaacgttcttaaccgtgaaatgttgttagacgcgatggaaaatccggaaaaatacccgcaattaaccattcgtgtttcag gttacgcggttcgtttcaactcattaactaaagagcaacaacaagacgtcatcactcgtacgtttacacaatcaatgtaa (amino acid of PflD from strain DD1)

SEQ ID NO: 15

MAELTEAQKKAWEGFVPGEWONGVNLRDFIQKNYTPYEGDESFLADATPATSELWNSVMEGI

KIENKTHAPLDFDEHTPSTITSHKPGYINKDLEKIVGLQTDAPLKRAIMPYGGIKMIKGSCEVYGR

KLDPQVEFIFTEYRKTHNQGVFDVYTPDILRCRKSGVLTGLPDAYGRGRIIGDYRRLAVYGIDYL

MKDKKAQFDSLQPRLEAGEDIQATIQLREEIAEQHRALGKIKEMAASYGYDISGPATNAQEAIQ

WTYFAYLAAVKSQNGAAMSFGRTSTFLDIYIERDLKRGLITEQQAQELMDHLVMKLRMVRFLRT

PEYDQLFSGDPMWATETIAGMGLDGRPLVTKNSFRVLHTLYTMGTSPEPNLTILWSEQLPEAF

KRFCAKVSIDTSSVQYENDDLMRPDFNNDDYAIACCVSPMVVGKQMQFFGARANLAKTMLYAI

NGGIDEKNGMQVGPKTAPITDEVLNFDTVIERMDSFMDWLATQYVTALNIIHFMHDKYAYEAAL

MAFHDRDVFRTMACGIAGLSVAADSLSAIKYAKVKPIRGDIKDKDGNVVASNVAIDFEIEGEYPQ

FGNNDPRVDDLAVDLVERFMKKVQKHKTYRNATPTQSILTITSNVVYGKKTGNTPDGRRAGAP

FGPGANPMHGRDQKGAVASLTSVAKLPFAYAKDGISYTFSIVPNALGKDDEAQKRNLAGLMDG

YFHHEATVEGGQHLNVNVLNREMLLDAMENPEKYPQLTIRVSGYAVRFNSLTKEQQQDVITRT

FTQSM (nucleotide sequence of wcaJ-gene from strain DD1 with insertion
of cytosine between nucleotides 81 and 82)

SEQ ID NO: 16

Atgataaaacgccttttcgatattgttgtcgcattgatagcattgattttgttttcgcccttatatttgtttgtggcttat<u>c</u>aaggtaaaacaaaatt tgggatcaccggtgttatttaaacaaacccgcccccggattgcatggtaaacccttttgagatgattaagttcagaacaatgaaagacgg cgcagatgaaaacggtaatattttgccggatgcggagcgcttaacacctttcggcaaaatgttgcgcgctaccagtctggacgagttgc cggaactttggaatgtattaaaaggtgatatgagtctggtggggccgcgtcctctactgatggaatatttgccgctgtataacgaaagac aggctaagcgccatgaagtgaaacccggaattaccggttatgcacaggtaaacggtcgcaatgccatcagttgggagcagaaattt gaattggatgcctggtatgttgaacatcaatccttgtggctggatttgaaaattatcgcaaagaccatccaaaaagtgatcgcaaaaga cgatattaatgcggcagatgatgccaccatgcctaaatttgaagggaataaaaaaatcatga

---

The invention claimed is:

1. A modified microorganism having, compared to its wild-type, a deletion of the wcaJ-gene or an introduction of at least one mutation into the wcaJ-gene that leads to the expression of a truncated enzyme encoded by the wcaJ-gene in which at least 100 amino acids of the wild-type enzyme encoded by the wcaJ-gene are deleted from the C-terminal end;
   wherein the wild-type from which the modified microorganism has been derived belongs to the family of Pasteurellaceae and wherein the wild-type refers to the naturally occurring microorganism that has not been genetically modified,
   wherein the wcaJ-gene in the wildtype comprises a nucleic acid
   encoding an amino acid sequence which is at least 95% identical to SEQ ID NO: 4 over the total length of the amino acid sequence of SEQ ID NO: 4.

2. Modified microorganism according to claim 1, wherein the wild-type from which the modified microorganism has been derived has a 16S rDNA of SEQ ID NO: 1 or a sequence, which shows a sequence homology of at least 96% with SEQ ID NO: 1.

3. Modified microorganism according to claim 1, wherein the wild-type from which the modified microorganism has been derived belongs to the genus *Basfia*.

4. Modified microorganism according to claim 3, wherein the wild-type from which the modified microorganism has been derived belongs to the species *Basfia succiniciproducens*.

5. Modified microorganism according to claim 4, wherein the wild-type from which the modified microorganism has been derived is *Basfia succiniciproducens* strain DD1 as deposited under DSM 18541 with the DSMZ, Germany.

6. Modified microorganism according to claim 1, wherein the microorganism further has, compared to its wild-type,
   i) a reduced pyruvate formate lyase activity,
   ii) a reduced lactate dehydrogenase activity, or
   iii) a reduced pyruvate formate lyase activity and a reduced lactate dehydrogenase activity.

7. Modified microorganism according to claim 6, wherein the microorganism comprises:
   A) a deletion of the ldhA-gene or at least a part thereof, a deletion of a regulatory element of the ldhA-gene or at least a part thereof or an introduction of at least one mutation into the ldhA-gene;
   B) a deletion of the pflD-gene or at least a part thereof, a deletion of a regulatory element of the pflD-gene or at least a part thereof or an introduction of at least one mutation into the pflD-gene;
   C) a deletion of the pflA-gene or at least a part thereof, a deletion of a regulatory element of the pflA-gene or at least a part thereof or an introduction of at least one mutation into the pflA-gene;
   D) a deletion of the ldhA-gene or at least a part thereof, a deletion of a regulatory element of the ldhA-gene or at least a part thereof or an introduction of at least one mutation into the ldhA-gene
   and
   a deletion of the pflD-gene or at least a part thereof, a deletion of a regulatory element of the pflD-gene or at least a part thereof or an introduction of at least one mutation into the pflD-gene;
   or
   E) a deletion of the ldhA-gene or at least a part thereof, a deletion of a regulatory element of the ldhA-gene or at least a part thereof or an introduction of at least one mutation into the ldhA-gene
   and
   a deletion of the pflA-gene or at least a part thereof, a deletion of a regulatory element of the pflA-gene or at least a part thereof an introduction of at least one mutation into the pflA-gene.

8. A method of producing an organic compound comprising:
   I) cultivating the modified microorganism of claim 1 in a culture medium comprising at least one assimilable carbon source to allow the modified microorganism to produce the organic compound, thereby obtaining a fermentation broth comprising the organic compound;
   II) recovering the organic compound from the fermentation broth obtained in process step I),
   wherein the organic compound is a carboxylic, dicarboxylic or tricarboxylic acid.

9. Method according to claim 8, wherein the organic compound is succinic acid.

10. Method according to claim 8, wherein the assimilable carbon source is selected from the group consisting of sucrose, maltose, D-glucose, glycerol, mixtures of glycerol and D-glucose, mixtures of glycerol and sucrose, mixtures of glycerol and D-xylose, mixtures of glycerol and mixtures of maltose and D-glucose and fructose.

11. Method according to claim 8, wherein the process further comprises the process step:
   III) conversion of the organic compound contained in the fermentation broth obtained in process step I) or conversion of the recovered organic compound obtained in process step II) into a secondary organic product being different from the organic compound by at least one chemical reaction.

12. Method according to claim 11, wherein the organic compound is succinic acid and wherein the secondary organic product is selected from the group consisting of succinic acid esters or polymers thereof, tetrahydrofuran (THF), 1,4-butanediol (BDO), gamma-butyrolactone (GBL) and pyrrolidones.

* * * * *